US010151636B2

(12) United States Patent
Tzvieli et al.

(10) Patent No.: US 10,151,636 B2
(45) Date of Patent: Dec. 11, 2018

(54) EYEGLASSES HAVING INWARD-FACING AND OUTWARD-FACING THERMAL CAMERAS

(71) Applicant: Facense Ltd., Kiryat Tivon (IL)

(72) Inventors: Arie Tzvieli, Berkeley, CA (US); Gil Thieberger, Kiryat Tivon (IL); Ari M Frank, Haifa (IL)

(73) Assignee: Facense Ltd., Kiryat Tivon (IL)

( * ) Notice: Subject to any disclaimer, the term of this patent is extended or adjusted under 35 U.S.C. 154(b) by 0 days.

(21) Appl. No.: 15/833,079

(22) Filed: Dec. 6, 2017

(65) Prior Publication Data
US 2018/0094982 A1  Apr. 5, 2018

Related U.S. Application Data

(63) Continuation-in-part of application No. 15/722,434, filed on Oct. 2, 2017, and a continuation-in-part of
(Continued)

(51) Int. Cl.
*A61B 5/05* (2006.01)
*G01J 5/02* (2006.01)
(Continued)

(52) U.S. Cl.
CPC ........... *G01J 5/0205* (2013.01); *A61B 5/015* (2013.01); *A61B 5/165* (2013.01); *A61B 5/6803* (2013.01);
(Continued)

(58) Field of Classification Search
CPC ........... G06K 9/00302; G06K 9/00228; G06K 9/00234; A61B 5/0077; A61B 5/015; A61B 5/6821; A61B 5/165; A61B 5/02055
See application file for complete search history.

(56) References Cited

U.S. PATENT DOCUMENTS

| 5,143,086 A | 9/1992 | Duret et al. |
| 5,664,578 A | 9/1997 | Boczan |

(Continued)

FOREIGN PATENT DOCUMENTS

| EP | 2233071 A1 | 9/2013 |
| WO | WO2016025323 | 2/2016 |

OTHER PUBLICATIONS

Written opinion of the international searching authority, PCT/IB2017/056066, dated Jan. 29, 2018.

(Continued)

*Primary Examiner* — Joel Lamprecht
(74) *Attorney, Agent, or Firm* — Active Knowledge Ltd.

(57) ABSTRACT

Described herein are systems and methods for detecting a physiological response based on thermal measurements while accounting for effects of the environment. In one embodiment, a system includes an inward-facing head-mounted thermal camera ($CAM_{in}$) that takes thermal measurements of a region of interest ($TH_{ROI}$) on a user's face, and an outward-facing head-mounted thermal camera ($CAM_{out}$) that takes thermal measurements of the environment ($TH_{ENV}$). $CAM_{in}$ does not occlude the region of interest, and the system further includes a computer that detects the physiological response based on $TH_{ROI}$ and $TH_{ENV}$. Optionally, the computer generates feature values based on sets of $TH_{ROI}$ and $TH_{ENV}$, and utilizes a machine learning-based model to detect, based on the feature values, the physiological response.

21 Claims, 15 Drawing Sheets

Related U.S. Application Data application No. 15/182,592, filed on Jun. 14, 2016, said application No. 15/722,434 is a continuation-in-part of application No. 15/231,276, filed on Aug. 8, 2016, and a continuation-in-part of application No. 15/284,528, filed on Oct. 3, 2016, application No. 15/833,079, which is a continuation-in-part of application No. 15/635,178, filed on Jun. 27, 2017, and a continuation-in-part of application No. 15/284,528, filed on Oct. 3, 2016, and a continuation-in-part of application No. 15/231,276, filed on Aug. 8, 2016, and a continuation-in-part of application No. 15/182,592, filed on Jun. 14, 2016, and a continuation-in-part of application No. 15/182,566, filed on Jun. 14, 2016, now Pat. No. 9,867,546.

(60) Provisional application No. 62/566,572, filed on Oct. 2, 2017, provisional application No. 62/408,677, filed on Oct. 14, 2016, provisional application No. 62/456,105, filed on Feb. 7, 2017, provisional application No. 62/480,496, filed on Apr. 2, 2017, provisional application No. 62/175,319, filed on Jun. 14, 2015, provisional application No. 62/202,808, filed on Aug. 8, 2015, provisional application No. 62/236,868, filed on Oct. 3, 2015, provisional application No. 62/354,833, filed on Jun. 27, 2016, provisional application No. 62/372,063, filed on Aug. 8, 2016, provisional application No. 62/480,496, filed on Apr. 2, 2017.

(51) Int. Cl.

| | |
|---|---|
| *G16H 50/20* | (2018.01) |
| *G06T 7/00* | (2017.01) |
| *G01N 25/00* | (2006.01) |
| *G01J 5/08* | (2006.01) |
| *G16H 30/40* | (2018.01) |
| *A61B 5/01* | (2006.01) |
| *A61B 5/16* | (2006.01) |
| *H04N 5/225* | (2006.01) |
| *H04N 5/33* | (2006.01) |
| *G01J 5/00* | (2006.01) |
| *A61B 5/00* | (2006.01) |
| *A61B 5/024* | (2006.01) |
| *A61B 5/0402* | (2006.01) |
| *A61B 5/0476* | (2006.01) |
| *A61B 5/053* | (2006.01) |
| *A61B 5/08* | (2006.01) |
| *G02B 27/01* | (2006.01) |

(52) U.S. Cl.
CPC ............ *A61B 5/748* (2013.01); *G01J 5/0025* (2013.01); *G01J 5/0265* (2013.01); *G01J 5/0806* (2013.01); *G01N 25/005* (2013.01); *G02B 27/0172* (2013.01); *G02B 27/0176* (2013.01); *G06T 7/0012* (2013.01); *G16H 30/40* (2018.01); *G16H 50/20* (2018.01); *H04N 5/2251* (2013.01); *H04N 5/33* (2013.01); *A61B 5/0022* (2013.01); *A61B 5/0075* (2013.01); *A61B 5/0077* (2013.01); *A61B 5/02405* (2013.01); *A61B 5/02416* (2013.01); *A61B 5/0402* (2013.01); *A61B 5/0476* (2013.01); *A61B 5/0531* (2013.01); *A61B 5/0816* (2013.01); *A61B 5/4094* (2013.01); *A61B 5/411* (2013.01); *A61B 5/441* (2013.01); *A61B 5/4803* (2013.01); *A61B 5/4845* (2013.01); *A61B 5/4875* (2013.01); *A61B 5/6898* (2013.01); *A61B 5/744* (2013.01); *A61B 5/746* (2013.01); *A61B 2560/0252* (2013.01); *A61B 2562/0271* (2013.01); *G01J 2005/0077* (2013.01); *G01J 2005/0085* (2013.01); *G02B 2027/0138* (2013.01); *G06T 2207/30201* (2013.01)

(56) References Cited

U.S. PATENT DOCUMENTS

| | | |
|---|---|---|
| 6,121,953 A | 9/2000 | Walker |
| 6,286,958 B1 | 9/2001 | Koest et al. |
| 6,771,423 B2 | 8/2004 | Geist |
| 6,837,615 B2 | 1/2005 | Newman |
| 6,996,256 B2 | 2/2006 | Pavlidis |
| 7,027,621 B1 | 4/2006 | Prokoski |
| 7,135,980 B2 | 11/2006 | Moore et al. |
| 7,138,905 B2 | 11/2006 | Pavlidis et al. |
| 8,149,273 B2 | 4/2012 | Liu et al. |
| 8,289,443 B2 | 10/2012 | MacKenzie |
| 8,334,872 B2 | 12/2012 | Epps et al. |
| 8,360,986 B2 | 1/2013 | Farag et al. |
| 8,573,866 B2 | 11/2013 | Bond et al. |
| 8,585,588 B2 | 11/2013 | Kovarik et al. |
| 8,723,790 B2 | 5/2014 | Schaefer |
| 8,768,438 B2 | 7/2014 | Mestha et al. |
| 8,786,698 B2 | 7/2014 | Chen et al. |
| 8,855,384 B2 | 10/2014 | Kyal et al. |
| 8,964,298 B2 | 2/2015 | Haddick et al. |
| 9,019,174 B2 | 4/2015 | Jerauld |
| 9,020,185 B2 | 4/2015 | Mestha et al. |
| 9,194,749 B2 | 11/2015 | Pompei |
| 9,211,069 B2 | 12/2015 | Larsen et al. |
| 9,410,854 B2 | 8/2016 | Padiy |
| 9,569,734 B2 | 2/2017 | Thieberger et al. |
| 2002/0080094 A1 | 6/2002 | Biocca et al. |
| 2005/0083248 A1 | 4/2005 | Biocca et al. |
| 2005/0271117 A1 | 12/2005 | Grassi et al. |
| 2007/0047768 A1 | 3/2007 | Gordon et al. |
| 2007/0248238 A1 | 10/2007 | Abreu |
| 2007/0265507 A1 | 11/2007 | de Lemos |
| 2008/0260212 A1 | 10/2008 | Moskal et al. |
| 2009/0221888 A1 | 9/2009 | Wijesiriwardana |
| 2009/0237564 A1 | 9/2009 | Kikinis et al. |
| 2010/0191124 A1 | 7/2010 | Prokoski |
| 2010/0280334 A1 | 11/2010 | Carlson et al. |
| 2012/0062719 A1 | 3/2012 | Debevec et al. |
| 2012/0105473 A1 | 5/2012 | Bar-Zeev et al. |
| 2012/0197093 A1 | 8/2012 | LeBoeuf et al. |
| 2012/0327194 A1 | 12/2012 | Shiratori et al. |
| 2013/0124039 A1 | 5/2013 | Abreu |
| 2013/0215244 A1 | 8/2013 | Mestha et al. |
| 2013/0241805 A1 | 9/2013 | Gomez |
| 2013/0257709 A1 | 10/2013 | Raffle et al. |
| 2014/0180449 A1 | 6/2014 | Sung |
| 2014/0282911 A1 | 9/2014 | Bare et al. |
| 2014/0347265 A1 | 11/2014 | Aimone et al. |
| 2014/0366049 A1 | 12/2014 | Lehtiniemi et al. |
| 2015/0087924 A1 | 3/2015 | Li et al. |
| 2015/0126845 A1* | 5/2015 | Jin ............ G02B 27/017 600/383 |
| 2015/0148618 A1 | 5/2015 | Sitko et al. |
| 2015/0157255 A1 | 6/2015 | Nduka |
| 2015/0297126 A1 | 10/2015 | Atsumori et al. |
| 2015/0310263 A1 | 10/2015 | Zhang et al. |
| 2015/0359443 A1 | 12/2015 | Poh |
| 2016/0015289 A1 | 1/2016 | Simon et al. |
| 2016/0081622 A1* | 3/2016 | Abreu ............ A61B 5/0002 600/549 |
| 2016/0091877 A1 | 3/2016 | Fullam et al. |
| 2016/0098592 A1 | 4/2016 | Lee et al. |
| 2016/0100790 A1 | 4/2016 | Cantu et al. |
| 2016/0170996 A1 | 6/2016 | Frank et al. |
| 2016/0216760 A1 | 7/2016 | Trutna et al. |
| 2016/0224803 A1 | 8/2016 | Frank et al. |
| 2016/0235324 A1 | 8/2016 | Mershin et al. |
| 2016/0270656 A1* | 9/2016 | Samec ............ A61B 3/085 |

(56) References Cited

U.S. PATENT DOCUMENTS

| | | |
|---|---|---|
| 2016/0342835 A1 | 11/2016 | Kaehler |
| 2017/0007167 A1 | 1/2017 | Kostic et al. |
| 2017/0231490 A1 | 8/2017 | Toth et al. |
| 2017/0235931 A1 | 8/2017 | Publicover et al. |

OTHER PUBLICATIONS

Written opinion of the international searching authority, PCT/IB2017/056067, dated Jan. 29, 2018.

Written opinion of the international searching authority, PCT/IB2017/056069, dated Jan. 29, 2018.

Alghoul, K., Alharthi, S., Al Osman, H., & El Saddik, A. (2017). Heart Rate Variability extraction from videos signals: ICA vs. EVM comparison. IEEE Access, 5, 4711-4719.

Al-Khalidi, F. Q., Saatchi, R., Burke, D., Elphick, H., & Tan, S. (2011). Respiration rate monitoring methods: A review. Pediatric pulmonology, 46(6), 523-529.

Appel, V. C., Belini, V. L., Jong, D. H., Magalhães, D. V., & Caurin, G. A. (Aug. 2014). Classifying emotions in rehabilitation robotics based on facial skin temperature. In Biomedical Robotics and Biomechatronics (2014 5th IEEE RAS & EMBS International Conference on (pp. 276-280). IEEE.

Aryal, A., Ghahramani, A., & Becerik-Gerber, B. (2017). Monitoring fatigue in construction workers using physiological measurements. Automation in Construction.

Boccanfuso, L., & O'Kane, J. M. (Jun. 2012). Remote measurement of breathing rate in real time using a high precision, single-point infrared temperature sensor. In Biomedical Robotics and Biomechatronics (BioRob), 2012 4th IEEE RAS & EMBS International Conference on (pp. 1704-1709). IEEE.

Cardone, D., Pinti, P., & Merla, A. (2015). Thermal infrared imaging-based computational psychophysiology for psychometrics. Computational and mathematical methods in medicine, 2015.

Carine Collé, Re-Experience Big-Data, 3 months group project with Sanya Rai Gupta and Florian Puech, UK, London, RCA, IDE, 2014, Amoeba.

Choi, J. S., Bang, J. W., Heo, H., & Park, K. R. (2015). Evaluation of Fear Using Nonintrusive Measurement of Multimodal Sensors. Sensors, 15(7), 17507-17533.

Clay-Warner, J., & Robinson, D. T. (2015). Infrared thermography as a measure of emotion response. Emotion Review, 7(2), 157-162.

Cross, C. B., Skipper, J. A., & Petkie, D. (May 2013). Thermal imaging to detect physiological indicators of stress in humans. In SPIE Defense, Security, and Sensing (pp. 87050I-87050I). International Society for Optics and Photonics.

Fei, J., & Pavlidis, I. (Aug. 2006). Analysis of breathing air flow patterns in thermal imaging. In Engineering in Medicine and Biology Society, 2006. EMBS'06. 28th Annual International Conference of the IEEE (pp. 946-952). IEEE.

Fei, J., & Pavlidis, I. (2010). Thermistor at a distance: unobtrusive measurement of breathing. IEEE Transactions on Biomedical Engineering, 57(4), 988-998.

Fernández-Cuevas, I., Marins, J. C. B., Lastras, J. A., Carmona, P. M. G., Cano, S. P., García-Concepción, M. Á., & Sillero-Quintana, M. (2015). Classification of factors influencing the use of infrared thermography in humans: A review. Infrared Physics & Technology, 71, 28-55.

Ghahramani, A., Castro, G., Becerik-Gerber, B., & Yu, X. (2016). Infrared thermography of human face for monitoring thermoregulation performance and estimating personal thermal comfort. Building and Environment, 109, 1-11.

Hawkes, P. W. (2012). Advances in Imaging and Electron Physics (vol. 171). Academic Press. Chapter 2.

Hong, K., Yuen, P., Chen, T., Tsitiridis, A., Kam, F., Jackman, J., . . . & Lightman+, F. T. S. (Sep. 2009). Detection and classification of stress using thermal imaging technique. In Proc. of SPIE Vol (vol. 7486, pp. 74860I-1).

Ioannou, S., Gallese, V., & Merla, A. (2014). Thermal infrared imaging in psychophysiology: potentialities and limits. Psychophysiology, 51(10), 951-963.

Jenkins, S. D., & Brown, R. D. H. (2014). A correlational analysis of human cognitive activity using Infrared Thermography of the supraorbital region, frontal EEG and self-report of core affective state. QIRT.

Johnson, M. L., Price, P. A., & Jovanov, E. (Aug. 2007). A new method for the quantification of breathing. In Engineering in Medicine and Biology Society, 2007. EMBS 2007. 29th Annual International Conference of the IEEE (pp. 4568-4571). IEEE.

Jovanov, E., Raskovic, D., & Hormigo, R. (2001). Thermistor-based breathing sensor for circadian rhythm evaluation. Biomedical sciences instrumentation, 37, 493-498.

Joyal, C. C., & Henry, M. (2013). Long-wave infrared functional brain imaging in human: a pilot study. The open neuroimaging journal, 7(1).

Kimura, S., Fukuomoto, M., & Horikoshi, T. (Sep. 2013). Eyeglass-based hands-free videophone. In Proceedings of the 2013 International Symposium on Wearable Computers (pp. 117-124). ACM.

Kurz, M., Hölzl, G., Riener, A., Anzengruber, B., Schmittner, T., & Ferscha, A. (Sep. 2012). Are you cool enough for Texas Hold'Em Poker?. In Proceedings of the 2012 ACM Conference on Ubiquitous Computing (pp. 1145-1149). ACM.

Lewis, G. F., Gatto, R. G., & Porges, S. W. (2011). A novel method for extracting respiration rate and relative tidal volume from infrared thermography. Psychophysiology, 48(7), 877-887.

Merla, A. (2014). Thermal expression of intersubjectivity offers new possibilities to human-machine and technologically mediated interactions.

Mizuno, T., & Kume, Y. (Aug. 2015). Development of a Glasses-Like Wearable Device to Measure Nasal Skin Temperature. In International Conference on Human-Computer Interaction (pp. 727-732). Springer International Publishing.

Mizuno, T., Sakai, T., Kawazura, S., Asano, H., Akehi, K., Matsuno, S., . . . & Itakura, N. (Jul. 2015). Facial Skin Temperature Fluctuation by Mental Work-Load with Thermography. In the International Conference on Electronics and Software Science (ICESS2015) Proceedings (pp. 212-215).

Murthy, R., & Pavlidis, I. (2006). Noncontact measurement of breathing function. IEEE Engineering in Medicine and Biology Magazine, 25(3), 57-67.

Murthy, R., Pavlidis, I., & Tsiamyrtzis, P. (Sep. 2004). Touchless monitoring of breathing function. In Engineering in Medicine and Biology Society, 2004. IEMBS'04. 26th Annual International Conference of the IEEE (vol. 1, pp. 1196-1199). IEEE.

Nagaraj, S., Quoraishee, S., Chan, G., & Short, K. R. (Apr. 2010). Biometric study using hyperspectral imaging during stress. In SPIE Defense, Security, and Sensing (pp. 76740K-76740K). International Society for Optics and Photonics.

Nhan, B. R., & Chau, T. (2010). Classifying affective states using thermal infrared imaging of the human face. IEEE Transactions on Biomedical Engineering, 57(4), 979-987.

Pavlidis, I., & Levine, J. (2002). Thermal image analysis for polygraph testing. IEEE Engineering in Medicine and Biology Magazine, 21(6), 56-64.

Pavlidis, I., Dowdall, J., Sun, N., Puri, C., Fei, J., & Garbey, M. (2007). Interacting with human physiology. Computer Vision and Image Understanding, 108(1), 150-170.

Puri, C., Olson, L., Pavlidis, I., Levine, J., & Starren, J. (Apr. 2005). StressCam: non-contact measurement of users' emotional states through thermal imaging. In CHI'05 extended abstracts on Human factors in computing systems (pp. 1725-1728). ACM.

Rajoub, B. A., & Zwiggelaar, R. (2014). Thermal facial analysis for deception detection. IEEE transactions on information forensics and security, 9(6), 1015-1023.

Ramirez, G. A., Fuentes, O., Crites Jr, S. L., Jimenez, M., & Ordonez, J. (2014). Color analysis of facial skin: Detection of emotional state. In Proceedings of the IEEE Conference on Computer Vision and Pattern Recognition Workshops (pp. 468-473).

(56) References Cited

OTHER PUBLICATIONS

Romera-Paredes, B., Zhang, C., & Zhang, Z. (Jul. 2014). Facial expression tracking from head-mounted, partially observing cameras. In Multimedia and Expo (ICME), 2014 IEEE International Conference on (pp. 1-6). IEEE.
Sharma, N., Dhall, A., Gedeon, T., & Goecke, R. (Sep. 2013). Modeling stress using thermal facial patterns: A spatio-temporal approach. In Affective Computing and Intelligent Interaction (ACII), 2013 Humaine Association Conference on (pp. 387-392). IEEE.
Sharma, N., Dhall, A., Gedeon, T., & Goecke, R. (2014). Thermal spatio-temporal data for stress recognition. EURASIP Journal on Image and Video Processing, 2014(1), 28.
Shastri, D., Papadakis, M., Tsiamyrtzis, P., Bass, B., & Pavlidis, I. (2012). Perinasal imaging of physiological stress and its affective potential. IEEE Transactions on Affective Computing, 3(3), 366-378.
Tsiamyrtzis, P., Dowdall, J., Shastri, D., Pavlidis, I. T., Frank, M. G., & Ekman, P. (2007). Imaging facial physiology for the detection of deceit. International Journal of Computer Vision, 71(2), 197-214.
Yang, M., Liu, Q., Turner, T., & Wu, Y. (Jun. 2008). Vital sign estimation from passive thermal video. In Computer Vision and Pattern Recognition, 2008. CVPR 2008. IEEE Conference on (pp. 1-8). IEEE.

* cited by examiner

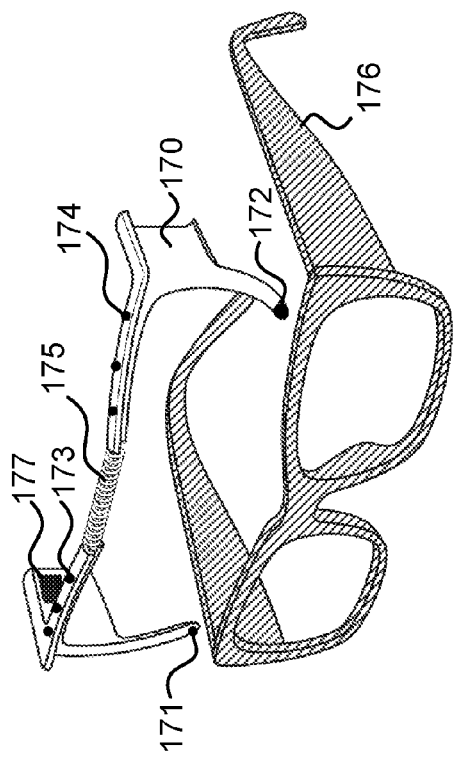
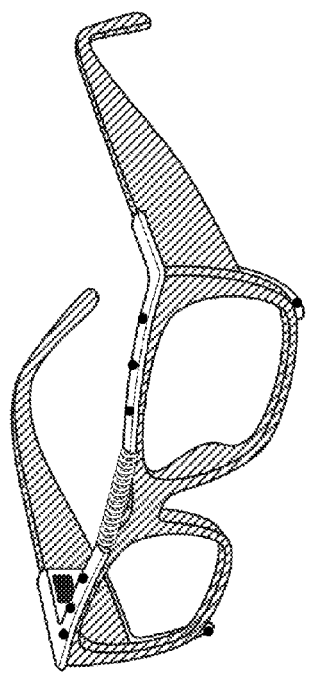
FIG. 17a
FIG. 17b
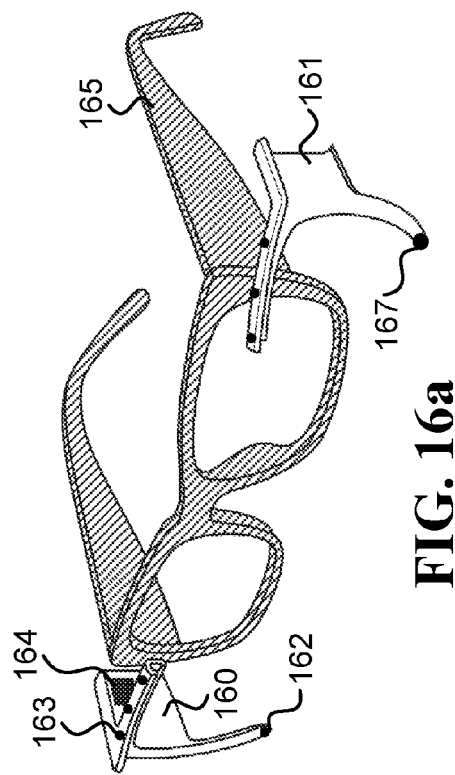
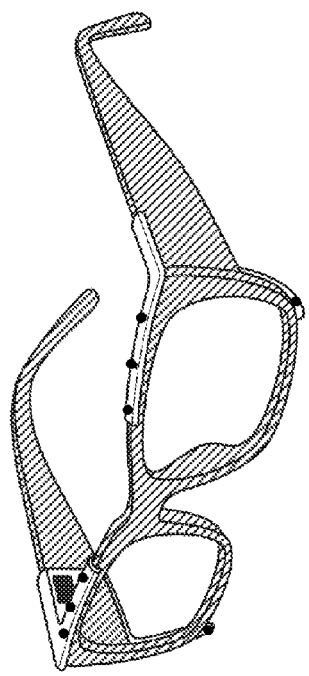
FIG. 16a
FIG. 16b

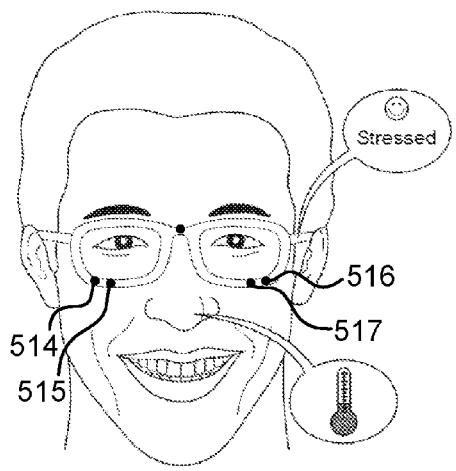
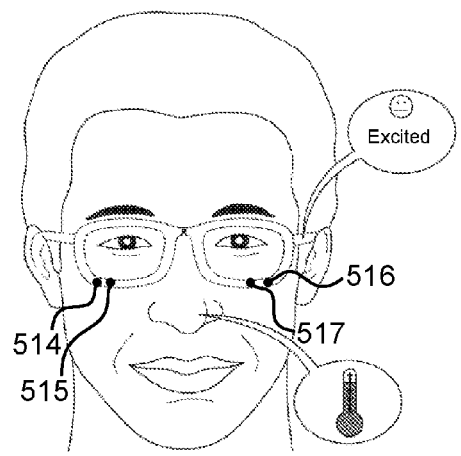
FIG. 21a  FIG. 21b
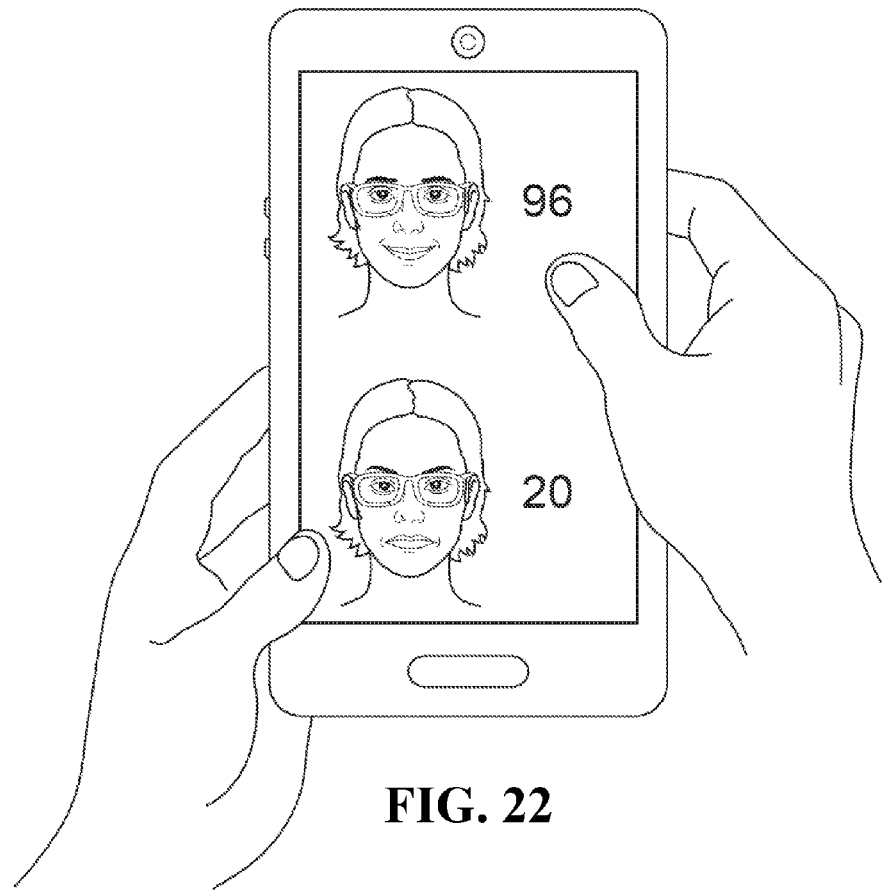
FIG. 22

EYEGLASSES HAVING INWARD-FACING AND OUTWARD-FACING THERMAL CAMERAS

CROSS-REFERENCE TO RELATED APPLICATIONS

This application claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Provisional Patent Application No. 62/566,572 is herein incorporated by reference in its entirety.

This application is a Continuation-In-Part of U.S. application Ser. No. 15/182,566, filed Jun. 14, 2016, now U.S. Pat. No. 9,867,546, which claims priority to U.S. Provisional Patent Application No. 62/175,319, filed Jun. 14, 2015, and U.S. Provisional Patent Application No. 62/202,808, filed Aug. 8, 2015.

This application is also a Continuation-In-Part of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015.

This application is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015.

This application is also a Continuation-In-Part of U.S. application Ser. No. 15/284,528, filed Oct. 3, 2016, which claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

This application is also a Continuation-In-Part of U.S. application Ser. No. 15/635,178, filed Jun. 27, 2017, which claims priority to U.S. Provisional Patent Application No. 62/354,833, filed Jun. 27, 2016, and U.S. Provisional Patent Application No. 62/372,063, filed Aug. 8, 2016.

This application is also a Continuation-In-Part of U.S. application Ser. No. 15/722,434, filed Oct. 2, 2017, which claims priority to U.S. Provisional Patent Application No. 62/408,677, filed Oct. 14, 2016, and U.S. Provisional Patent Application No. 62/456,105, filed Feb. 7, 2017, and U.S. Provisional Patent Application No. 62/480,496, filed Apr. 2, 2017. U.S. Ser. No. 15/722,434 is also a Continuation-In-Part of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015. U.S. Ser. No. 15/722,434 is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015. And U.S. Ser. No. 15/722,434 is also a Continuation-In-Part of U.S. application Ser. No. 15/284,528, filed Oct. 3, 2016, which claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

ACKNOWLEDGMENTS

Gil Thieberger would like to thank his holy and beloved teacher, Lama Dvora-hla, for her extraordinary teachings and manifestation of wisdom, love, compassion and morality, and for her endless efforts, support, and skills in guiding him and others on their paths to freedom and ultimate happiness. Gil would also like to thank his beloved parents for raising him exactly as they did.

BACKGROUND

Thermal measurements of the face can be utilized for various applications, which include detection of various physiological responses and/or medical conditions. However, when taken in uncontrolled real-life scenarios, thermal measurements can be influenced by various intrinsic and extrinsic factors. Some examples of such factors include infrared radiation directed at the face (e.g., sunlight), wind, physical contact with the face (e.g., touching the face with the hand), and consumption of substances such as various medications, alcohol, caffeine, and nicotine. Though these factors may be unrelated to a physiological response and/or medical condition being detected, they may nonetheless affect the temperatures at various regions of interest on the face. Therefore, these factors may be considered confounding factors that hinder the detection of the physiological response and/or medical condition. Thus, there is a need for systems that utilize thermal measurements collected in real-life scenarios to account for various intrinsic and/or extrinsic factors that may alter the thermal measurements, in order to avoid the detrimental effect that such factors may have on the utility of the thermal measurements for various applications.

SUMMARY

Collecting thermal measurements of various regions of a user's face can have many health-related (and other) applications, such as identifying various physiological responses of the user. However, the values of the measurements may be influenced, in some cases, by extrinsic factors, such as infrared radiation directed at the face (e.g., sunlight or a heater), which may affect the values of the measurements but are unrelated to the user's condition. Thus, such extrinsic factors can affect, in some cases, the accuracy of detections of physiological responses made based on thermal measurements. Some aspects of this disclosure describe systems and/or methods in which the effects of such extrinsic factors may be mitigated, which may improve the accuracy of detections of physiological responses made based on thermal measurements of the face.

One aspect of this disclosure involves a system configured to detect a physiological response. The system includes an inward-facing head-mounted thermal camera ($CAM_{in}$), an outward-facing head-mounted thermal camera ($CAM_{out}$), and a computer. $CAM_{in}$ takes thermal measurements of a region of interest ($TH_{ROI}$) on a user's face. $CAM_{in}$ does not occlude the region of interest (ROI) and is located less than 15 cm from the user's face. $CAM_{out}$ takes thermal measurements of the environment ($TH_{ENV}$) and is located less than 15 cm from the face. The computer detects the physiological response based on $TH_{ROI}$ and $TH_{ENV}$. Optionally, the system includes an eyeglasses frame that is worn on the user's head, and $CAM_{in}$ and $CAM_{out}$ each weigh below 5 g and are physically coupled to the frame. In one example, the ROI includes a region on the forehead of the user and the physiological response that is detected includes stress, a headache, and/or a stroke. In another example, the ROI includes a region on the nose of the user and the physiological response that is detected includes allergic reaction and/or stress.

In one embodiment, the computer generates feature values based on sets of $TH_{ROI}$ and $TH_{ENV}$, and utilizes a machine learning-based model to detect, based on the feature values, the physiological response. Optionally, responsive to receiving a first set of measurements in which $TH_{ROI}$ reaches a first threshold while $TH_{ENV}$ does not reach a second threshold, the computer detects the physiological response. Optionally, responsive to receiving a second set of measurements in which $TH_{ROI}$ reaches the first threshold while $TH_{ENV}$ reaches the second threshold, the computer does not detect the physiological response.

Another aspect of this disclosure involves a method for detecting a physiological response, which includes the following steps: In Step 1, taking thermal measurements of a region of interest ($TH_{ROI}$) on a user's face using an inward-facing head-mounted thermal camera ($CAM_{in}$). In Step 2, taking thermal measurements of the environment ($TH_{ENV}$) utilizing an outward-facing head-mounted thermal camera ($CAM_{out}$) worn by the user. In Step 3, generating feature values based on $TH_{ROI}$ and $TH_{ENV}$. And in Step 4, utilizing a machine learning-based model to detect the physiological response based on the feature values.

BRIEF DESCRIPTION OF THE DRAWINGS

The embodiments are herein described by way of example only, with reference to the following drawings:

FIG. 16a and FIG. 16b illustrate embodiments of right and left clip-on devices that are configured to be attached behind an eyeglasses frame;

FIG. 17a and FIG. 17b illustrate an embodiment of a single-unit clip-on device that is configured to be attached behind an eyeglasses frame;

FIG. 21a and FIG. 21b illustrate the making of different detections of emotional response based on thermal measurements compared to the emotional response that is visible in a facial expression;

FIG. 22 illustrates an embodiment of a smartphone app that provides a user with feedback about how he/she looks to others;

DETAILED DESCRIPTION

Figure 1A:
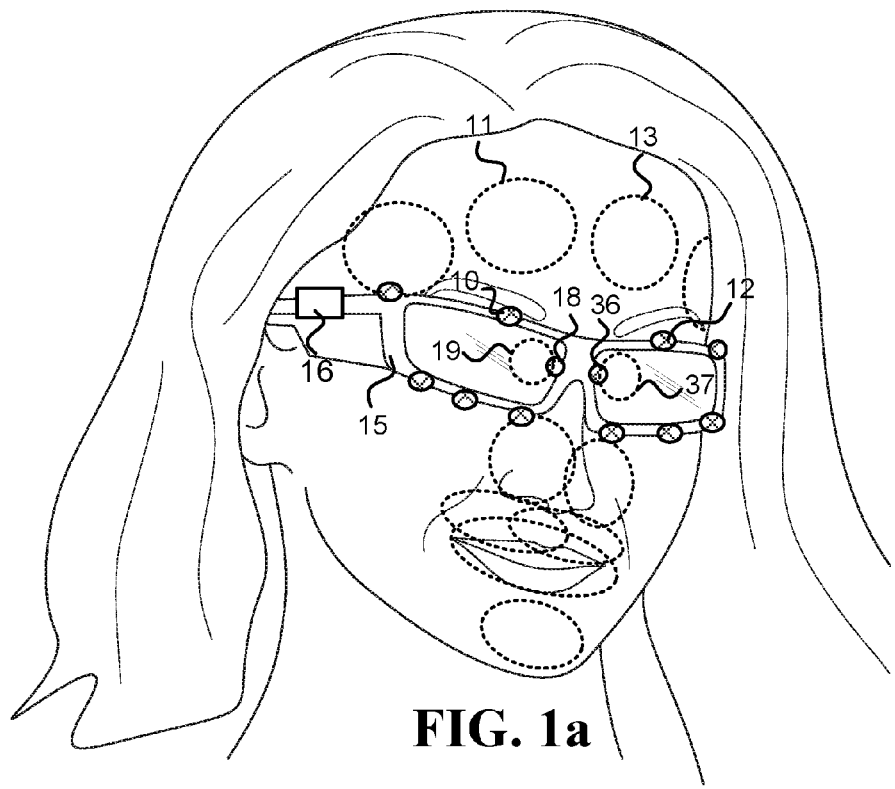
FIG. 1a and FIG. 1b illustrate various inward-facing head-mounted cameras coupled to an eyeglasses frame.

A "thermal camera" refers herein to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

Sentences in the form of "thermal measurements of an ROI" (usually denoted $TH_{ROI}$ or some variant thereof) refer to at least one of: (i) temperature measurements of the ROI ($T_{ROI}$), such as when using thermopile or microbolometer sensors, and (ii) temperature change measurements of the ROI ($\Delta T_{ROI}$), such as when using a pyroelectric sensor or when deriving the temperature changes from temperature measurements taken at different times by a thermopile sensor or a microbolometer sensor.

In some embodiments, a device, such as a thermal camera, may be positioned such that it occludes an ROI on the user's face, while in other embodiments, the device may be positioned such that it does not occlude the ROI. Sentences in the form of "the system/camera does not occlude the ROI" indicate that the ROI can be observed by a third person located in front of the user and looking at the ROI, such as illustrated by all the ROIs in FIG. 7, FIG. 11 and FIG. 19. Sentences in the form of "the system/camera occludes the ROI" indicate that some of the ROIs cannot be observed directly by that third person, such as ROIs 19 and 37 that are occluded by the lenses in FIG. 1a, and ROIs 97 and 102 that are occluded by cameras 91 and 96, respectively, in FIG. 9.

Although many of the disclosed embodiments can use occluding thermal cameras successfully, in certain scenarios, such as when using an HMS on a daily basis and/or in a normal day-to-day setting, using thermal cameras that do not occlude their ROIs on the face may provide one or more advantages to the user, to the HMS, and/or to the thermal cameras, which may relate to one or more of the following: esthetics, better ventilation of the face, reduced weight, simplicity to wear, and reduced likelihood to being tarnished.

A "Visible-light camera" refers to a non-contact device designed to detect at least some of the visible spectrum, such as a camera with optical lenses and CMOS or CCD sensor.

The term "inward-facing head-mounted camera" refers to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be attached to eyeglass using a clip-on mechanism (configured to be attached to and detached from the eyeglasses), or may be mounted to the user's head using any other known device that keeps the camera in a fixed position relative to the user's head also when the head moves. Sentences in the form of "camera physically coupled to the frame" mean that the camera moves with the frame, such as when the camera is fixed to (or integrated into) the frame, or when the camera is fixed to (or integrated into) an element that is physically coupled to the frame. The abbreviation "CAM" denotes "inward-facing head-mounted thermal camera", the abbreviation "$CAM_{out}$" denotes "outward-facing head-mounted thermal camera", the abbreviation "VCAM" denotes "inward-facing head-mounted visible-light camera", and the abbreviation "$VCAM_{out}$" denotes "outward-facing head-mounted visible-light camera".

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge; the frame in Oculus Rift™ includes the foam placed on the user's face and the straps; and the frames in Google Glass™ and Spectacles by Snap Inc. are similar to eyeglasses frames. Additionally or alternatively, the frame may connect to, be affixed within, and/or be integrated with, a helmet (e.g., sports, motorcycle, bicycle, and/or combat helmets) and/or a brainwave-measuring headset.

When a thermal camera is inward-facing and head-mounted, challenges faced by systems known in the art that are used to acquire thermal measurements, which include non-head-mounted thermal cameras, may be simplified and even eliminated with some of the embodiments described herein. Some of these challenges may involve dealing with complications caused by movements of the user, image registration, ROI alignment, tracking based on hot spots or markers, and motion compensation in the IR domain.

In various embodiments, cameras are located close to a user's face, such as at most 2 cm, 5 cm, 10 cm, 15 cm, or 20 cm from the face (herein "cm" denotes to centimeters). The distance from the face/head in sentences such as "a camera located less than 15 cm from the face/head" refers to the shortest possible distance between the camera and the face/head. The head-mounted cameras used in various embodiments may be lightweight, such that each camera weighs below 10 g, 5 g, 1 g, and/or 0.5 g (herein "g" denotes to grams).

Figure 1B:
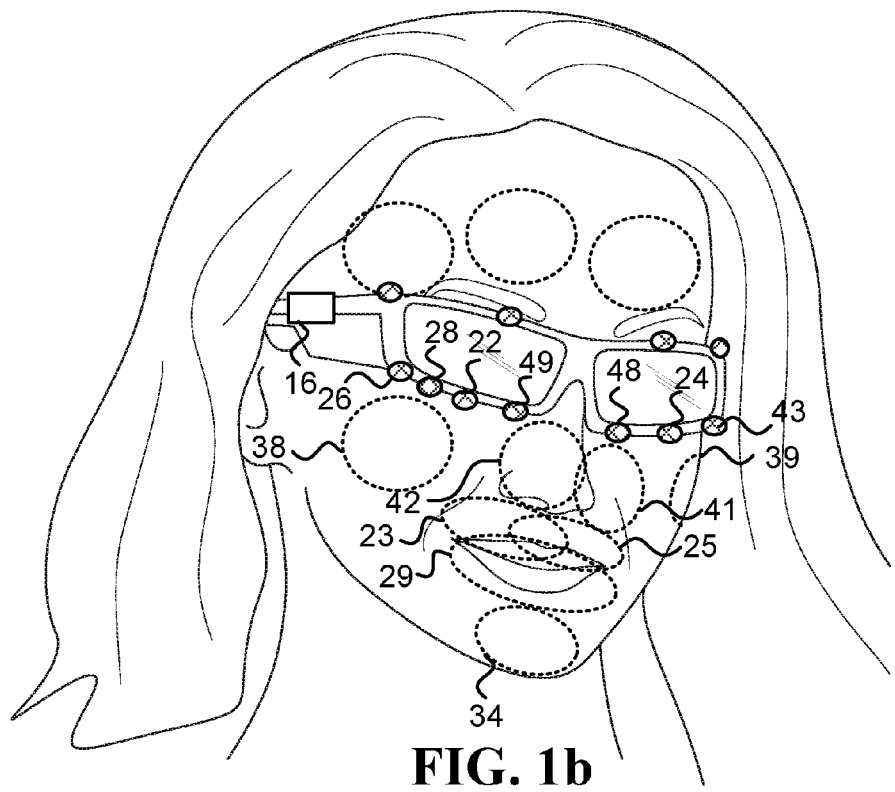

The following figures show various examples of HMSs equipped with head-mounted cameras. FIG. 1a illustrates various inward-facing head-mounted cameras coupled to an eyeglasses frame 15. Cameras 10 and 12 measure regions 11 and 13 on the forehead, respectively. Cameras 18 and 36 measure regions on the periorbital areas 19 and 37, respectively. The HMS further includes an optional computer 16, which may include a processor, memory, a battery and/or a communication module. FIG. 1b illustrates a similar HMS in which inward-facing head-mounted cameras 48 and 49 measure regions 41 and 41, respectively. Cameras 22 and 24 measure regions 23 and 25, respectively. Camera 28 measures region 29. And cameras 26 and 43 measure regions 38 and 39, respectively.

Figure 2:
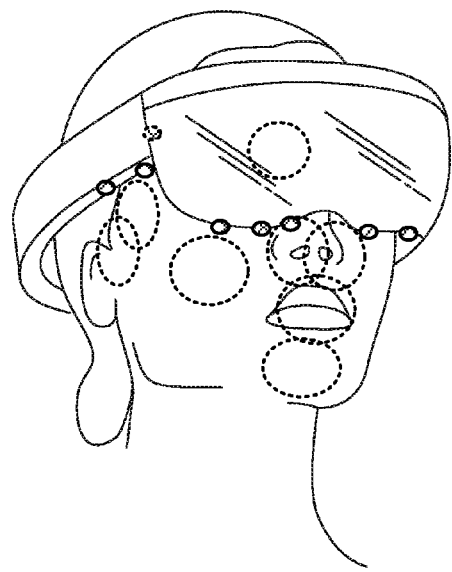
FIG. 2 illustrates inward-facing head-mounted cameras coupled to an augmented reality device.
Figure 3:
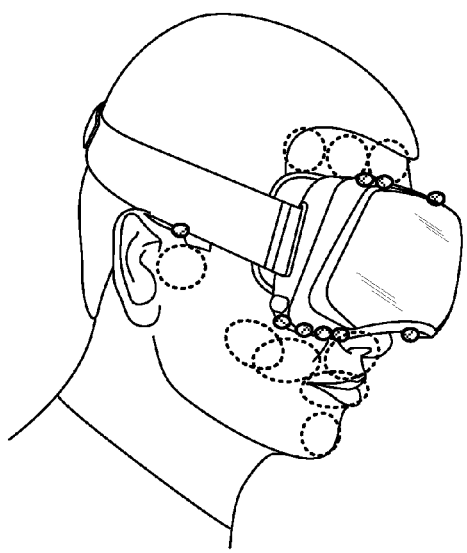
FIG. 3 illustrates head-mounted cameras coupled to a virtual reality device.
Figure 4:
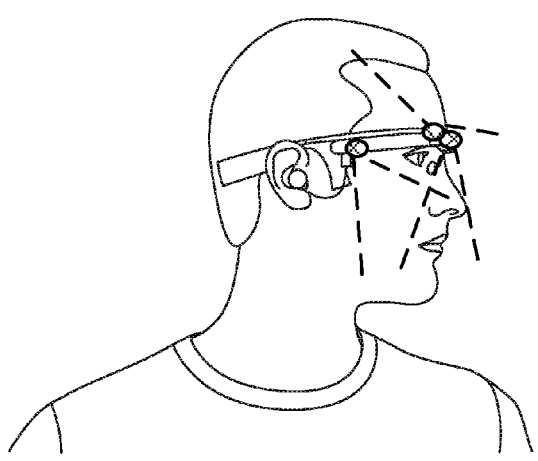
FIG. 4 illustrates a side view of head-mounted cameras coupled to an augmented reality device.
Figure 5:
FIG. 5 illustrates a side view of head-mounted cameras coupled to a sunglasses frame.

FIG. 2 illustrates inward-facing head-mounted cameras coupled to an augmented reality device such as Microsoft HoloLens™. FIG. 3 illustrates head-mounted cameras coupled to a virtual reality device such as Facebook's Oculus Rift™. FIG. 4 is a side view illustration of head-mounted cameras coupled to an augmented reality device such as Google Glass™. FIG. 5 is another side view illustration of head-mounted cameras coupled to a sunglasses frame.

Figure 6:
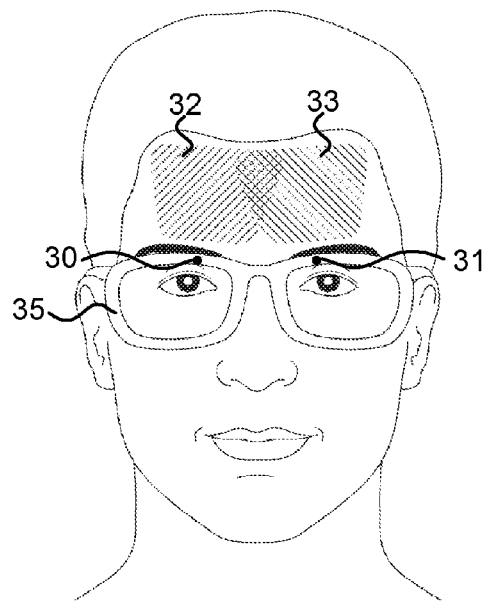
FIG. 6, FIG. 7, FIG. 8 and FIG. 9 illustrate head-mounted systems (HMSs) configured to measure various ROIs relevant to some of the embodiments describes herein.
Figure 7:
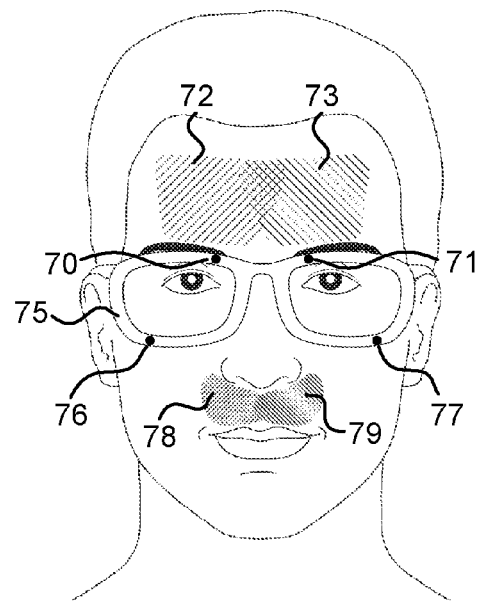
Figure 8:
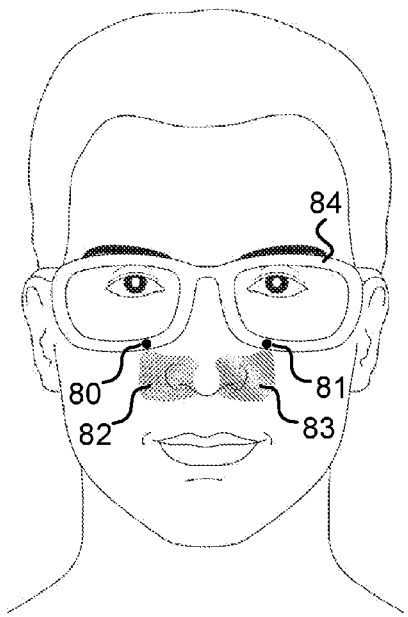
Figure 9:
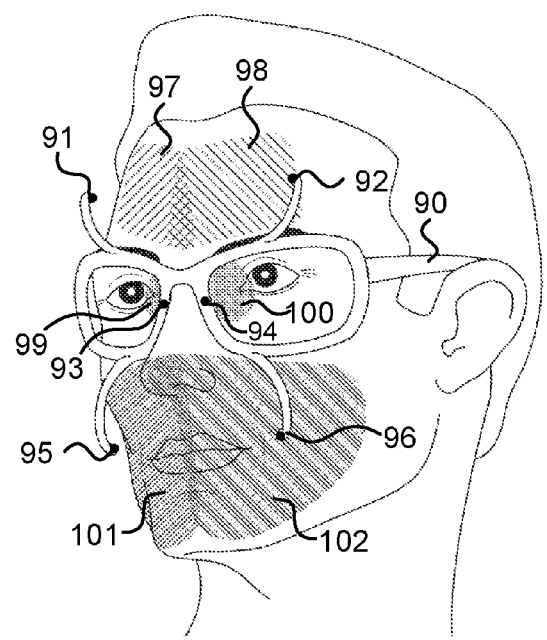

FIG. 6 to FIG. 9 illustrate HMSs configured to measure various ROIs relevant to some of the embodiments describes herein. FIG. 6 illustrates a frame 35 that mounts inward-facing head-mounted cameras 30 and 31 that measure regions 32 and 33 on the forehead, respectively. FIG. 7 illustrates a frame 75 that mounts inward-facing head-mounted cameras 70 and 71 that measure regions 72 and 73 on the forehead, respectively, and inward-facing head-mounted cameras 76 and 77 that measure regions 78 and 79 on the upper lip, respectively. FIG. 8 illustrates a frame 84 that mounts inward-facing head-mounted cameras 80 and 81 that measure regions 82 and 83 on the sides of the nose, respectively. And FIG. 9 illustrates a frame 90 that includes (i) inward-facing head-mounted cameras 91 and 92 that are mounted to protruding arms and measure regions 97 and 98 on the forehead, respectively, (ii) inward-facing head-mounted cameras 95 and 96, which are also mounted to protruding arms, which measure regions 101 and 102 on the lower part of the face, respectively, and (iii) head-mounted cameras 93 and 94 that measure regions on the periorbital areas 99 and 100, respectively.

Figure 10:
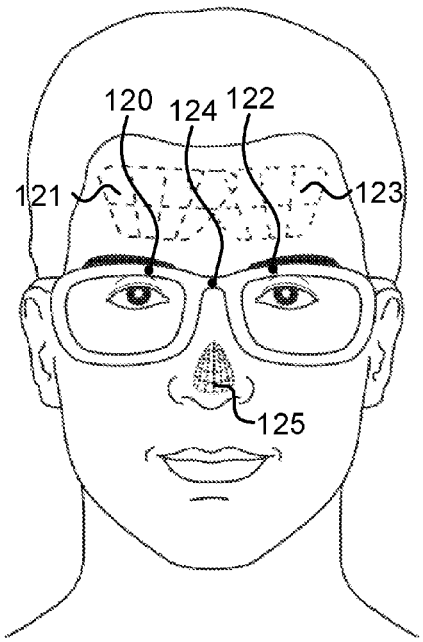
FIG. 10, FIG. 11, FIG. 12 and FIG. 13 illustrate various embodiments of systems that include inward-facing head-mounted cameras having multi-pixel sensors (FPA sensors)
Figure 11:
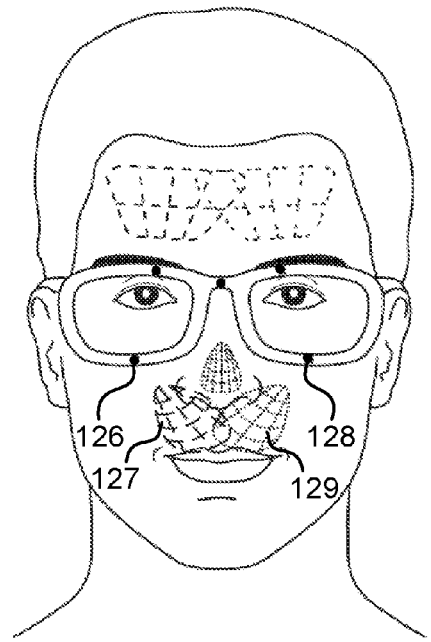
Figure 12:
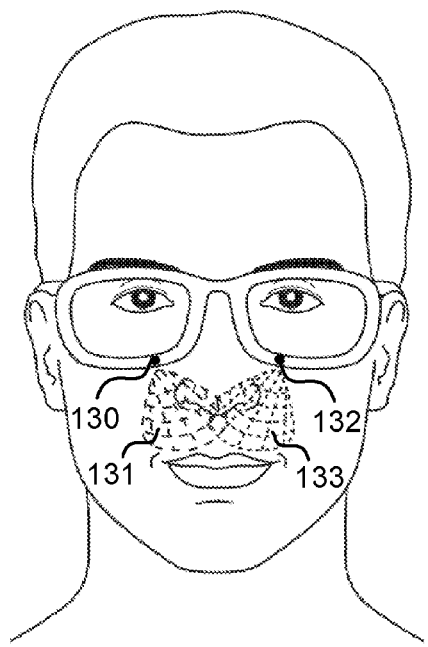
Figure 13:
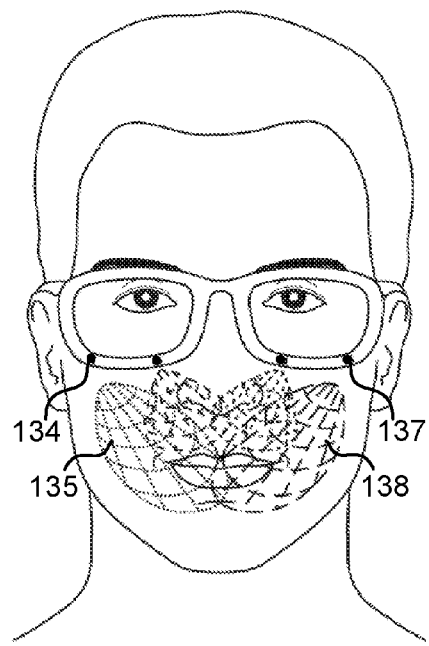

FIG. 10 to FIG. 13 illustrate various inward-facing head-mounted cameras having multi-pixel sensors (FPA sensors), configured to measure various ROIs relevant to some of the embodiments describes herein. FIG. 10 illustrates head-mounted cameras 120 and 122 that measure regions 121 and 123 on the forehead, respectively, and mounts head-mounted camera 124 that measure region 125 on the nose. FIG. 11 illustrates head-mounted cameras 126 and 128 that measure regions 127 and 129 on the upper lip, respectively, in addition to the head-mounted cameras already described in FIG. 10. FIG. 12 illustrates head-mounted cameras 130 and 132 that measure larger regions 131 and 133 on the upper lip and the sides of the nose, respectively. And FIG. 13 illustrates head-mounted cameras 134 and 137 that measure regions 135 and 138 on the right and left cheeks and right and left sides of the mouth, respectively, in addition to the head-mounted cameras already described in FIG. 12.

Figure 18:
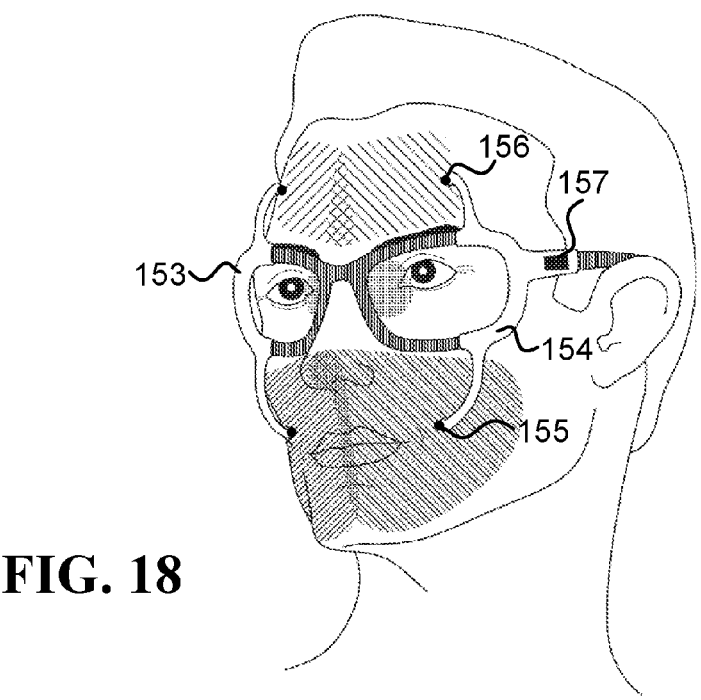
FIG. 18 illustrates embodiments of right and left clip-on devices, which are configured to be attached/detached from an eyeglasses frame, and have protruding arms to hold inward-facing head-mounted cameras.

In some embodiments, the head-mounted cameras may be physically coupled to the frame using a clip-on device configured to be attached/detached from a pair of eyeglasses in order to secure/release the device to/from the eyeglasses, multiple times. The clip-on device holds at least an inward-facing camera, a processor, a battery, and a wireless communication module. Most of the clip-on device may be located in front of the frame (as illustrated in FIG. 14b, FIG. 15b, and FIG. 18), or alternatively, most of the clip-on device may be located behind the frame, as illustrated in FIG. 16b and FIG. 17b.

Figure 14A:
FIG. 14a, FIG. 14b, and FIG. 14c illustrate embodiments of two right and left clip-on devices that are configured to attached/detached from an eyeglasses frame.
Figure 14B:
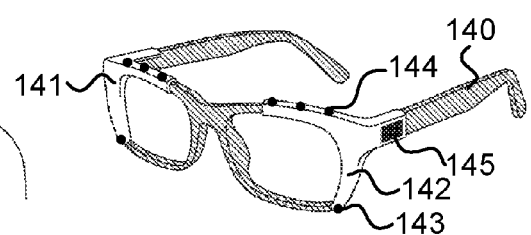
Figure 14C:
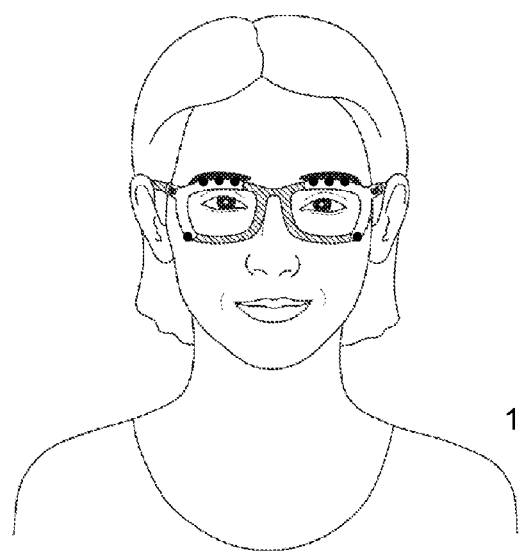

FIG. 14a, FIG. 14b, and FIG. 14c illustrate two right and left clip-on devices 141 and 142, respectively, configured to attached/detached from an eyeglasses frame 140. The clip-on device 142 includes an inward-facing head-mounted camera 143 pointed at a region on the lower part of the face (such as the upper lip, mouth, nose, and/or cheek), an inward-facing head-mounted camera 144 pointed at the forehead, and other electronics 145 (such as a processor, a battery, and/or a wireless communication module). The clip-on devices 141 and 142 may include additional cameras illustrated in the drawings as black circles.

Figure 15A:
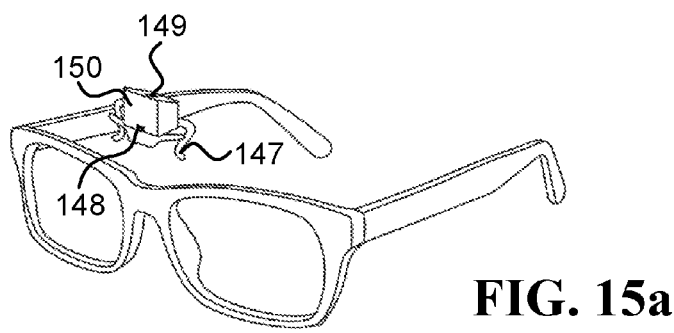
FIG. 15a and FIG. 15b illustrate an embodiment of a clip-on device that includes inward-facing head-mounted cameras pointed at the lower part of the face and the forehead.
Figure 15B:
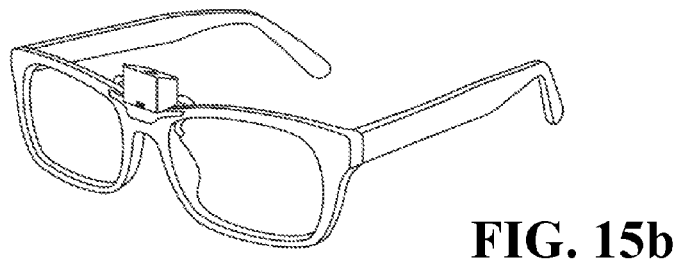

FIG. 15a and FIG. 15b illustrate a clip-on device 147 that includes an inward-facing head-mounted camera 148 pointed at a region on the lower part of the face (such as the nose), and an inward-facing head-mounted camera 149 pointed at the forehead. The other electronics (such as a processor, a battery, and/or a wireless communication module) is located inside the box 150, which also holds the cameras 148 and 149.

FIG. 16a and FIG. 16b illustrate two right and left clip-on devices 160 and 161, respectively, configured to be attached behind an eyeglasses frame 165. The clip-on device 160 includes an inward-facing head-mounted camera 162 pointed at a region on the lower part of the face (such as the upper lip, mouth, nose, and/or cheek), an inward-facing head-mounted camera 163 pointed at the forehead, and other electronics 164 (such as a processor, a battery, and/or a wireless communication module). The clip-on devices 160 and 161 may include additional cameras illustrated in the drawings as black circles.

FIG. 17a and FIG. 17b illustrate a single-unit clip-on device 170, configured to be attached behind an eyeglasses frame 176. The single-unit clip-on device 170 includes inward-facing head-mounted cameras 171 and 172 pointed at regions on the lower part of the face (such as the upper lip, mouth, nose, and/or cheek), inward-facing head-mounted cameras 173 and 174 pointed at the forehead, a spring 175 configured to apply force that holds the clip-on device 170 to the frame 176, and other electronics 177 (such as a processor, a battery, and/or a wireless communication module). The clip-on device 170 may include additional cameras illustrated in the drawings as black circles.

FIG. 18 illustrates two right and left clip-on devices 153 and 154, respectively, configured to attached/detached from an eyeglasses frame, and having protruding arms to hold the inward-facing head-mounted cameras. Head-mounted camera 155 measures a region on the lower part of the face, head-mounted camera 156 measures regions on the forehead, and the left clip-on device 154 further includes other electronics 157 (such as a processor, a battery, and/or a wireless communication module). The clip-on devices 153 and 154 may include additional cameras illustrated in the drawings as black circles.

It is noted that the elliptic and other shapes of the ROIs in some of the drawings are just for illustration purposes, and the actual shapes of the ROIs are usually not as illustrated. It is possible to calculate the accurate shape of an ROI using various methods, such as a computerized simulation using a 3D model of the face and a model of a head-mounted system (HMS) to which a thermal camera is physically coupled, or by placing a LED instead of the sensor (while maintaining the same field of view) and observing the illumination pattern on the face. Furthermore, illustrations and discussions of a camera represent one or more cameras, where each camera may have the same FOV and/or different FOVs. Unless indicated to the contrary, the cameras may include one or more sensing elements (pixels), even when multiple sensing elements do not explicitly appear in the figures; when a camera includes multiple sensing elements then the illustrated ROI usually refers to the total ROI captured by the camera, which is made of multiple regions that are respectively captured by the different sensing elements. The positions of the cameras in the figures are just for illustration, and the cameras may be placed at other positions on the HMS.

Sentences in the form of an "ROI on an area", such as ROI on the forehead or an ROI on the nose, refer to at least a portion of the area. Depending on the context, and especially when using a CAM having just one pixel or a small number of pixels, the ROI may cover another area (in addition to the area). For example, a sentence in the form of "an ROI on the nose" may refer to either: 100% of the ROI is on the nose, or some of the ROI is on the nose and some of the ROI is on the upper lip.

Various embodiments described herein involve detections of physiological responses based on user measurements. Some examples of physiological responses include stress, an allergic reaction, an asthma attack, a stroke, dehydration, intoxication, or a headache (which includes a migraine). Other examples of physiological responses include manifestations of fear, startle, sexual arousal, anxiety, joy, pain or guilt. Still other examples of physiological responses include physiological signals such as a heart rate or a value of a respiratory parameter of the user. Optionally, detecting a physiological response may involve one or more of the following: determining whether the user has/had the physiological response, identifying an imminent attack associated with the physiological response, and/or calculating the extent of the physiological response.

In some embodiments, detection of the physiological response is done by processing thermal measurements that fall within a certain window of time that characterizes the physiological response. For example, depending on the physiological response, the window may be five seconds long, thirty seconds long, two minutes long, five minutes long, fifteen minutes long, or one hour long. Detecting the physiological response may involve analysis of thermal measurements taken during multiple of the above-described windows, such as measurements taken during different days. In some embodiments, a computer may receive a stream of thermal measurements, taken while the user wears an HMS with coupled thermal cameras during the day, and periodically evaluate measurements that fall within a sliding window of a certain size.

In some embodiments, models are generated based on measurements taken over long periods. Sentences of the form of "measurements taken during different days" or "measurements taken over more than a week" are not limited to continuous measurements spanning the different days or over the week, respectively. For example, "measurements taken over more than a week" may be taken by eyeglasses equipped with thermal cameras, which are worn for more than a week, 8 hours a day. In this example, the user is not required to wear the eyeglasses while sleeping in order to take measurements over more than a week. Similarly, sentences of the form of "measurements taken over more than 5 days, at least 2 hours a day" refer to a set comprising at least 10 measurements taken over 5 different days, where at least two measurements are taken each day at times separated by at least two hours.

Utilizing measurements taken of a long period (e.g., measurements taken on "different days") may have an advantage, in some embodiments, of contributing to the generalizability of a trained model. Measurements taken over the long period likely include measurements taken in different environments and/or measurements taken while the measured user was in various physiological and/or mental states (e.g., before/after meals and/or while the measured user was sleepy/energetic/happy/depressed, etc.). Training a model on such data can improve the performance of systems that utilize the model in the diverse settings often encountered in real-world use (as opposed to controlled laboratory-like settings). Additionally, taking the measurements over the long period may have the advantage of enabling collection of a large amount of training data that is required for some machine learning approaches (e.g., "deep learning").

Detecting the physiological response may involve performing various types of calculations by a computer. Optionally, detecting the physiological response may involve performing one or more of the following operations: comparing thermal measurements to a threshold (when the threshold is reached that may be indicative of an occurrence of the physiological response), comparing thermal measurements to a reference time series, and/or by performing calculations that involve a model trained using machine learning methods. Optionally, the thermal measurements upon which the one or more operations are performed are taken during a window of time of a certain length, which may optionally depend on the type of physiological response being detected. In one example, the window may be shorter than one or more of the following durations: five seconds, fifteen seconds, one minute, five minutes, thirty minute, one hour, four hours, one day, or one week. In another example, the window may be longer than one or more of the aforementioned durations. Thus, when measurements are taken over a long period, such as measurements taken over a period of more than a week, detection of the physiological response at a certain time may be done based on a subset of the measurements that falls within a certain window near the certain time; the detection at the certain time does not necessarily involve utilizing all values collected throughout the long period.

In some embodiments, detecting the physiological response of a user may involve utilizing baseline thermal measurement values, most of which were taken when the user was not experiencing the physiological response. Optionally, detecting the physiological response may rely on observing a change to typical temperatures at one or more ROIs (the baseline), where different users might have different typical temperatures at the ROIs (i.e., different baselines). Optionally, detecting the physiological response may rely on observing a change to a baseline level, which is determined based on previous measurements taken during the preceding minutes and/or hours.

In some embodiments, detecting a physiological response involves determining the extent of the physiological response, which may be expressed in various ways that are indicative of the extent of the physiological response, such as: (i) a binary value indicative of whether the user experienced, and/or is experiencing, the physiological response, (ii) a numerical value indicative of the magnitude of the physiological response, (iii) a categorial value indicative of the severity/extent of the physiological response, (iv) an expected change in thermal measurements of an ROI (denoted $TH_{ROI}$ or some variation thereof), and/or (v) rate of change in $TH_{ROI}$. Optionally, when the physiological response corresponds to a physiological signal (e.g., a heart rate, a breathing rate, and an extent of frontal lobe brain activity), the extent of the physiological response may be interpreted as the value of the physiological signal.

One approach for detecting a physiological response, which may be utilized in some embodiments, involves comparing thermal measurements of one or more ROIs to a threshold. In these embodiments, the computer may detect the physiological response by comparing the thermal measurements, and/or values derived therefrom (e.g., a statistic of the measurements and/or a function of the measurements), to the threshold to determine whether it is reached. Optionally, the threshold may include a threshold in the time domain, a threshold in the frequency domain, an upper threshold, and/or a lower threshold. When a threshold involves a certain change to temperature, the certain change may be positive (increase in temperature) or negative (decrease in temperature). Different physiological responses described herein may involve different types of thresholds, which may be an upper threshold (where reaching the threshold means≥the threshold) or a lower threshold (where reaching the threshold means≤the threshold); for example, each physiological response may involve at least a certain degree of heating, or at least a certain degree cooling, at a certain ROI on the face.

Another approach for detecting a physiological response, which may be utilized in some embodiments, may be applicable when the thermal measurements of a user are treated as time series data. For example, the thermal measurements may include data indicative of temperatures at one or more ROIs at different points of time during a certain period. In some embodiments, the computer may compare thermal measurements (represented as a time series) to one or more reference time series that correspond to periods of time in which the physiological response occurred. Additionally or alternatively, the computer may compare the thermal measurements to other reference time series corresponding to times in which the physiological response did not occur. Optionally, if the similarity between the thermal measurements and a reference time series corresponding to a physiological response reaches a threshold, this is indicative of the fact that the thermal measurements correspond to a period of time during which the user had the physiological response. Optionally, if the similarity between the thermal measurements and a reference time series that does not correspond to a physiological response reaches another threshold, this is indicative of the fact that the thermal measurements correspond to a period of time in which the user did not have the physiological response. Time series analysis may involve various forms of processing involving segmenting data, aligning data, clustering, time warping, and various functions for determining similarity between sequences of time series data. Some of the techniques that may be utilized in various embodiments are described in Ding, Hui, et al. "Querying and mining of time series data: experimental comparison of representations and distance measures." Proceedings of the VLDB Endowment 1.2 (2008): 1542-1552, and in Wang, Xiaoyue, et al. "Experimental comparison of representation methods and distance measures for time series data." Data Mining and Knowledge Discovery 26.2 (2013): 275-309.

Herein, "machine learning" methods refers to learning from examples using one or more approaches. Optionally, the approaches may be considered supervised, semi-supervised, and/or unsupervised methods. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using machine learning methods. For brevity's sake, at times, a "machine learning-based model" may simply be called a "model". Referring to a model as being "machine learning-based" is intended to indicate that the model is trained using machine learning methods (otherwise, "model" may also refer to a model generated by methods other than machine learning).

In some embodiments, which involve utilizing a machine learning-based model, a computer is configured to detect the physiological response by generating feature values based on the thermal measurements (and possibly other values), and/or based on values derived therefrom (e.g., statistics of the measurements). The computer then utilizes the machine learning-based model to calculate, based on the feature values, a value that is indicative of whether, and/or to what extent, the user is experiencing (and/or is about to experience) the physiological response. Optionally, calculating said value is considered "detecting the physiological response". Optionally, the value calculated by the computer is indicative of the probability that the user has/had the physiological response.

Herein, feature values may be considered input to a computer that utilizes a model to perform the calculation of a value, such as the value indicative of the extent of the physiological response mentioned above. It is to be noted that the terms "feature" and "feature value" may be used interchangeably when the context of their use is clear. However, a "feature" typically refers to a certain type of value, and represents a property, while "feature value" is the value of the property with a certain instance (sample). For example, a feature may be temperature at a certain ROI, while the feature value corresponding to that feature may be 36.9° C. in one instance and 37.3° C. in another instance.

In some embodiments, a machine learning-based model used to detect a physiological response is trained based on data that includes samples. Each sample includes feature values and a label. The feature values may include various types of values. At least some of the feature values of a sample are generated based on measurements of a user taken during a certain period of time (e.g., thermal measurements taken during the certain period of time). Optionally, some of the feature values may be based on various other sources of information described herein. The label is indicative of a physiological response of the user corresponding to the certain period of time. Optionally, the label may be indicative of whether the physiological response occurred during the certain period and/or the extent of the physiological response during the certain period. Additionally or alternatively, the label may be indicative of how long the physiological response lasted. Labels of samples may be generated using various approaches, such as self-report by users, annotation by experts that analyze the training data, automatic annotation by a computer that analyzes the training data and/or analyzes additional data related to the training data, and/or utilizing additional sensors that provide data useful for generating the labels. It is to be noted that herein when it is stated that a model is trained based on certain measurements (e.g., "a model trained based on $TH_{ROI}$ taken on different days"), it means that the model was trained on samples comprising feature values generated based on the certain measurements and labels corresponding to the certain measurements. Optionally, a label corresponding to a measurement is indicative of the physiological response at the time the measurement was taken.

Various types of feature values may be generated based on thermal measurements. In one example, some feature values are indicative of temperatures at certain ROIs. In another example, other feature values may represent a temperature change at certain ROIs. The temperature changes may be with respect to a certain time and/or with respect to a different ROI. In order to better detect physiological responses that take some time to manifest, in some embodiments, some feature values may describe temperatures (or temperature changes) at a certain ROI at different points of time. Optionally, these feature values may include various functions and/or statistics of the thermal measurements such as minimum/maximum measurement values and/or average values during certain windows of time.

It is to be noted that when it is stated that feature values are generated based on data comprising multiple sources, it means that for each source, there is at least one feature value that is generated based on that source (and possibly other data). For example, stating that feature values are generated from thermal measurements of first and second ROIs ($TH_{ROI1}$ and $TH_{ROI2}$, respectively) means that the feature values may include a first feature value generated based on $TH_{ROI1}$ and a second feature value generated based on $TH_{ROI2}$. Optionally, a sample is considered generated based on measurements of a user (e.g., measurements comprising $TH_{ROI1}$ and $TH_{ROI2}$) when it includes feature values generated based on the measurements of the user.

In addition to feature values that are generated based on thermal measurements, in some embodiments, at least some feature values utilized by a computer (e.g., to detect a physiological response or train a mode) may be generated based on additional sources of data that may affect temperatures measured at various facial ROIs. Some examples of the additional sources include: (i) measurements of the environment such as temperature, humidity level, noise level, elevation, air quality, a wind speed, precipitation, and infrared radiation; (ii) contextual information such as the time of day (e.g., to account for effects of the circadian rhythm), day of month (e.g., to account for effects of the lunar rhythm), day in the year (e.g., to account for seasonal effects), and/or stage in a menstrual cycle; (iii) information about the user being measured such as sex, age, weight, height, and/or body build. Alternatively or additionally, at least some feature values may be generated based on physiological signals of the user obtained by sensors that are not thermal cameras, such as a visible-light camera, a photoplethysmogram (PPG) sensor, an electrocardiogram (ECG) sensor, an electroencephalography (EEG) sensor, a galvanic skin response (GSR) sensor, or a thermistor.

The machine learning-based model used to detect a physiological response may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects different conditions can have on the values of thermal measurements, and consequently, be able to achieve better detection of the physiological response in real world day-to-day scenarios.

Since real world day-to-day conditions are not the same all the time, sometimes detection of the physiological response may be hampered by what is referred to herein as "confounding factors". A confounding factor can be a cause of warming and/or cooling of certain regions of the face, which is unrelated to a physiological response being detected, and as such, may reduce the accuracy of the detection of the physiological response. Some examples of confounding factors include: (i) environmental phenomena such as direct sunlight, air conditioning, and/or wind; (ii) things that are on the user's face, which are not typically there and/or do not characterize the faces of most users (e.g., cosmetics, ointments, sweat, hair, facial hair, skin blemishes, acne, inflammation, piercings, body paint, and food leftovers); (iii) physical activity that may affect the user's heart rate, blood circulation, and/or blood distribution (e.g., walking, running, jumping, and/or bending over); (iv) consumption of substances to which the body has a physiological response that may involve changes to temperatures at various facial ROIs, such as various medications, alcohol, caffeine, tobacco, and/or certain types of food; and/or (v) disruptive facial movements (e.g., frowning, talking, eating, drinking, sneezing, and coughing).

Occurrences of confounding factors may not always be easily identified in thermal measurements. Thus, in some embodiments, systems may incorporate measures designed to accommodate for the confounding factors. In some embodiments, these measures may involve generating feature values that are based on additional sensors, other than the thermal cameras. In some embodiments, these measures may involve refraining from detecting the physiological response, which should be interpreted as refraining from providing an indication that the user has the physiological response. For example, if an occurrence of a certain confounding factor is identified, such as strong directional sunlight that heats one side of the face, the system may refrain from detecting that the user had a stroke. In this example, the user may not be alerted even though a temperature difference between symmetric ROIs on both sides of the face reaches a threshold that, under other circumstances, would warrant alerting the user.

Training data used to train a model for detecting a physiological response may include, in some embodiments, a diverse set of samples corresponding to various conditions, some of which involve occurrence of confounding factors (when there is no physiological response and/or when there is a physiological response). Having samples in which a confounding factor occurs (e.g., the user is in direct sunlight or touches the face) can lead to a model that is less susceptible to wrongfully detect the physiological response (which may be considered an occurrence of a false positive) in real world situations.

When a model is trained with training data comprising samples generated from measurements of multiple users, the model may be considered a general model. When a model is trained with training data comprising at least a certain proportion of samples generated from measurements of a certain user, and/or when the samples generated from the measurements of the certain user are associated with at least a certain proportion of weight in the training data, the model may be considered a personalized model for the certain user. Optionally, the personalized model for the certain user provides better results for the certain user, compared to a general model that was not personalized for the certain user. Optionally, personalized model may be trained based on measurements of the certain user, which were taken while the certain user was in different situations; for example, train the model based on measurements taken while the certain user had a headache/epilepsy/stress/anger attack, and while the certain user did not have said attack. Additionally or alternatively, the personalized model may be trained based on measurements of the certain user, which were taken over a duration long enough to span different situations; examples of such long enough durations may include: a week, a month, six months, a year, and three years.

Training a model that is personalized for a certain user may require collecting a sufficient number of training samples that are generated based on measurements of the certain user. Thus, initially detecting the physiological response with the certain user may be done utilizing a general model, which may be replaced by a personalized model for the certain user, as a sufficiently large number of samples are generated based on measurements of the certain user. Another approach involves gradually modifying a general model based on samples of the certain user in order to obtain the personalized model.

After a model is trained, the model may be provided for use by a system that detects the physiological response. Providing the model may involve performing different operations. In one embodiment, providing the model to the system involves forwarding the model to the system via a computer network and/or a shared computer storage medium (e.g., writing the model to a memory that may be accessed by the system that detects the physiological response). In another embodiment, providing the model to the system involves storing the model in a location from which the system can retrieve the model, such as a database and/or cloud-based storage from which the system may retrieve the model. In still another embodiment, providing the model involves notifying the system regarding the existence of the model and/or regarding an update to the model. Optionally, this notification includes information needed in order for the system to obtain the model.

A model for detecting a physiological response may include different types of parameters. Following are some examples of various possibilities for the model and the type of calculations that may be accordingly performed by a computer in order to detect the physiological response: (a) the model comprises parameters of a decision tree. Optionally, the computer simulates a traversal along a path in the decision tree, determining which branches to take based on the feature values. A value indicative of the physiological response may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of the physiological response; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer provides the feature values as inputs to the neural network, computes the values of the various activation functions and propagates values between layers, and obtains an output from the network, which is the value indicative of the physiological response.

A user interface (UI) may be utilized, in some embodiments, to notify the user and/or some other entity, such as a caregiver, about the physiological response and/or present an alert responsive to an indication that the extent of the physiological response reaches a threshold. The UI may include a screen to display the notification and/or alert, a speaker to play an audio notification, a tactile UI, and/or a vibrating UI. In some embodiments, "alerting" about a physiological response of a user refers to informing about one or more of the following: the occurrence of a physiological response that the user does not usually have (e.g., a stroke, intoxication, and/or dehydration), an imminent physiological response (e.g., an allergic reaction, an epilepsy attack, and/or a migraine), and an extent of the physiological response reaching a threshold (e.g., stress and/or anger reaching a predetermined level).

Figure 19:
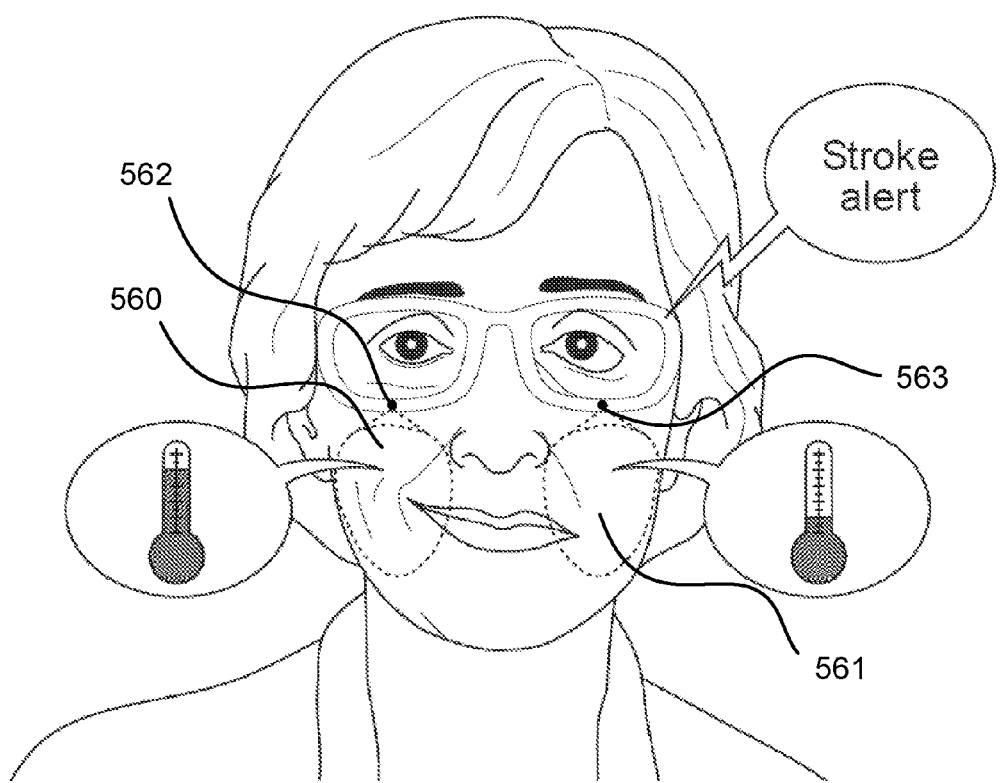
FIG. 19 illustrates a scenario in which an alert regarding a possible stroke is issued.

FIG. 19 illustrates a scenario in which an alert regarding a possible stroke is issued. The figure illustrates a user wearing a frame with at least two CAMs (562 and 563) for measuring ROIs on the right and left cheeks (ROIs 560 and 561, respectively). The measurements indicate that the left side of the face is colder than the right side of the face. Based on these measurements, and possibly additional data, the system detects the stroke and issues an alert. Optionally, the user's facial expression is slightly distorted and asymmetric, and a VCAM provides additional data in the form of images that may help detecting the stroke.

Various physiological responses may be detected based on thermal measurements and images of various regions of the face. In one embodiment, a system configured to detect a physiological response includes an inward-facing head-mounted thermal camera (CAM), an inward-facing head-mounted visible-light camera (VCAM), and a computer. The system may optionally include additional elements such as a frame and additional cameras.

CAM is worn on a user's head and takes thermal measurements of a first ROI ($TH_{ROI1}$) on the user's face. Optionally, CAM weighs below 10 g. Optionally, CAM is located less than 15 cm from the user's face. Optionally, CAM utilizes a microbolometer or a thermopile sensor. In one embodiment, CAM includes a focal-plane array (FPA) sensor and an infrared lens, and the FPA plane is tilted by more than 2° relative to the infrared lens plane according to the Scheimpflug principle in order to improve the sharpness of the image of $ROI_1$ (where the lens plane refers to a plane that is perpendicular to the optical axis of the lens, which may include one or more lenses).

VCAM is worn on the user's head and takes images of a second ROI ($IM_{ROI2}$) on the user's face. Optionally, VCAM weighs below 10 g and is located less than 15 cm from the face. Optionally, $ROI_1$ and $ROI_2$ overlap (which means extend over so as to cover at least partly). For example, $ROI_2$ may cover at least half of the area covered by $ROI_1$. In one embodiment, VCAM includes a multi-pixel sensor and a lens, and the sensor plane is tilted by more than 2° relative to the lens plane according to the Scheimpflug principle in order to improve the sharpness of the image of $ROI_2$.

It is to be noted that in some embodiments the system may be constructed in a way that none of the system's components (including the frame and cameras) occludes $ROI_1$ and/or $ROI_2$. In alternative embodiments, the system may be constructed in a way that at least some of the system components (e.g., the frame and/or CAM) may occlude $ROI_1$ and/or $ROI_2$.

The computer detects the physiological response based on $TH_{ROI1}$, $IM_{ROI2}$, and a model. Optionally, the model includes one or more thresholds to which $TH_{ROI1}$ and/or $IM_{ROI2}$ may be compared in order to detect the physiological response. Optionally, the model includes one or more reference time series to which $TH_{ROI1}$ and/or $IM_{ROI2}$ may be compared in order to detect the physiological response. Optionally, the computer detects the physiological response by generating feature values based on $TH_{ROI1}$ and $IM_{ROI2}$, and utilizing the model to calculate, based on the feature values, a value indicative of the extent of the physiological response. In this case, the model may be referred to as a "machine learning-based model". Optionally, at least some of the feature values, which are generated based on $IM_{ROI2}$ may be used to identify, and/or account for, various confounding factors that can alter $TH_{ROI1}$ without being directly related to the physiological response. Thus, on average, detections of the physiological responses based on $TH_{ROI1}$ and $IM_{ROI2}$ are more accurate than detections of the physiological responses based on $TH_{ROI1}$ without $IM_{ROI2}$.

In one example, the physiological response is indicative of an occurrence of at least one of the following emotional states of the user: joy, fear, sadness, and anger. In another example, the physiological response is indicative of an occurrence of one or more of the following: stress, mental workload, an allergic reaction, a headache, dehydration, intoxication, and a stroke. The physiological response may be a physiological signal of the user. In one example, the physiological response is a heart rate of the user, and in this example, $ROI_1$ is on the skin above at least one of the superficial temporal artery and the frontal superficial temporal artery. In another example, the physiological response is frontal lobe brain activity of the user, and in this example, $ROI_1$ is on the forehead. In still another example, the physiological signal is a breathing rate of the user, and $ROI_1$ is on the nasal area.

A machine learning-based model used to detect a physiological response is typically trained on samples, where each sample includes feature values generated based on $TH_{ROI1}$ and $IM_{ROI2}$ taken during a certain period, and a label indicative of the physiological response of the user during the certain period. Optionally, the model is trained on samples generated based on measurements of the user (in which case the model may be considered a personalized model of the user). Optionally, the model is trained on samples generated based on measurements of one or more other users. Optionally, the samples are generated based on measurements taken while the user being measured was in different situations. Optionally, the samples are generated based on measurements taken on different days.

In some embodiments, images such as $IM_{ROI2}$ may be utilized to generate various types of feature values, which may be utilized to detect the physiological response and/or detect an occurrence of a confounding factor. Some of the feature values generated based on images may include high-level facial-related feature values and their derivatives, such as location and dimensions of facial features and/or landmarks, identification of action units (AUs) in sequences of images, and/or blendshape weights. Other examples of features include various low-level features such as features generated using Gabor filters, local binary patterns (LBP) and their derivatives, algorithms such as SIFT and/or SURF (and their derivatives), image keypoints, histograms of oriented gradients (HOG) descriptors, and statistical procedures such independent component analysis (ICA), principal component analysis (PCA), or linear discriminant analysis (LDA). Yet other examples of feature values may include features derived from multiple images taken at different times, such as volume local binary patterns (VLBP), cuboids, and/or optical strain-based features. Additionally, some of the feature values may be based on other data, such as feature values generated based audio processing of data received from a head-mounted microphone. The audio processing may detect noises associated with talking, eating, and drinking, and convert it to feature values to be provided to the machine learning-based model.

Using both $TH_{ROI1}$ and $IM_{ROI2}$ to detect the physiological response may confer some advantages in some embodiments. For example, there may be times when $TH_{ROI1}$ and $IM_{ROI2}$ provide complementing signals of a physiological response (e.g., due to their ability to measure manifestations of different physiological processes related to the physiological response). This can increase the accuracy of the detections. In one embodiment, in which the physiological response being detected is an emotional response, the computer may identify facial expressions from $IM_{ROI2}$, and detect the emotional response of the user based on $TH_{ROI1}$ and the identified facial expressions. For example, at least some of the feature values generated based on $IM_{ROI2}$, which are used to detect the emotional response, are indicative of the facial expressions. Optionally, on average, detections of emotional responses based on both $TH_{ROI1}$ and the identified facial expressions are more accurate than detections of the emotional responses based on either $TH_{ROI1}$ or the identified facial expressions.

The following are some specific examples how $IM_{ROI2}$ may be utilized to help make detections of a physiological response more accurate. In one example, $ROI_1$ and $ROI_2$ are on the mouth, and $IM_{ROI2}$ are indicative of a change in a facial expression during a certain period that involves a transition from a facial expression in which the lips are in contact to a facial expression with an open mouth. Optionally, by utilizing $IM_{ROI2}$ to detect the physiological response based on $TH_{ROI1}$ taken during the certain period, the computer may be able attribute a change in $TH_{ROI1}$ to opening the mouth rather than a change in the temperature of the lips.

In another example, $ROI_1$ and $ROI_2$ are on the nose and upper lip, and $IM_{ROI2}$ are indicative of a change in a facial expression during a certain period that involves a transition from a neutral facial expression to a facial expression of disgust. Optionally, by utilizing $IM_{ROI2}$ to detect the physiological response based on $TH_{ROI1}$ taken during the certain period, the computer may be able attribute a change in $TH_{ROI1}$ to a raised upper lip and wrinkled nose instead of a change in the temperature of the nose and upper lip.

In yet another example, $ROI_1$ and $ROI_2$ are on the user's forehead located about 1 cm above at least one of the user's eyebrows, and $IM_{ROI2}$ are indicative of a change in a facial expression during a certain period that involves a transition from a neutral expression to a facial expression involving raised and/or lowered eyebrows (including middle-raised or middle-lowered eyebrows). Optionally, by utilizing $IM_{ROI2}$ to detect the physiological response based on $TH_{ROI1}$ taken during the certain period, the computer may be able attribute a change in $TH_{ROI1}$ to raising and/or lowering the eyebrows instead of a change in the temperature of the forehead.

It is to be noted that there are various approaches known in the art for identifying facial expressions from images. While many of these approaches were originally designed for full-face frontal images, those skilled in the art will recognize that algorithms designed for full-face frontal images may be easily adapted to be used with images obtained using the inward-facing head-mounted visible-light cameras disclosed herein. For example, the various machine learning techniques described in prior art references may be applied to feature values extracted from images that include portions of the face from orientations that are not directly in front of the user. Furthermore, due to the closeness of VCAM to the face, facial features are typically larger in images obtained by the systems described herein. Moreover, challenges such as image registration and face tracking are vastly simplified and possibly non-existent when using inward-facing head-mounted cameras. The reference Zeng, Zhihong, et al. "A survey of affect recognition methods: Audio, visual, and spontaneous expressions." *IEEE transactions on pattern analysis and machine intelligence* 31.1 (2009): 39-58, describes some of the algorithmic approaches that may be used for this task.

In some embodiments, $TH_{ROI1}$ and $IM_{ROI2}$ may provide different and even possibly contradicting indications regarding the physiological response. In particular, facial expressions may not always express how a user truly feels. For example, when in company of other people, a user may conceal his or her true feelings by making non-genuine facial expressions. However, at the same time, thermal measurements of the user's face may reveal the user's true emotions. Thus, a system that relies only on $IM_{ROI2}$ to determine the user's emotional response may be mistaken at times, and using $TH_{ROI1}$ can help make detections more accurate.

In one example, responsive to receiving a first set of $TH_{ROI1}$ and $IM_{ROI2}$ taken during a first period in which the user expressed a certain facial expression, the computer detects a first emotional response of the user. Additionally, responsive to receiving a second set of $TH_{ROI1}$ and $IM_{ROI2}$ taken during a second period in which the user expressed again the certain facial expression, the computer detects a second emotional response of the user, which is not the same as the first emotional response. The computer detected different emotional responses in this example because $TH_{ROI1}$ of the first set are indicative of a first physiological response, while $TH_{ROI1}$ of the second set are indicative of a second physiological response. Following are some more detailed examples of situations in which this may occur.

In one example, the first set includes $IM_{ROI2}$ indicative of a facial expression that is a smile and $TH_{ROI1}$ indicative of stress below a certain threshold, and the first emotional response detected by the computer is happiness. The second set in this example includes $IM_{ROI2}$ indicative of a facial expression that is a smile and $TH_{ROI1}$ indicative of stress above the certain threshold, and the second emotional response detected by the computer is discomfort.

In another example, the first set includes $IM_{ROI2}$ indicative of a facial expression that is a neutral expression and $TH_{ROI1}$ indicative of stress below a certain threshold, and the first emotional response detected by the computer is comfort. The second set includes $IM_{ROI2}$ indicative of a facial expression that is neutral and $TH_{ROI1}$ indicative of stress above the certain threshold, and the second emotional response detected by the computer is concealment.

In yet another example, the first set includes $IM_{ROI2}$ indicative of a facial expression that is an expression of anger and $TH_{ROI1}$ indicative of stress above a certain threshold, and the first emotional response detected by the computer is anger. The second set includes $IM_{ROI2}$ indicative of a facial expression that is an expression of anger and $TH_{ROI1}$ indicative of stress below the certain threshold, and the second emotional response detected by the computer is indicative of pretending to be angry.

The phenomenon of making different detections based on thermal measurements compared to the emotional response that is visible in a facial expression is illustrated in FIG. 21*a* and FIG. 21*b*. The illustrated figures include an HMS with CAM 514 and VCAM 515 that may cover portions of a cheek, mouth and/or nose. FIG. 21*a* illustrates a case in which the user's smiling face may be mistaken for happiness; however, the cold nose indicates that the user is in fact stressed. FIG. 21*b* illustrates a case in which the facial expression indicates that the user is in a neutral state; however, the warm nose indicates that the user is excited. FIG. 21*a* and FIG. 21*b* also illustrate a second CAM 516 and a second VCAM 517, which may be utilized in some embodiments, as described herein.

FIG. 22 illustrates one embodiment of a smartphone app that provides the user a feedback about how he/she looks to others. The illustrated app shows that the user was happy 96 time and angry 20 times. Because the purpose of this app is to measure how the user looks to others, the computer counts the facial expressions based on $IM_{ROI2}$ without correcting the facial expressions according $TH_{ROI1}$.

Figure 23:
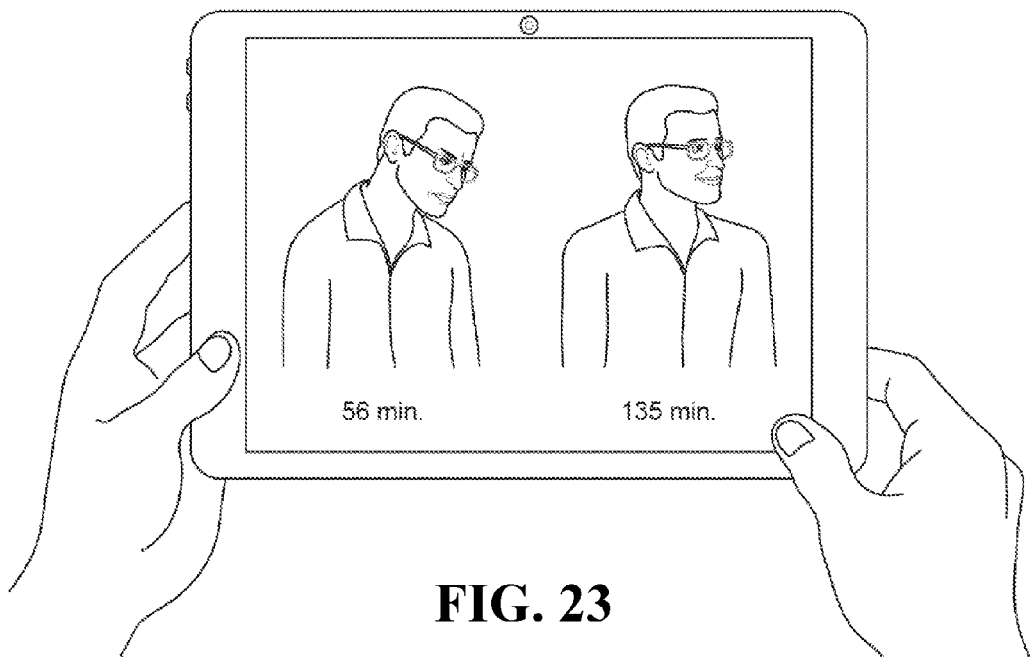
FIG. 23 illustrates one embodiment of a tablet app that provides the user a feedback about how he/she felt during a certain period.

FIG. 23 illustrates one embodiment of a tablet app that provides the user a feedback about how he/she felt during a certain period (e.g., during the day, the week, or while being at a certain location). The illustrated app shows that the user felt sad 56 minutes and happy 135 minutes. Because the purpose of this app is to measure how the user feels (and not just how the user looks to others), the computer determines the user's emotional state based on a combined analysis of $IM_{ROI2}$ and $TH_{ROI1}$, as exemplified above.

In one embodiment, the system may include a second inward-facing head-mounted thermal camera (CAM2) that takes thermal measurements of a third ROI ($TH_{ROI3}$) on the face. Optionally, CAM2 weighs below 10 g and is physically coupled to the frame. Optionally, the center of $ROI_1$ is to the right of the center of the third region of interest ($ROI_3$), and the symmetric overlapping between $ROI_1$ and $ROI_3$ is above 50%. Optionally, to detect the physiological response, the computer accounts for facial thermal asymmetry, based on a difference between $TH_{ROI1}$ and $TH_{ROI3}$.

It is noted that the symmetric overlapping is considered with respect to the vertical symmetry axis that divides the face to the right and left portions. The symmetric overlapping between $ROI_1$ and $ROI_3$ may be observed by comparing the overlap between $ROI_1$ and a mirror image of $ROI_3$, where the mirror image is with respect to a mirror that is perpendicular to the front of the face and whose intersection with the face is along the vertical symmetry axis (which goes through the middle of the forehead and the middle of the nose).

Some examples of calculations that may be performed by the computer to account for thermal asymmetry include: (i) utilizing different thresholds to which $TH_{ROI1}$ and $TH_{ROI3}$ are compared; (ii) utilizing different reference time series to which $TH_{ROI1}$ and $TH_{ROI3}$ are compared; (iii) utilizing a machine learning-based model that provides different results for first and second events that involve the same average change in $TH_{ROI1}$ and $TH_{ROI3}$ with different extents of asymmetry in $TH_{ROI1}$ and $TH_{ROI3}$; and (iv) utilizing the asymmetry for differentiating between (a) temperature changes in $TH_{ROI1}$ and $TH_{ROI3}$ that are related to the physiological response and (b) temperature changes in $TH_{ROI1}$ and $TH_{ROI3}$ that are unrelated to the physiological response.

In one embodiment, the system may include a second inward-facing head-mounted visible-light camera (VCAM2) that takes images of a third ROI ($IM_{ROI3}$) on the face. Optionally, VCAM2 weighs below 10 g and is physically coupled to the frame. Optionally, VCAM and VCAM2 are located at least 0.5 cm to the right and to the left of the vertical symmetry axis that divides the face, respectively, and the symmetric overlapping between $ROI_2$ and $ROI_3$ is above 50%. Optionally, the computer detects the physiological response also based on $IM_{ROI3}$. For example, the computer may generate some feature values based on $IM_{ROI3}$, which may be similar to feature values generated based on $IM_{ROI2}$, and utilizes the some feature values in the detection of the physiological response. In another example, the computer detects the physiological response based on the extent of symmetry between symmetric facial elements extracted from $IM_{ROI2}$ and $IM_{ROI3}$.

In some embodiments, $IM_{ROI2}$ may include recognizable facial skin color changes (FSCC). FSCC are typically a result of changes in the concentration levels of hemoglobin and blood oxygenation under a user's facial skin, and are discussed in more detail elsewhere in this disclosure. In one embodiment, the computer calculates, based on $IM_{ROI2}$, a value indicative of FSCC, and detects an emotional state of the user based on the calculated value. Optionally, on average, detections of the physiological response based on both $TH_{ROI1}$ and FSCC are more accurate than detections of the physiological response based on either $TH_{ROI1}$ or FSCC. In another embodiment, the computer generates feature values that are indicative of FSCC in $IM_{ROI2}$, and utilizes a model to detect the physiological response based on the feature values. Optionally, at least some of the feature values are generated based on $TH_{ROI1}$. Optionally, the model was trained based on samples, with each sample including feature values generated based on corresponding measurements of the user and a label indicative of the physiological response. Optionally, the label may be derived, for example, from analysis of the user's speech/writing, facial expression analysis, speech emotion analysis, and/or emotion extraction from analyzing galvanic skin response (GSR) and heart rate variability (HRV).

$IM_{ROI2}$ may be utilized, in some embodiments, to detect occurrences of confounding factors that can affect the temperature on the face, but are unrelated to the physiological response being detected. Thus, occurrences of confounding factors can reduce the accuracy of detections of the physiological response based on thermal measurements (such as based on $TH_{ROI1}$). Detecting occurrences of the confounding factors described below (cosmetics, sweat, hair, inflammation and touching) may be done utilizing various image-processing and/or image-analysis techniques known in the art. For example, detecting occurrences of at least some of the confounding factors described below may involve a machine learning algorithm trained to detect the confounding factors, and/or comparing $IM_{ROI2}$ to reference images that involve and do not involve the confounding factor (e.g., a first set of reference $IM_{ROI2}$ in which makeup was applied to the face and a second set of reference $IM_{ROI2}$ in which the face was bare of makeup).

The computer may utilize detection of confounding factors in various ways in order to improve the detection of the physiological response based on $TH_{ROI1}$. In one embodiment, the computer may refrain from making a detection of the physiological response responsive to identifying that the extent of a certain confounding factor reaches a threshold. For example, certain physiological responses may not be detected if there is extensive facial hair on the face or extensive skin inflammation. In another embodiment, the model used to detect the physiological response may include a certain feature that corresponds to a certain confounding factor, and the computer may generate a certain feature value indicative of the extent of the certain confounding factor. Optionally, the model in this case may be trained on samples in which the certain feature has different values, such as some of the samples used to train the model are generated based on measurements taken while the certain confounding factor occurred, and other samples used to train the model were generated based on measurements taken while the certain confounding factor did not occur. In yet another embodiment, the computer may weight measurements based on the occurrence of confounding factors, such that measurements taken while certain confounding factors occurred, may be given lower weights than measurements taken while the certain confounding factor did not occur. Optionally, lower weights for measurements mean that they have a smaller influence on the detection of the physiological response than measurements with higher weights. The following are some examples of confounding factors that may be detected, in some embodiments, based on $IM_{ROI2}$.

Some types of cosmetics (e.g., makeup and/or cream) may mask an ROI, affect the ROI's emissivity, and/or affect the ROI's temperature. Thus, taking into account cosmetics as a confounding factor may improve the system's ability to detect the physiological response. In one embodiment, the model was trained on: samples generated based on a first set of $TH_{ROI1}$ and $IM_{ROI2}$ taken after cosmetics were applied to a portion of the overlapping region between $ROI_1$ and $ROI_2$, and other samples generated based on a second set of $TH_{ROI1}$ and $IM_{ROI2}$ taken while the overlapping region was bare of cosmetics. Optionally, utilizing this model may enable the computer to account for presence of cosmetics on a portion of $ROI_2$.

Sweating may affect the ROI's emissivity. Thus, taking into account sweating as a confounding factor may improve the system's ability to detect the physiological response. In one embodiment, the model was trained on: samples generated from a first set of $TH_{ROI1}$ and $IM_{ROI2}$ taken while sweat was detectable on a portion of the overlapping region between ROI1 and ROI2, and additional samples generated from a second set of $TH_{ROI1}$ and $IM_{ROI2}$ taken while sweat was not detectable on the overlapping region. Optionally, utilizing this model may enable the computer to account for sweat on the overlapping region.

Dense hair may affect the ROI's emissivity, which may make the ROI appear, in thermal imaging, colder than it really is. Thus, taking into account hair density and/or hair length (both referred to as hair density) as a confounding factor may improve the system's ability to detect the physiological response. In one embodiment, the model was trained on: samples generated from a first set of $TH_{ROI1}$ and $IM_{ROI2}$ taken while hair density on a portion of the overlapping region between $ROI_1$ and $ROI_2$ was at a first level, and additional samples generated from a second set of $TH_{ROI1}$ and $IM_{ROI2}$ taken while hair density on the portion of the overlapping region between $ROI_1$ and $ROI_2$ was at a second level higher than the first level. Optionally, utilizing a model trained so may enable the computer to account for hair on the overlapping region.

Figure 27A:
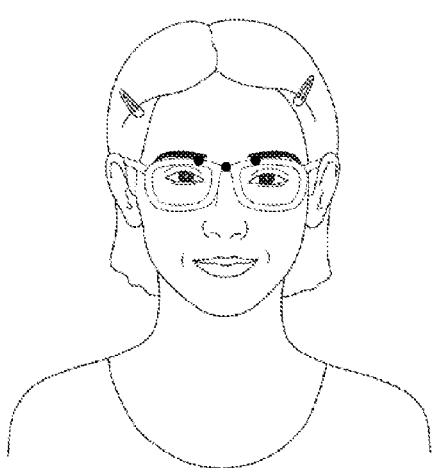
FIG. 27a illustrates a first case where a user's hair does not occlude the forehead.
Figure 27B:
FIG. 27b illustrates a second case where a user's hair occludes the forehead and the system requests the user to move the hair in order to enable correct measurements of the forehead.

In another embodiment, when the hair can be moved the system may request the user to move her hair in order to enable the thermal cameras to take correct measurements. For example, FIG. 27a illustrates a first case where the user's hair does not occlude the forehead. FIG. 27b illustrates a second case where the user's hair does occlude the forehead and thus the system requests the user to move the hair in order to enable correct measurements of the forehead.

Figure 25A:
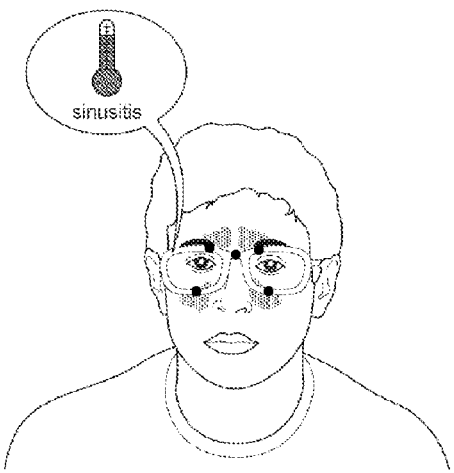
FIG. 25a and FIG. 25b illustrate heating of a ROI for different reasons: sinusitis (which is detected), and acne (which is not detected as sinusitis)
Figure 25B:
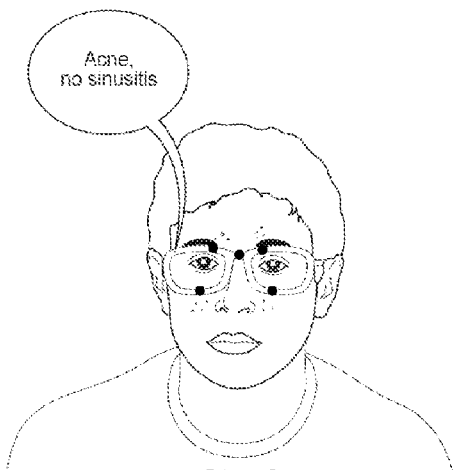

Skin inflammations (which may include skin blemishes, acne, and/or inflammatory skin diseases) usually increases ROI temperature in a manner that is unrelated to the physiological response being detected. Thus, taking into account skin inflammation as a confounding factor may improve the system's ability to detect the physiological response. FIG. 25a illustrates heating of the ROI because of sinusitis, for which the system detects the physiological response (sinusitis). On the other hand, FIG. 25b illustrates heating of the same ROI because of acne, for which the system does detect sinusitis. In one embodiment, the model was trained on: samples generated from a first set of $TH_{ROI1}$ and $IM_{ROI2}$ taken while skin inflammation was detectable on a portion of the overlapping region between $ROI_1$ and $ROI_2$, and additional samples generated from a second set of $TH_{ROI1}$ and $IM_{ROI2}$ taken while skin inflammation was not detectable on the overlapping region. Optionally, utilizing a model trained so may enable the computer to account for skin inflammation on the overlapping region.

Touching the ROI may affect $TH_{ROI}$ by increasing or decreasing the temperature at the touched region. Thus, touching the ROI may be considered a confounding factor that can make detections of the physiological response less accurate. In one embodiment, the model was trained on: samples generated from a first set of $TH_{ROI1}$ and $IM_{ROI2}$ taken while detecting that the user touches a portion of the overlapping region between $ROI_1$ and $ROI_2$, and additional samples generated from a second set of $TH_{ROI1}$ and $IM_{ROI2}$ taken while detecting that the user does not touch the overlapping region. Optionally, utilizing a model trained so may enables the computer to account for touching the overlapping region.

Throughout day-to-day activities, a user may make various facial movements that are unrelated to the physiological response being detected, and thus can negatively affect the thermal measurements taken by CAM. This can lead to measurements that may be incorrectly attributed to the physiological response. To address this issue, the computer may identify disruptive activities, such as talking, eating, and drinking, and utilize the identified disruptive activities in order to more accurately detect the physiological response. In one embodiment, the computer utilizes a machine learning-based approach to handle the disruptive activities. This approach may include (i) identifying, based on $IM_{ROI2}$, occurrences of one or more of the disruptive activities, (ii) generating feature values based on the identified disruptive activities, and (iii) utilizing a machine learning-based model to detect the physiological response based on the feature values and feature values generated from $TH_{ROI1}$.

In addition to detecting a physiological response, in some embodiments, the computer may utilize $IM_{ROI2}$ to generate an avatar of the user (e.g., in order to represent the user in a virtual environment). Optionally, the avatar may express emotional responses of the user, which are detected based on $IM_{ROI2}$. Optionally, the computer may modify the avatar to show synthesized facial expressions that are not manifested in the user's actual facial expressions, but the synthesized facial expressions correspond to emotional responses detected based on $TH_{ROI1}$. Some of the various approaches that may be utilized to generate the avatar based on $IM_{ROI2}$ are described in co-pending US patent publication 2016/0360970.

Contraction and relaxation of various facial muscles can cause facial tissue to slightly change its position and/or shape. Thus, facial movements can involve certain movements to ROIs. With thermal cameras that have multiple sensing elements (pixels), this can cause the ROI to move and be covered by various subsets of pixels as the user's face moves (e.g., due to talking/or making facial expressions). For example, smiling can cause the user's cheeks to move upwards. This can cause a thermal camera that covers a cheek to capture an ROI located on a cheek with a first set of pixels (from among the camera's pixels) when the user has a neutral expression, and to capture images of the ROI with a second set of pixels, when the user is smiling. In this example, on average, the pixels in the second set are likely to be located higher in the images than the pixels in the first set. To account for the possible movement of ROIs due to facial expressions, the computer may track locations of one or more facial landmarks in a series of $IM_{ROI2}$, and utilize the locations to adjust $TH_{ROI1}$. Facial landmarks are usually the most salient facial points on the face.

In one embodiment in which CAM comprises multiple sensing elements, which correspond to values of multiple pixels in $TH_{ROI1}$, the computer may assign weights to the multiple pixels based on the locations of the one or more facial landmarks, which are determined based on $IM_{ROI2}$. Assigning weights to pixels based on their location with respect to a facial landmark can be considered a form of selection of the pixels that cover the ROI based on the location of the landmark. In one example, the weights are assigned based on a function that takes into account the distance of each pixel from the locations of one or more facial landmarks and/or the relative position of each pixel with respect to the locations.

In another embodiment, the computer may generate certain feature values based on locations of one or more landmarks, which are determined based on analysis of $IM_{ROI2}$. These certain feature values may be utilized in conjunction with other feature values (e.g., feature values generated based on $TH_{ROI1}$) to detect the physiological response using a machine learning-based model.

The following is a description of a method for detecting a physiological response based on measurements from CAM and VCAM. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, taking thermal measurements of a first ROI ($TH_{ROI1}$) on the user's face using an inward-facing head-mounted thermal camera located at most 15 cm from the user's face. In Step 2, taking images of a second ROI ($IM_{ROI2}$) on the user's face with an inward-facing head-mounted visible-light camera located at most 15 cm from the user's face. Optionally, the first ROI ($ROI_1$) and the second ROI ($ROI_2$) overlap. In Step 3, generating feature values based on $TH_{ROI1}$ and $IM_{ROI2}$. And in Step 4, utilizing a model to detect the physiological response based on the feature values. Optionally, the model was trained based on previous $TH_{ROI1}$ and $IM_{ROI2}$ taken on different days.

In one embodiment, the physiological response is an emotional response, and the method optionally includes the following steps: calculating, based on $IM_{ROI2}$, a value indicative of facial skin color changes (FSCC), and utilizing the value indicative of FSCC to generate at least one of the feature values used to detect the physiological response in Step 4.

In another embodiment, generating the feature values in Step 3 involves generating, based on $IM_{ROI2}$, feature values indicative of an occurrence of one or more of the following confounding factors on a portion of the overlapping region between $ROI_1$ and $ROI_2$: a presence of cosmetics, a presence of sweat, a presence of hair, and a presence of skin inflammation.

The following is a description of a system that detects a physiological response based on an inward-facing head-mounted thermal camera ($CAM_{in}$), an outward-facing head-mounted thermal camera ($CAM_{out}$), and a computer. $CAM_{out}$ measures the environment and generates data indicative of confounding factors, such as direct sunlight or air conditioning. Accounting for confounding factors enables the system to more accurately detect the physiological response compared to a system that does not account for these confounding factors. Optionally, $CAM_{in}$ and/or $CAM_{out}$ are physically coupled to a frame worn on a user's head, such as a frame of a pair of eyeglasses or an augmented reality device. Optionally, each of $CAM_{in}$ and $CAM_{out}$ weighs below 5 g and is located less than 15 cm from the user's face.

$CAM_{in}$ takes thermal measurements of an ROI ($TH_{ROI}$) on the user's face. Optionally, $CAM_{in}$ does not occlude the ROI. In one example, the ROI includes a region on the forehead and the physiological response involves stress, a headache, and/or a stroke. In another example, the ROI includes a region on the nose and the physiological response is an allergic reaction.

$CAM_{out}$ takes thermal measurements of the environment ($TH_{ENV}$). Optionally, $CAM_{out}$ does not occlude the ROI. Optionally, the angle between the optical axes of $CAM_{in}$ and $CAM_{out}$ is at least 45°, 90°, 130°, 170°, or 180°. Optionally, the field of view (FOV) of $CAM_{in}$ is larger than the FOV of $CAM_{out}$ and/or the noise equivalent differential temperature (NEDT) of $CAM_{in}$ is lower than NEDT of $CAM_{out}$. In one example, $CAM_{in}$ has a FOV smaller than 80° and $CAM_{out}$ has a FOV larger than 80°. In another example, $CAM_{in}$ has more sensing elements than $CAM_{out}$ (e.g., $CAM_{in}$ has at least double the number of pixels as $CAM_{out}$).

In one embodiment, $CAM_{in}$ and $CAM_{out}$ are based on sensors of the same type with similar operating parameters. Optionally, $CAM_{in}$ and $CAM_{out}$ are located less than 5 cm or 1 cm apart. Having sensors of the same type, which are located near each other, may have an advantage of having both $CAM_{in}$ and $CAM_{out}$ be subject to similar inaccuracies resulting from heat conductance and package temperature. In another embodiment, $CAM_{in}$ and $CAM_{out}$ may be based on sensors of different types, with different operating parameters. For example, $CAM_{in}$ may be based on a microbolometer FPA while $CAM_{out}$ may be based on a thermopile (that may be significantly less expensive than the microbolometer).

Figure 28A:
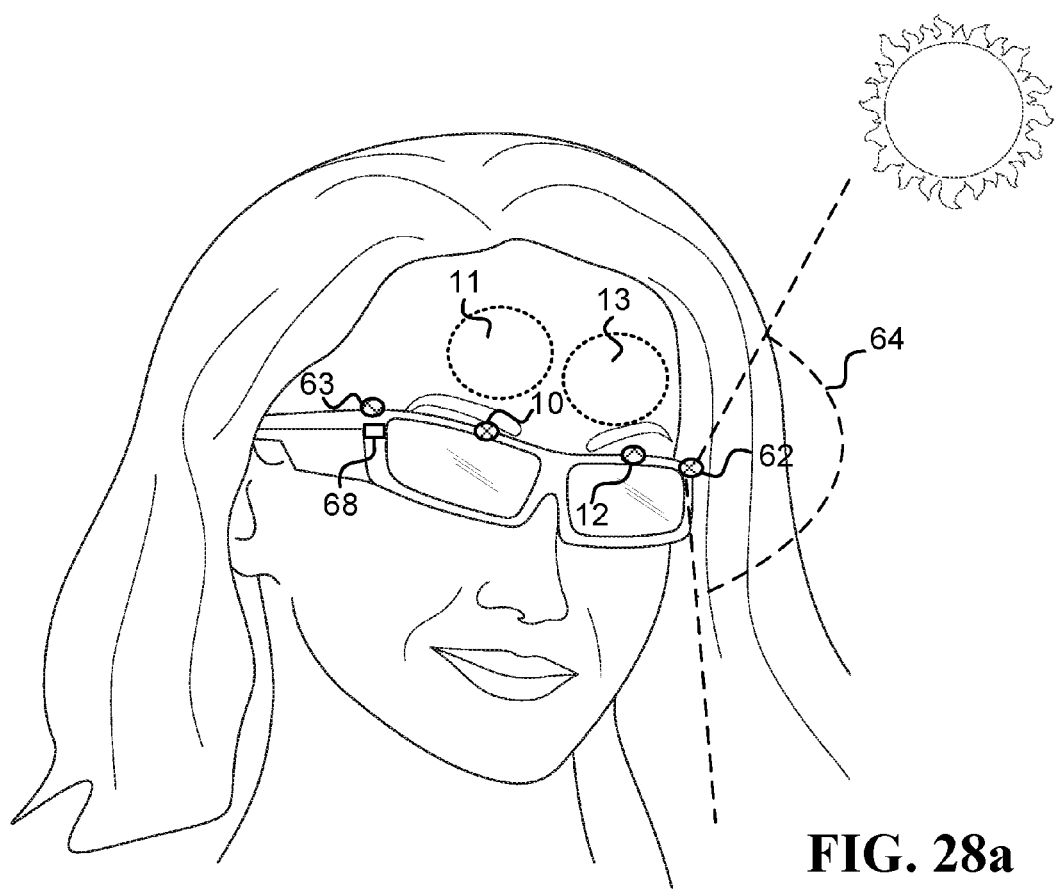
FIG. 28a illustrates an embodiment of a system that detects a physiological response based on measurements taken by an inward-facing head-mounted thermal camera and an outward-facing head-mounted thermal camera.
Figure 28B:
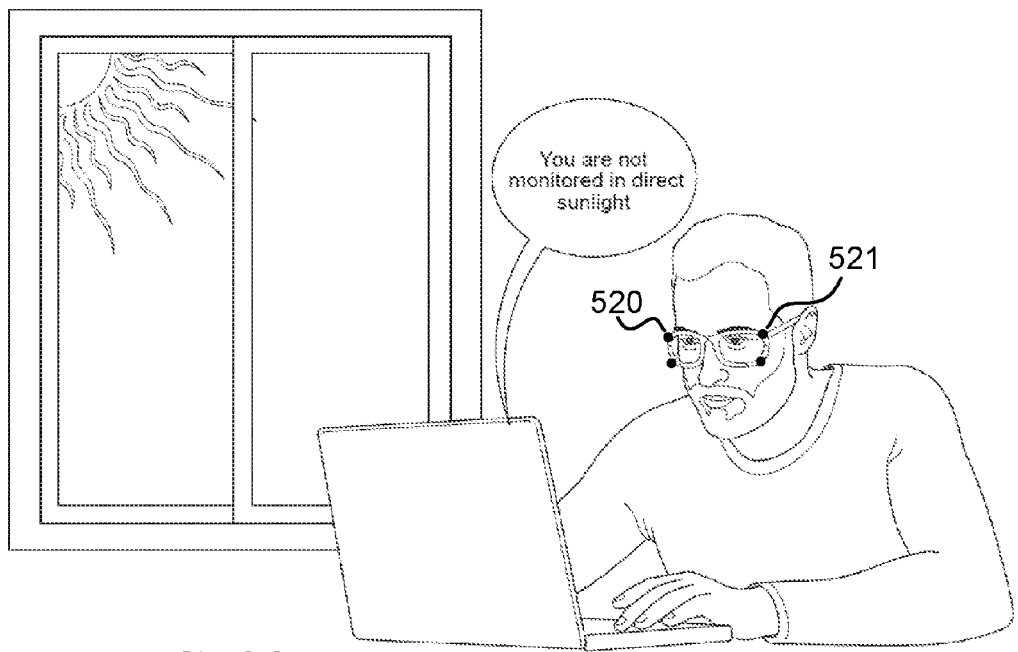
FIG. 28b illustrates a scenario in which a user receives an indication on a GUI that the user is not monitored in direct sunlight.

FIG. 28a illustrates one embodiment of the system that includes inward-facing and outward-facing head-mounted thermal cameras on both sides of the frame. In this illustration, $CAM_{in}$ is the inward-facing thermal camera 12, which takes thermal measurements of ROI 13, and $CAM_{out}$ is the outward-facing thermal camera 62. Arc 64 illustrates the larger FOV of $CAM_{out}$ 62, compared to the FOV of $CAM_{in}$ that covers ROI 13. The illustrated embodiment includes a second head-mounted thermal camera 10 ($CAM_{in2}$) on the right side of the frame, which takes thermal measurements of ROI 11, and a second outward-facing head-mounted thermal camera 63 ($CAM_{out2}$). FIG. 28b illustrates receiving an indication on a GUI (on the illustrated laptop) that the user is not monitored in direct sunlight. Cameras 520 and 521 are the outward-facing head-mounted thermal cameras.

The computer detects a physiological response based on $TH_{ROI}$ and $TH_{ENV}$. Optionally, $TH_{ENV}$ are utilized to account for at least some of the effect of heat transferred from the environment to the ROI (and not due to the user's physiological response). Thus, on average, detections of the physiological response based on $TH_{ROI}$ and $TH_{ENV}$ may be more accurate than detections of the physiological response based on $TH_{ROI}$ without $TH_{ENV}$.

There are various ways in which the computer may utilize $TH_{ENV}$ to increase the accuracy of detecting the physiological response. In one embodiment, the computer generates feature values based on a set of $TH_{ROI}$ and $TH_{ENV}$, and utilizes a machine learning-based model to detect, based on the feature values, the physiological response. By utilizing $TH_{ENV}$ to generate one or more of the feature values, the computer may make different detections of the physiological response based on similar $TH_{ROI}$ that are taken in dissimilar environments. For example, responsive to receiving a first set of measurements in which $TH_{ROI}$ reaches a first threshold while $TH_{ENV}$ does not reach a second threshold, the computer detects the physiological response. However, responsive to receiving a second set of measurements in which $TH_{ROI}$ reaches the first threshold while $TH_{ENV}$ reaches the second threshold, the computer does not detect the physiological response. Optionally, $TH_{ENV}$ reaching the second threshold indicates that the user was exposed to high infrared radiation that is expected to interfere with the detection.

In another embodiment, the computer may utilize $TH_{ENV}$ for the selection of values that are appropriate for the detection of the physiological response. In one example, the computer may select different thresholds (to which $TH_{ROI}$ are compared) for detecting the physiological response. In this example, different $TH_{ENV}$ may cause the computer to use different thresholds. In another example, the computer may utilize $TH_{ENV}$ to select an appropriate reference time series (to which $TH_{ROI}$ may be compared) for detecting the physiological response. In yet another example, the computer may utilize $TH_{ENV}$ to select an appropriate model to utilize to detect the physiological response based on the feature values generated based on $TH_{ROI}$.

In still another embodiment, the computer may normalize $TH_{ROI}$ based on $TH_{ENV}$. In one example, the normalization may involve subtracting a value proportional to $TH_{ENV}$ from $TH_{ROI}$, such that the value of the temperature at the ROI is adjusted based on the temperature of the environment at that time and/or in temporal proximity to that time (e.g., using an average of the environment temperature during the preceding minute). Additionally or alternatively, the computer may adjust weights associated with at least some $TH_{ROI}$ based on $TH_{ENV}$, such that the weight of measurements from among $TH_{ROI}$ that were taken during times the measurements of the environment indicated extreme environmental temperatures is reduced.

In yet another embodiment, responsive to determining that $TH_{ENV}$ represent an extreme temperature (e.g., lower than 5° C., higher than 35° C., or some other ranges deemed inappropriate temperatures), the computer may refrain from performing detection of the physiological response. This way, the computer can avoid making a prediction that is at high risk of being wrong due to the influence of the extreme environmental temperatures. In a similar manner, instead of determining that $TH_{ENV}$ represent an extreme temperature, the computer may determine that the difference between $TH_{ROI}$ and $TH_{ENV}$ are not in an acceptable range (e.g., there is a difference of more than 15° C. between the two), and refrain from making a detection of the physiological response in that event.

The following examples describe ways to use $TH_{ENV}$ to detect the physiological response based on $TH_{ROI}$. In one example, the computer detects the physiological response based on a difference between $TH_{ROI}$ and $TH_{ENV}$, which enables the system to operate well in an uncontrolled environment that does not maintain environmental temperature in a range below ±1° C. and does not maintain humidity in a range below ±3%. In another example, the computer detects the physiological response by performing the following steps: calculating a temperature difference between $TH_{ROI}$ and $TH_{ENV}$ taken at time x ($\Delta T_x$), calculating a temperature difference between $TH_{ROI}$ and $TH_{ENV}$ taken at time y ($\Delta T_y$), and detecting the physiological response based on a difference between $\Delta T_x$ and $\Delta T_y$. Optionally, detecting the physiological response is based on the difference between $\Delta T_x$ and $\Delta T_y$ reaching a predetermined threshold. Optionally, the predetermined threshold is selected from a threshold in the time domain, and/or a threshold in the frequency domain. Optionally, the magnitude of the difference between $\Delta T_x$ and $\Delta T_y$ is indicative of an extent of the physiological response. It is noted that sentences such as "calculating a difference between M and N" or "detecting a difference between M and N" are intended to cover any function that is proportional to the difference between M and N.

Because the FOV of $CAM_{out}$ is limited and the responsivity of $CAM_{out}$ decreases when drawing away from the optical axis, it may be beneficial to utilize two or more $CAM_{out}$ pointed at different angles.

In one embodiment, the system may include a second outward-facing head-mounted thermal camera ($CAM_{out2}$), which takes thermal measurements of the environment ($TH_{ENV2}$). Optionally, there is an angle of at least 30° between the optical axes of $CAM_{out}$ and $CAM_{out2}$. Utilizing two or more outward-facing head-mounted thermal cameras such as $CAM_{out}$ and $CAM_{out2}$ can help identify cases in which there is a directional environmental interference (e.g., sunlight coming from a certain direction). In some cases, such a directional interference can lead to refraining from making a detection of the physiological response. For example, responsive to receiving a first set of measurements in which $TH_{ROI}$ reach a first threshold while the difference between $TH_{ENV}$ and $TH_{ENV2}$ does not reach a second threshold, the computer detects the physiological response. However, responsive to receiving a second set of measurements in which $TH_{ROI}$ reach the first threshold while the difference between $TH_{ENV}$ and $TH_{ENV2}$ reaches the second threshold, the computer does not detect the physiological response. Optionally, the computer detects the physiological response based on a difference between $TH_{ROI}$, $TH_{ENV}$, and $TH_{ENV2}$, while taking into account the angle between the optical axes of $CAM_{out}$ and $CAM_{out2}$ and a graph of responsivity as function of the angle from the optical axes of each of $CAM_{out}$ and $CAM_{out2}$.

In another embodiment, $CAM_{in}$ and $CAM_{out}$ are located to the right of the vertical symmetry axis that divides the user's face, and the ROI is on the right side of the face. Optionally, the system includes a second inward-facing head-mounted thermal camera ($CAM_{in2}$) and a second outward-facing head-mounted thermal camera ($CAM_{out2}$) located to the left of the vertical symmetry axis. $CAM_{in2}$ takes thermal measurements of a second ROI ($TH_{ROI2}$) on the left side of the face, and does not occlude the second ROI ($ROI_2$). $CAM_{out2}$ takes thermal measurements of the environment ($TH_{ENV2}$) that is more to the left relative to $TH_{ENV}$. In this embodiment, the computer detects the physiological response also based on $TH_{ROI2}$ and $TH_{ENV2}$.

In still another embodiment, the optical axes of $CAM_{in}$ and $CAM_{out}$ are above the Frankfort horizontal plane, and the system further includes a second inward-facing head-mounted thermal camera ($CAM_{in2}$) and a second outward-facing head-mounted thermal camera ($CAM_{out2}$), located such that their optical axes are below the Frankfort horizontal plane, which take thermal measurements $TH_{ROI2}$ and $TH_{ENV2}$, respectively. In this embodiment, the computer detects the physiological response also based on $TH_{ROI2}$ and $TH_{ENV2}$.

Optionally, the computer detects the physiological response by performing at least one of the following calculations: (i) when the difference between $TH_{ENV}$ and $TH_{ENV2}$ reaches a threshold, the computer normalizes $TH_{ROI}$ and $TH_{ROI2}$ differently against thermal interference from the environment, (ii) when $TH_{ENV}$ does not reach a predetermined threshold for thermal environmental interference, while $TH_{ENV2}$ reaches the predetermined threshold, the computer assigns $TH_{ROI}$ a higher weight than $TH_{ROI2}$ for detecting the physiological response, and (iii) the computer generates feature values based on $TH_{ROI}$, $TH_{ENV}$, $TH_{ENV2}$ and optionally $TH_{ROI2}$ and utilizes a model to detect, based on the feature values, the physiological response. Optionally, the model was trained based on a first set of $TH_{ROI}$, $TH_{ROI2}$, $TH_{ENV}$ and $TH_{ENV2}$ of one or more users taken while the one or more users had the physiological response, and a second set of $TH_{ROI}$, $TH_{ROI2}$, $TH_{ENV}$ and $TH_{ENV2}$ of the one or more users taken while the one or more users did not have the physiological response.

In addition to having one or more $CAM_{out}$, or instead of having the one or more $CAM_{out}$, some embodiments may include a sensor that may be used to address various other confounding factors, such as user movements and wind, which are discussed below. Optionally, the sensor is coupled to a frame worn on the user's head. An example of such a sensor is sensor 68 in FIG. 28a.

In one embodiment, the sensor takes measurements (denoted $m_{conf}$) that are indicative of an extent of the user's activity, an orientation of the user's head, and/or a change in a position of the user's body. For example, the sensor may be (i) a movement sensor that is physically coupled to a frame worn on the user's head, or coupled to a wearable device worn by the user, (ii) a visible-light camera that takes images of the user, and/or (iii) an active 3D tracking device that emits electromagnetic waves and generates 3D images based on received reflections of the emitted electromagnetic waves. Optionally, the computer detects the physiological response also based on $m_{conf}$. In one example, the computer may refrain from detecting the physiological response if $m_{conf}$ reaches a threshold (which may indicate the user was very active which causes an increase in body temperature). In another example, the computer generates feature values based on $TH_{ROI}$, $TH_{ENV}$, and $m_{conf}$ and utilizes a model to detect the physiological response based on the feature values. Optionally, the model was trained based on previous $TH_{ROI}$, $TH_{ENV}$, and $m_{conf}$ taken while the user had different activity levels. For example, the model may be trained based on: a first set of previous $TH_{ROI}$, $TH_{ENV}$, and $m_{conf}$ taken while the user was walking or running, and a second set of previous $TH_{ROI}$, $TH_{ENV}$, and $m_{conf}$ taken while the user was sitting or standing.

Figure 30:
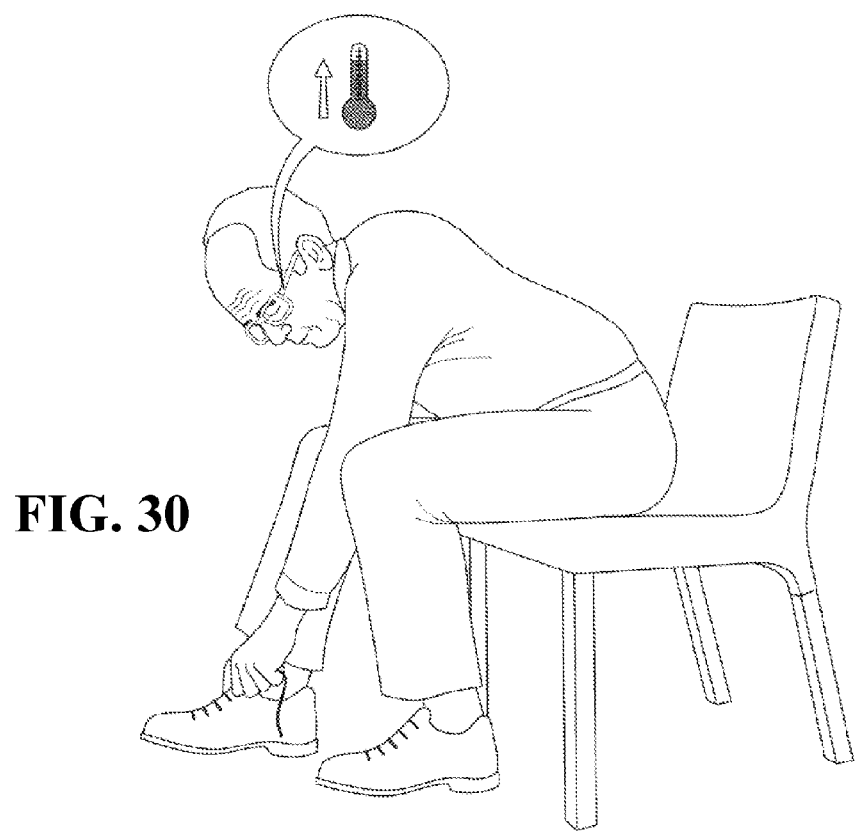
FIG. 30 illustrates an elderly person whose facial temperature increases as a result of bending over.

FIG. 30 illustrates an elderly person whose facial temperature increases as a result of bending the head down towards the floor. In this example, the system receives an indication of the user's action via the sensor (e.g., one or more gyroscopes) and consequently refrains from erroneously detecting certain physiological responses, since the increase in temperature may be attributed to the person being bent over. In one embodiment, a sensor provides indications indicative of bending the head down above a certain degree from the normal to earth, where bending the head down above the certain degree is expected to cause a change in $TH_{ROI}$. The computer generates feature values based on $TH_{ROI}$, $TH_{ENV}$, and $m_{conf}$ and utilizes a model to detect the physiological response based on the feature values. The model was trained based on: a first set of previous $TH_{ROI}$, $TH_{ENV}$, and $m_{conf}$ taken while a user was bending the head down above the certain degree, and a second set of previous $TH_{ROI}$, $TH_{ENV}$, and $m_{conf}$ taken while the user was not bending the head down above the certain degree.

Figure 29:
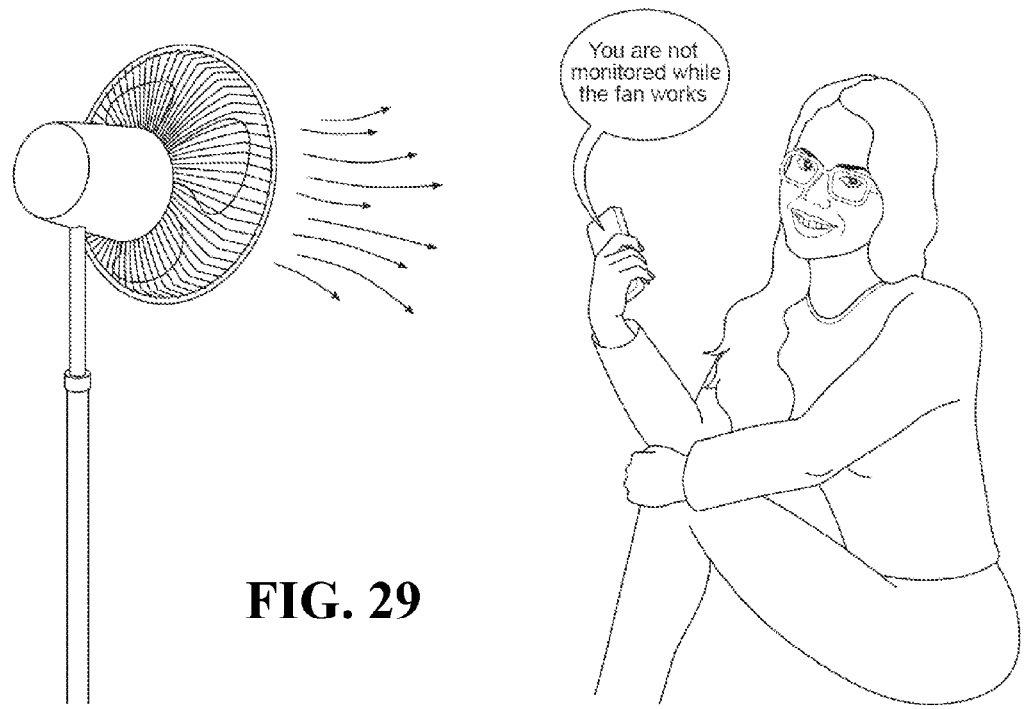
FIG. 29 illustrates a case in which a user receives an indication that she is not being monitored in a windy environment.

In another embodiment, the sensor may be an anemometer that is physically coupled to a frame worn on the user's head, is located less than 15 cm from the face, and provides a value indicative of a speed of air directed at the face ($m_{wind}$). Optionally, the computer detects the physiological response also based on $m_{wind}$. In one example, the computer refrains from detecting the physiological response if $m_{wind}$ reaches a threshold (which may indicate that the user was in an environment with strong wind that may excessively cool regions on the face). In another example, the computer generates feature values based on $TH_{ROI}$, $TH_{ENV}$, and $m_{wind}$ and utilizes a model to detect, based on the feature values, the physiological response. FIG. 29 illustrates a case in which a user receives an indication that she is not being monitored in a windy environment. Optionally, the model was trained based on previous $TH_{ROI}$, $TH_{ENV}$, and $m_{wind}$ taken while a user was in different environments. For example, the model may be trained based on: a first set of previous $TH_{ROI}$, $TH_{ENV}$, and $m_{wind}$ taken while being indoors, and a second set of previous $TH_{ROI}$, $TH_{ENV}$, and $m_{wind}$ taken while being outdoors.

The following is a method for detecting a physiological response while taking into account a confounding factor that involves environmental thermal interferences (e.g., direct sunlight). Having different environmental conditions may cause a system such as the one illustrated in FIG. 28a to behave differently, as shown in the steps below. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, taking thermal measurements of a region of interest ($TH_{ROI}$) on a user's face utilizing an inward-facing head-mounted thermal camera ($CAM_{in}$) worn by the user. In step 2, taking thermal measurements of the environment ($TH_{ENV}$) utilizing an outward-facing head-mounted thermal camera ($CAM_{out}$) worn by the user. In step 3, generating feature values based on $TH_{ROI}$ and $TH_{ENV}$. And in step 4, utilizing a machine learning-based model to detect the physiological response based on the feature values.

The method may optionally further include the following steps: taking a first set of $TH_{ROI}$ (first $TH_{ROI}$), where the first set of $TH_{ROI}$ reach a first threshold; taking a first set of $TH_{ENV}$ (first $TH_{ENV}$), where the first set of $TH_{ENV}$ do not reach a second threshold; detecting, based on the first set of $TH_{ROI}$ and the first set of $TH_{ENV}$, that the user had the physiological response; taking a second set of $TH_{ROI}$, where the second set of $TH_{ROI}$ reach the first threshold; taking a second set of $TH_{ENV}$, where the second set of $TH_{ENV}$ reach the second threshold; and detecting, based on the second set of $TH_{ROI}$ and the second set of $TH_{ENV}$, that the user did not have the physiological response. Optionally, the method further includes: taking a third set of $TH_{ROI}$, where the third set of $TH_{ROI}$ do not reach the first threshold; taking a third set of $TH_{ENV}$, where the third set of $TH_{ENV}$ do not reach the second threshold; and detecting, based on the third set of $TH_{ROI}$ and the third set of $TH_{ENV}$, that the user did not have the physiological response.

The following is a description of a system for detecting a physiological response, which includes a CAM and a sensor. The sensor provides measurements indicative of times at which the user touches the face. Touching the face can warm certain regions of the face, and the system may utilize these measurements in order to account for such cases. Thus, the system may more accurately detect the physiological response compared to systems that do not account for touching of the face.

CAM is worn on the user's head and takes thermal measurements of an ROI ($TH_{ROI}$) on the user's face. Optionally, the system includes a frame to which CAM and the sensor may be physically coupled. Optionally, CAM is located less than 15 cm from the face and/or weighs below 10 g.

The sensor provides measurements (M) indicative of times at which the user touches the ROI. The user may touch the ROI using/with a finger, the palm, a tissue or a towel held by the user, a makeup-related item held by the user, and/or a food item eaten by the user. Touching the ROI may affect $TH_{ROI}$ by increasing or decreasing the temperature at the touched region. Thus, touching the ROI may be considered a confounding factor that can make detections of the physiological response by a computer less accurate. M may include values measured by the sensor and/or results of processing of values measured by the sensor. Various types of sensors may be utilized in different embodiments to generate M, such as: a visible-light camera (where the computer uses image processing to identify touching the ROI), a miniature radar (such as low-power radar operating in the range between 30 GHz and 3,000 GHz, where the computer uses signal processing of the reflections to identify touching the ROI), a miniature active electro-optics distance measurement device, and/or an ultrasound sensor.

In some embodiments, the sensor may be unattached to a frame worn on the user's head. For example, the sensor may include a visible-light camera mounted to an object in the user's environment (e.g., a laptop), and may normally located at a distance greater than 20 cm from the user's face. Optionally, the computer may utilize M to determine when it is likely (but not necessarily certain) that the user touched the face. In one example, the sensor includes a movement-measuring device embedded in a bracelet, and the computer increases the probability for a physical contact with the face when the user's hand is estimated to be at face level and/or close to the face. In another example, the sensor includes an altimeter embedded in a bracelet, and the computer increases the probability for an event of physical contact with the face when the user's hand is estimated to be at face level.

Figure 26A:
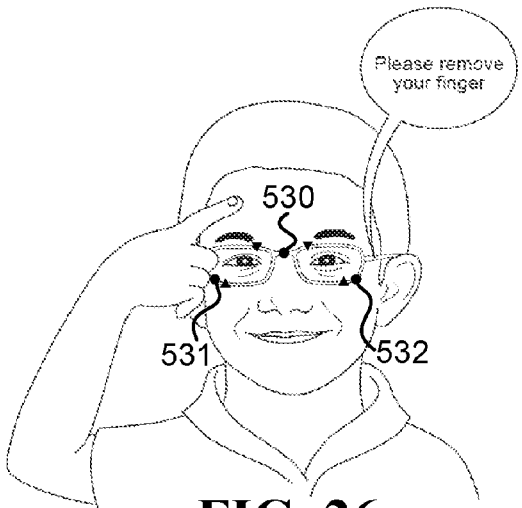
FIG. 26a and FIG. 26b illustrate an embodiment of a system that provides indications when the user touches his/her face.
Figure 26B:
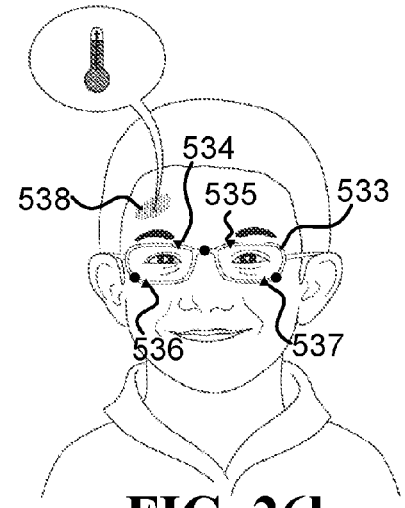

FIG. 26a and FIG. 26b illustrate one embodiment of a system that provides indications when the user touches his/her face. The system includes a frame 533, head-mounted sensors (530, 531, 532) able to detect touching the face, and head-mounted thermal cameras (534, 535, 536, 537). Optionally, the head-mounted sensors are visible-light cameras that take images of the ROIs. Head-mounted sensor 530 captures an ROI above the frame, and head-mounted sensors 531 and 532 capture ROIs below the frame. Hot spot 538, which is measured by the thermal camera 534, was caused by touching the forehead and is unrelated to the physiological response being detected. Upon detecting touching of the ROI, the computer may use the associated thermal measurements differently than it would use had the touching not been detected. Additionally or alternatively, a user interface may provide an indication that touching the ROI hinders the detection of the physiological response.

The computer detects the physiological response based on $TH_{ROI}$ and M. Optionally, since the computer utilizes M to account, at least in part, for the effect of touching the face, on average, detections of the physiological response based on $TH_{ROI}$ and M are more accurate than detections of the physiological response based on $TH_{ROI}$ without M. The computer may utilize $TH_{ROI}$ in various ways in order to detect the physiological response, such as comparing one or more values derived from $TH_{ROI}$ to a threshold and/or comparing $TH_{ROI}$ to a reference time series.

Another approach that may be utilized involves a machine learning-based model. In one embodiment, the computer generates feature values based on $TH_{ROI}$ and M, and utilizes the model to detect, based on the feature values, the physiological response. By utilizing M to generate one or more of the feature values, the computer may make different detections of the physiological response based on similar $TH_{ROI}$ that are taken while there are different extents of touching the ROI. For example, responsive to receiving a first set of measurements in which $TH_{ROI}$ reaches a threshold, while M indicate that there was no touching of the ROI, the computer detects the physiological response. However, responsive to receiving a second set of measurements in which $TH_{ROI}$ reaches the threshold, but M indicate that the user touched the ROI, the computer does not detect the physiological response. Optionally, the model is trained based on samples, each comprising: (i) feature values generated based on $TH_{ROI}$ taken while M indicates touching the ROI, and (ii) a corresponding label indicative of an extent of the physiological response. Optionally, the samples include: a first set of samples with labels corresponding to having the physiological response, which are generated based on M indicating that the ROI was not touched, and a second set of samples with labels corresponding to not having the physiological response, which are generated based on M indicating that the ROI was touched. Optionally, the samples comprise: a third set of samples with labels corresponding to having the physiological response, which are generated based on M indicating that the ROI was touched, and/or a fourth set of samples with labels corresponding to not having the physiological response, which are generated based on M indicating that the ROI was not touched.

M may be utilized by the computer in order to decrease the chance of making incorrect detections of the physiological response. In one embodiment, the computer utilizes, for the detection of the physiological response, $TH_{ROI}$ taken at times in which M are not indicative of touching the ROI. In this embodiment, the computer does not utilize, for the detection of the physiological response, $TH_{ROI}$ taken at times in which M are indicative of touching the ROI. In another embodiment, the computer does not utilize, for the detection of the physiological response, $TH_{ROI}$ taken during at least one of the following intervals starting after M indicate that the user touched the ROI: 0-10 seconds, 0-30 second, 0-60 second, 0-180 seconds, and 0-300 seconds. In yet another embodiment, the computer attributes, for the detection of the physiological response, a smaller weight to $TH_{ROI}$ taken during a certain interval starting after M indicate that the user touched the ROI, compared to a weight attributed to $TH_{ROI}$ taken at times shortly before M indicate that the user touched the ROI. Optionally, the certain interval includes at least one of the following durations: 10-30 second, 30-60 second, 60-120 seconds, and 120-300 seconds. Optionally, the higher the weight attributed to a measurement, the more it influences calculations involved in the detection of the physiological response.

In one embodiment, the system optionally includes a user interface (UI) which notifies the user about touching the ROI. Optionally, this notification is in lieu of notifying extent of the physiological response corresponding to the time the user touched the ROI. The notification may be delivered to the user using a sound, a visual indication on a head-mounted display, and/or a haptic feedback. Optionally, the UI includes a screen of an HMS (e.g., a screen of an augmented reality headset), a screen of a device carried by the user (e.g., a screen of a smartphone or a smartwatch), and/or a speaker (e.g., an earbud or headphones). Optionally, the computer identifies that the duration and/or extent of touching the face reached a threshold, and then commands the UI to alert the user that an accurate detection of the physiological response cannot be made as long as the touching continues.

In one embodiment, the sensor includes a visible-light camera and/or a near-infrared camera, the system is powered by a battery, and the system may operate in a state belonging to a set comprising first and second states. While operating in the first state, the system checks on a regular basis whether the user touches the ROI. While operating in the second state, the system checks whether the user touches the ROI in response to detecting abnormal $TH_{ROI}$. Optionally, the system consumes less power while operating in the second state compared to the power it consumes while operating in the first state.

In one embodiment, the measurements taken by the sensor are further indicative of an angular position of CAM relative to the ROI while the frame is still worn on the head, and the computer detects the physiological response also based on the angular position. Optionally, the measurements of the angular position are utilized to account for instances in which the frame has moved, and consequently CAM captures a region that only overlaps, or does not overlap at all, with the intended ROI. Optionally, the computer is able to detect changes below 5° in the angular position, which may also influence $TH_{ROI}$. Thus, on average, detections of the physiological response based on $TH_{ROI}$ and the angular position are more accurate compared to detections of the physiological responses based on $TH_{ROI}$ without the angular position, while the frame is still worn on the head.

In a first example, responsive to the angular position of CAM relative to the ROI reaching a predetermined threshold, the computer refrains from detecting the physiological response and/or alerts the user.

In a second example, the computer generates feature values based on $TH_{ROI}$ and the angular position, and utilizes a model to detect the physiological response based on the feature values. Optionally, the model was trained based on data comprising $TH_{ROI}$ collected while CAM was at different distances and/or angular positions relative to the ROI. Thus, the model may account, in its parameters, for various effects that the distance and/or orientation of CAM may have on $TH_{RO}$ in order to more accurately detect the physiological response.

In a third example, the sensor includes a visible-light camera that takes images of a region on the user's face, and the computer calculates the angular position of the visible-light camera relative to the face based on analyzing the images, and then calculates the angular position of CAM relative to the ROI based on a predetermined transformation between the angular position of the visible-light camera relative to the face and the angular position of CAM relative to the ROI.

In a fourth example, the sensor includes a transceiver of electromagnetic waves, and the computer calculates the angular position of the transceiver relative to the face based on signal processing of the reflections from the face, and then calculates the angular position of CAM relative to the ROI based on a predetermined transformation between the angular position of the transceiver relative to the face and the angular position of CAM relative to the ROI.

The following method for detecting a physiological response may be used, in some embodiments, by the system described above, which detects a physiological response while taking into account a confounding factor such as touching the face. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, taking thermal measurements of an ROI ($TH_{ROI}$) on a user's face using an inward-facing head-mounted thermal camera. In Step 2, taking, utilizing a sensor, measurements (M) indicative of times at which the user touches the ROI. Touching the ROI may affect $TH_{ROI}$, for example by increasing the temperatures at the ROI (which may increase the values of $TH_{ROI}$). The sensor may be a head-mounted sensor or a sensor that is not head-mounted. And in Step 3, detecting the physiological response based on $TH_{ROI}$ and M. For example, the detection may be performed by the computer, as described above. On average, detections of the physiological response based on $TH_{ROI}$ and M are more accurate compared to detections of the physiological response based on $TH_{ROI}$ without M.

Optionally, the method further includes the following steps: generating feature values based on $TH_{ROI}$ and M, and utilizing a model for detecting the physiological response based on the feature values. Optionally, the model was trained based on samples, each comprising: (i) feature values generated based on previous $TH_{ROI}$ taken while M indicates touching the ROI, and (ii) a corresponding label indicative of an extent of the physiological response. Optionally, the samples include: a first set of samples with labels corresponding to having the physiological response, which are generated based on M indicating that the ROI was not touched, and a second set of samples with labels corresponding to not having the physiological response, which are generated based on M indicating that the ROI was touched.

Optionally, M are further indicative of angular position of CAM relative to the ROI, while the frame is still worn on the head. And the method further includes a step of detecting the physiological response also based on the angular position. On average, detections of the physiological response based on $TH_{ROI}$ and the angular position are more accurate compared to detections of the physiological responses based on $TH_{ROI}$ without the angular position, while the frame is still worn on the head.

The following is a description of a system that detects a physiological response while taking into account a consumption of a confounding substance. When a person consumes a confounding substance, it may affect thermal measurements of an ROI ($TH_{ROI}$) on the person's face. The affect to $TH_{ROI}$ can be attributed to various physiological and/or metabolic processes that may ensue following the consumption of the confounding substance, which can result (amongst possibly other effects) in a raising or decreasing of the temperature at the ROI in a manner that is unrelated to the physiological response being detected. Thus, embodiments of this system utilize indications indicative of consumption of a confounding substance (such as medication, an alcoholic beverage, a caffeinated beverage, and/or a cigarette) to improve the system's detection accuracy. In one embodiment, the system includes a CAM and a computer.

CAM is worn on the user's head and takes thermal measurements of an ROI ($TH_{ROI}$) on the user's face. Optionally, the system includes a frame to which CAM and the device are physically coupled. Optionally, CAM is located less than 15 cm from the face and/or weighs below 10 g.

In different embodiments, the ROI may cover different regions on the face and CAM may be located at different locations on a frame worn on the user's head and/or at different distances from the user's face. In one embodiment, the ROI is on the forehead, and CAM is physically coupled to an eyeglasses frame, located below the ROI, and does not occlude the ROI. Optionally, the physiological response detected in this embodiment is stress, a headache, and/or a stroke. In another embodiment, the ROI is on the periorbital area, and CAM is located less than 10 cm from the ROI. Optionally, the physiological response detected in this embodiment is stress. In yet another embodiment, the ROI is on the nose, and CAM is physically coupled to an eyeglasses frame and is located less than 10 cm from the face. Optionally, the physiological response detected in this embodiment is an allergic reaction. In still another embodiment, the ROI is below the nostrils, and CAM: is physically coupled to an eyeglasses frame, located above the ROI, and does not occlude the ROI. Optionally, the ROI covers one or more areas on the upper lip, the mouth, and/or air volume(s) through which the exhale streams from the nose and/or mouth flow, and the physiological response detected in this embodiment is a respiratory parameter such as the user's breathing rate.

The computer may receive, from a device, an indication indicative of consuming a confounding substance that is expected to affects $TH_{ROI}$, such as an alcoholic beverage, a medication, caffeine, and/or a cigarette. Various types of devices may be utilized in different embodiments in order to identify consumption of various confounding substances.

In one embodiment, the device includes a visible-light camera that takes images of the user and/or the user's environment. Optionally, the visible-light camera is a head-mounted visible-light camera having in its field of view a volume that protrudes out of the user's mouth. Optionally, the computer identifies a consumption of the confounding substance based on analyzing the images. In one example, the visible-light camera may belong to a camera-based system such as OrCam (http://www.orcam.com/), which is utilized to identify various objects, products, faces, and/or recognize text. In another example, images captured by the visible-light camera may be utilized to determine the nutritional composition of food a user consumes. Such an approach in which images of meals are utilized to generate estimates of food intake and meal composition, is described in Noronha, et al., "Platemate: crowdsourcing nutritional analysis from food photographs", Proceedings of the 24th annual ACM symposium on User interface software and technology, ACM, 2011. Additional examples of how a visible-light camera may be utilized to identify consumption of various substances is given in U.S. Pat. No. 9,053,483 (Personal audio/visual system providing allergy awareness) and in U.S. Pat. No. 9,189,021 (Wearable food nutrition feedback system).

In another embodiment, the device includes a microphone that records the user, and the computer identifies a consumption of the confounding substance utilizing a sound recognition algorithm operated on a recording of the user. Optionally, the sound recognition algorithm comprises a speech recognition algorithm configured to identify words that are indicative of consuming the confounding substance.

In yet another embodiment, the confounding substance is a medication, and the device includes a pill dispenser that provides an indication indicating that the user took a medication, and/or a sensor-enabled pill that includes an ingestible signal generator coupled to a medication that is configured to generate a body-transmissible signal upon ingestion by a user, such as the sensor-enabled pill described in PCT publication WO/2016/129286. Optionally, the indication indicates the type of medication and/or its dosage.

In still another embodiment, the device is a refrigerator, a pantry, and/or a serving robot. Optionally, the device provides an indication indicative of the user taking an alcoholic beverage and/or a food item.

In yet another embodiment, the device has an internet-of-things (IoT) capability through which the indication is provided to the system. For example, the device may be part of a "smart device" with network connectivity.

And in yet another embodiment, the device belongs to a user interface that receives an indication from the user or/or a third party about the consuming of the confounding substance.

Due to various metabolic and/or other physiological processes, consumption of a confounding substance may affect $TH_{ROI}$. For example, many drugs are known to act on the hypothalamus and other brain centers involved in controlling the body's thermoregulatory system. Herein, stating "the confounding substance affects $TH_{ROI}$" means that consuming the confounding substance leads to a measurable change of the temperature at the ROI, which would likely not have occurred had the confounding substance not been consumed. Similarly, a time in which "confounding substance did not affect $TH_{ROI}$" is a time that occurs after at least a certain duration has elapsed since the confounding substance was last consumed (or was not consumed at all), and the consumption of the confounding substance is no longer expected to have a noticeable effect on the ROI temperature. This certain duration may depend on factors such as the type of substance, the amount consumed, and previous consumption patterns. For example, the certain duration may be at least: 30 minutes, two hours, or a day.

The duration of the effect of a confounding substance may vary between substances, and may depend on various factors such as the amount of substance, sex, weight, genetic characteristics, and the user's state. For example, consumption of alcohol on an empty stomach often has a greater effect on $TH_{ROI}$ than consumption of alcohol with a meal. Some confounding substances may have a long-lasting effect, possibly throughout the period they are taken. For example, hormonal contraceptives can significantly alter daily body temperatures. Other confounding factors, such as caffeine and nicotine, may have shorter lasting effects, typically subsiding within less than an hour or two following their consumption.

The computer detects the physiological response based on $TH_{ROI}$ and the indication indicative of consuming the confounding substance. In one embodiment, the computer refrains from detecting the physiological response within a certain window during which the confounding substance affected the user (e.g., an hour, two hours, or four hours). In another embodiment, the computer utilizes a model, in addition to $TH_{ROI}$ and the indication, to detect whether the user had the physiological response during the time that a consumed confounding substance affected $TH_{ROI}$. Optionally, the computer detects the physiological response by generating feature values based on $TH_{ROI}$ and the indication (and possibly other sources of data), and utilizing the model to calculate, based on the feature values, a value indicative of the extent of the physiological response. Optionally, the feature values include a feature value indicative of one or more of the following: the amount of the consumed confounding substance, the dosage of the consumed confounding substance, the time that has elapsed since the confounding substance had last been consumed, and/or the duration during which the confounding factor has been consumed (e.g., how long the user has been taking a certain medication).

In one embodiment, the model was trained based on data collected from the user and/or other users, which includes $TH_{ROI}$, the indications described above, and values representing the physiological response corresponding to when $TH_{ROI}$ were taken. Optionally, the data is used to generate samples, with each sample comprising feature values and a label. The feature values of each sample are generated based on $TH_{ROI}$ taken during a certain period and an indication indicating whether a confounding substance affected $TH_{ROI}$ taken during the certain period. The label of the sample is generated based on one or more of the values representing the physiological response, and indicates whether (and optionally to what extent) the measured user had the physiological response during the certain period. Optionally, the data used to train the model reflects both being affected and being unaffected by the confounding substance. For example, the data used to train the model may include: a first set of $TH_{ROI}$ taken while the confounding substance affected $TH_{ROI}$, and a second set of $TH_{ROI}$ taken while the confounding substance did not affect $TH_{ROI}$. Optionally, each of the first and second sets comprises at least some $TH_{ROI}$ taken while the measured user had the physiological response and at least some $TH_{ROI}$ taken while the measured user did not have the physiological response.

Using the indications (indicative of the user consuming a confounding substance) may lead to cases where the detection of the physiological response depends on whether the confounding substance was consumed. In one example, in which the physiological response is detected when $TH_{ROI}$ reach a threshold, the computer's detection behavior may be as follows: the computer detects the physiological response based on first $TH_{ROI}$ for which there is no indication indicating that the first $TH_{ROI}$ were affected by a consumption of the confounding substance, and the first $TH_{ROI}$ reach the threshold; the computer does not detect the physiological response based on second $TH_{ROI}$ for which there is an indication indicating that the second $TH_{ROI}$ were affected by a consumption of the confounding substance, and the second $TH_{ROI}$ also reach the threshold; and the computer does not detect the physiological response based on third $TH_{ROI}$ for which there is no indication indicating that the third $TH_{ROI}$ were affected by a consumption the confounding substance, and the third $TH_{ROI}$ do not reach the threshold.

Figure 31:
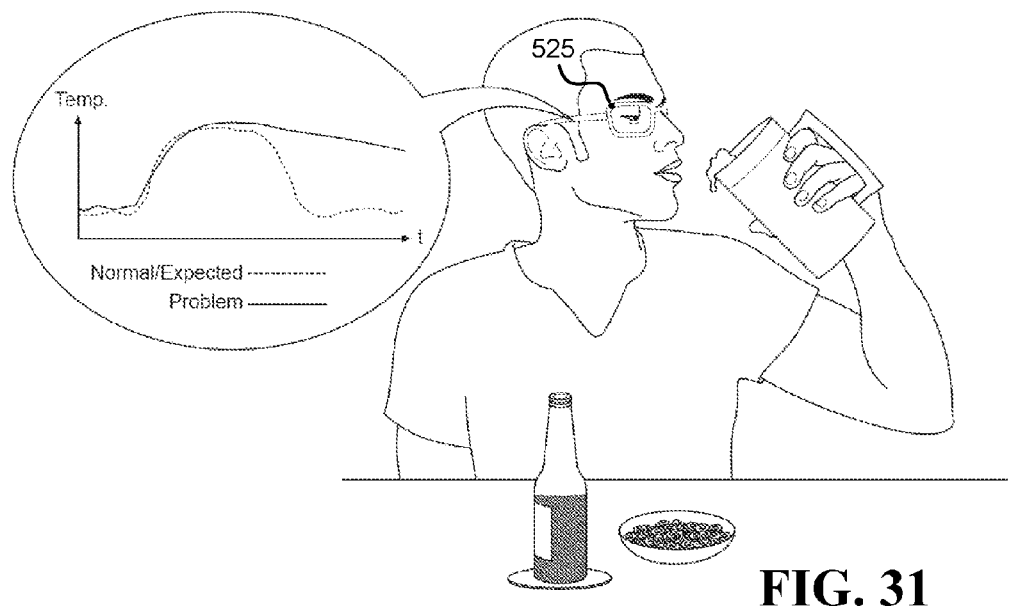
FIG. 31 illustrates the effect of consuming alcohol on values of thermal measurements.

The following three figures illustrate scenarios where issuing of alerts are dependent on the consumption of confounding substances. FIG. 31 illustrates that the effect of consuming alcohol on a certain $TH_{ROI}$ usually decreases after duration typical to the user (e.g., the duration is based on previous measurements of the user). Thus, when the effect remains high there may be a problem and the system may issue an alert. The figure illustrates an outward-facing visible-light camera 525 that generates the indications indicative of when the user consumes alcoholic beverages.

Figure 32:
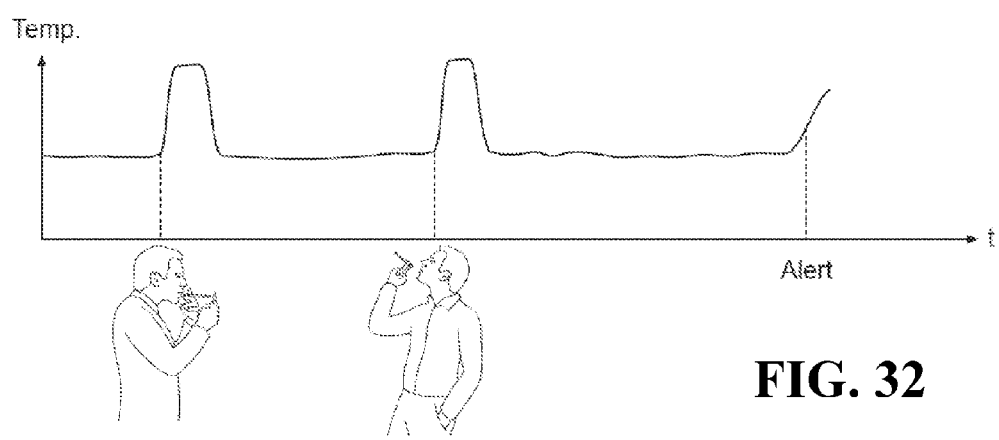
FIG. 32 illustrates an increase in the thermal measurements due to smoking.

FIG. 32 illustrates a usual increase in a certain $TH_{ROI}$ while the user smokes. The system identifies when the user smoked (e.g., based on images taken by the outward-facing visible-light camera 525) and doesn't alert because of an increase in $TH_{ROI}$ caused by the smoking. However, when the temperature rises without the user having smoked for a certain time, then it may be a sign that there is a problem, and the user might need to be alerted.

Figure 33:
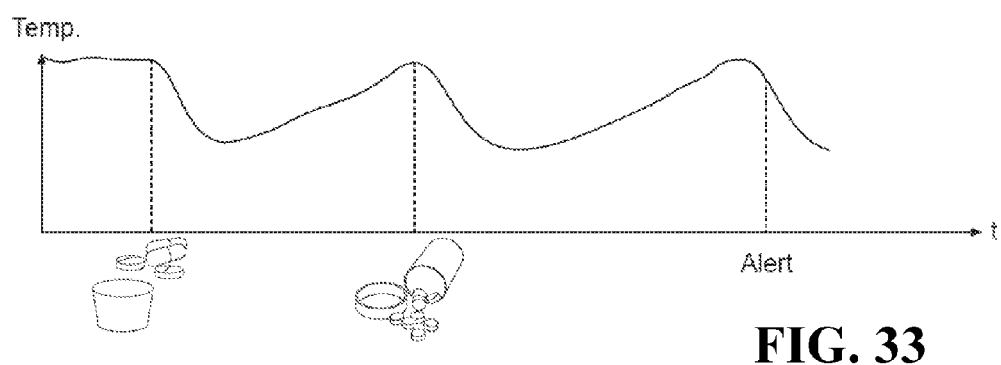
FIG. 33 illustrates a decrease in the thermal measurements due to taking medication.

FIG. 33 illustrates the expected decrease in a certain $TH_{ROI}$ after the user takes medication, based on previous $TH_{ROI}$ of the user. The system identifies when the medication is consumed, and does not generate an alert at those times. However, when $TH_{ROI}$ falls without medication having been taken, it may indicate a physiological response of which the user should be made aware.

The following method for detecting a physiological response while taking into account consumption of a confounding substance may be used, in some embodiments, by the system described above, which detects a physiological response while taking into account a consumption of a confounding substance. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking thermal measurements of an ROI ($TH_{ROI}$) on the user's face utilizing an inward-facing head-mounted thermal camera.

In Step 2, receiving an indication indicative of consuming a confounding substance that affects $TH_{ROI}$. Optionally, the indication is received from one or more of the various device described above that provide an indication indicative of consuming a confounding substance. Optionally, the indication is generated based on image processing of images taken by a head-mounted visible-light camera having in its field of a volume that protrudes out of the user's mouth.

And in Step 3, detecting the physiological response, while the consumed confounding substance affects $TH_{ROI}$, based on $TH_{ROI}$, the indication, and a model. Optionally, the model was trained on: a first set of $TH_{ROI}$ taken while the confounding substance affected $TH_{ROI}$, and a second set of $TH_{ROI}$ taken while the confounding substance did not affect $TH_{ROI}$. Optionally, the model is a machine learning-based model, and this step involves: generating feature values based on $TH_{ROI}$ and the indication, and utilizing the machine learning-based model to detect the physiological response based on the feature values.

One way in which a user may wear a head-mounted camera (such as CAM or VCAM) involves attaching a clip-on device that houses the camera onto a frame worn by the user, such as an eyeglasses frame. This may enable the user to be selective regarding when to use the head-mounted camera and take advantage of eyeglasses that he or she owns, which may be comfortable and/or esthetically pleasing.

In some embodiments, the clip-on device includes a body that may be attached and detached, multiple times, from a pair of eyeglasses in order to secure and release the clip-on device from the eyeglasses. The body is a structure that has one or more components fixed to it. For example, the body may have one or more inward-facing camera fixed to it. Additionally, the body may have a wireless communication module fixed to it. Some additional components that may each be optionally fixed to the body include a processor, a battery, and one or more outward-facing cameras.

In one example, "eyeglasses" are limited to prescription eyeglasses, prescription sunglasses, plano sunglasses, and/or augmented reality eyeglasses. This means that "eyeglasses" do not refer to helmets, hats, virtual reality devices, and goggles designed to be worn over eyeglasses. Additionally or alternatively, neither attaching the clip-on device to the eyeglasses nor detaching the clip-on device from the eyeglasses should take more than 10 seconds for an average user. This means that manipulating the clip-on device is not a complicated task. Optionally, the body is configured to be detached from the eyeglasses by the user who wears the eyeglasses, who is not a technician, and without using a tool such as a screwdriver or a knife. Thus, the clip-on device may be attached and detached as needed, e.g., enabling the user to attach the clip-on when there is a need to take measurements, and otherwise have it detached.

In order to be warn comfortably, possibly for long durations, the clip-on device is a lightweight device, weighing less than 40 g (i.e., the total weight of the body and the components fixed to it is less than 40 g). Optionally, the clip-on device weighs below 20 g and/or below 10 g.

The body is a structure to which components (e.g., an inward-facing camera) may be fixed such that the various components do not fall off while the clip-on device is attached to the eyeglasses. Optionally, at least some of the various components that are fixed to the body remain in the same location and/or orientation when the body is attached to the eyeglasses. Herein, stating that a component is "fixed" to the body is intended to indicate that, during normal use (e.g., involving securing/releasing the clip-on device), these components are typically not detached from the body. This is opposed to the body itself, which in normal use is separated from the eyeglasses frame, and as such, is not considered "fixed" to the eyeglasses frame.

In some embodiments, the body is a rigid structure made of a material such as plastic, metal, and/or an alloy (e.g., carbon alloy). Optionally, the rigid structure is shaped such that it fits the contours of at least a portion of the frame of the eyeglasses in order to enable a secure and stable attachment to the eyeglasses. In other embodiments, the body may be made of a flexible material, such as rubber. Optionally, the flexible body is shaped such that it fits the contours of at least a portion of the frame of the eyeglasses in order to enable a secure and stable attachment to the eyeglasses. Additionally or alternatively, the flexible body may assume the shape of a portion of the frame when it is attached to the eyeglasses.

The body may utilize various mechanisms in order to stay attached to the eyeglasses. In one embodiment, the body may include a clip member configured to being clipped on the eyeglasses. In another embodiment, the body may include a magnet configured to attach to a magnet connected to the eyeglasses and/or to a metallic portion of the eyeglasses. In yet another embodiment, the body may include a resting tab configured to secure the clip-on to the eyeglasses. In still another embodiment, the body may include a retention member (e.g., a clasp, buckle, clamp, fastener, hook, or latch) configured to impermanently couple the clip-on to the eyeglasses. For example, clasp 147 is utilized to secure the clip-on device illustrated in FIG. 15a to the frame of the eyeglasses. And in yet another embodiment, the body may include a spring configured to apply force that presses the body towards the eyeglasses. An example of this type of mechanism is illustrated in FIG. 17a where spring 175 is used to apply force that pushes body 170 and secures it in place to frame 176.

Herein, to "impermanently couple" something means to attach in a way that is easily detached without excessive effort. For example, coupling something by clipping it on or closing a latch is considered impermanently coupling it. Coupling by screwing a screw with a screwdriver, gluing, or welding is not considered impermanently coupling. The latter would be examples of what may be considered to "fix" a component to the body.

The inward-facing camera is fixed to the body. It takes images of a region of interest on the face of a user who wears the eyeglasses. Optionally, the inward-facing camera remains pointed at the region of interest even when the user's head makes lateral and/or angular movements. The inward-facing camera may be any of the CAMs and/or VCAMs described in this disclosure. Optionally, the inward-facing camera weighs less than 10 g, 5 g or 1 g. Optionally, the inward-facing camera is a thermal camera based on a thermopile sensor, a pyroelectric sensor, or a microbolometer sensor, which may be a FPA sensor.

In one embodiment, the inward-facing camera includes a multi-pixel sensor and a lens, and the sensor plane is tilted by more than 2° relative to the lens plane according to the Scheimpflug principle in order to capture sharper images when the body is attached to the eyeglasses that are worn by a user.

The clip-one device may include additional components that are fixed to it. In one embodiment, the clip-on device include a wireless communication module fixed to the body which transmits measurements (e.g., images and/or thermal measurements) taken by one or more of the cameras that are fixed to the body. Optionally, the clip-on device may include a battery fixed to the body, which provides power to one or more components fixed to the body. Optionally, the clip-on device may include a processor that controls the operation of one or more of the components fixed to the body and/or processes measurements taken by the camera fixed to the body.

In some embodiments, a computer receives measurements taken by the inward-facing camera (and possibly other cameras fixed to the body), and utilizes the measurements to detect a physiological response. Optionally, the computer is not fixed to the body. For example, the computer may belong to a device of the user (e.g., a smartphone or a smartwatch), or the computer may be a cloud-based server. Optionally, the computer receives, over a wireless channel, the measurements, which are sent by the wireless communication module.

The following are various examples of embodiments using different types of inward- and outward-facing cameras that are fixed to the body, which may be used to take images of various regions of interest on the face of the user who wears the eyeglasses. It is to be noted that while the discussion below generally refers to a single "inward-facing camera" and/or a single "outward-facing camera", embodiments of the clip-on device may include multiple inward- and/or outward-facing cameras.

In some embodiments, the inward-facing camera is a thermal camera. Optionally, when the body is attached to the eyeglasses, the thermal camera is located less than 5 cm from the user's face. Optionally, measurements taken by the thermal camera are transmitted by the wireless communication module and are received by a computer that uses them to detect a physiological response of the user. In one example, when the body is attached to the eyeglasses, the optical axis of the thermal camera is above 20° from the Frankfort horizontal plane, and the thermal camera takes thermal measurements of a region on the user's forehead. In another example, when the body is attached to the eyeglasses, the thermal camera takes thermal measurements of a region on the user's nose. In yet another example, when the body is attached to the eyeglasses, the thermal camera takes thermal measurements of a region on a periorbital area of the user.

In one embodiment, the inward-facing camera is a thermal camera. When the body is attached to the eyeglasses, the thermal camera is located below eye-level of a user who wears the eyeglasses and at least 2 cm from the vertical symmetry axis that divides the user's face (i.e., the axis that goes down the center of the user's forehead and nose). Additionally, when the body is attached to the eyeglasses, the inward-facing thermal camera takes thermal measurements of a region on at least one of the following parts of the user's face: upper lip, lips, and a cheek. Optionally, measurements taken by the thermal camera are transmitted by the wireless communication module and are received by a computer that uses them to detect a physiological response of the user.

In another embodiment, the inward-facing camera is a visible-light camera. Optionally, when the body is attached to the eyeglasses, the visible-light camera is located less than 10 cm from the user's face. Optionally, images taken by the visible-light camera are transmitted by the wireless communication module and are received by a computer that uses them to detect a physiological response of the user. Optionally, the computer detects the physiological response based on facial skin color changes (FSCC) that are recognizable in the images. In one example, when the body is attached to the eyeglasses, the optical axis of the visible-light camera is above 20° from the Frankfort horizontal plane, and the visible-light camera takes images of a region located above the user's eyes. In another example, when the body is attached to the eyeglasses, the visible-light camera takes images of a region on the nose of a user who wears the eyeglasses. In still another example, the computer detects the physiological response based on facial expressions, and when the body is attached to the eyeglasses, the visible-light camera takes images of a region above or below the user's eyes.

In still another embodiment, the inward-facing camera is a visible-light camera, and when the body is attached to the eyeglasses, the visible-light camera takes images of a region on an eye ($IM_E$) of a user who wears the eyeglasses, and is located less than 10 cm from the user's face. Optionally, the images are transmitted by the wireless communication module and are received by a computer that detects a physiological response based in $IM_E$.

In one example, the computer detects the physiological response based on color changes to certain parts of the eye, such as the sclera and/or the iris. Due to the many blood vessels that are close to the surface of the eye, physiological responses that are manifested through changes to the blood flow (e.g., a cardiac pulse and certain emotional responses), may cause recognizable changes to the color of the certain parts of the eye. The various techniques described in this disclosure for detecting a physiological response based on FSCC that is recognizable in images can be applied by one skilled in the art to detect a physiological response based on color changes to the sclera and/or iris; while the sclera and iris are not the same color as a person's skin, they too exhibit blood flow-related color changes that are qualitatively similar to FSCC, and thus may be analyzed using similar techniques to the techniques used to analyze FSCC involving the forehead, nose, and/or cheeks.

In another example, $IM_E$ may be utilized to determine the size of the pupil, which may be utilized by the computer to detect certain emotional responses (such as based on the assumption that the pupil's response reflects emotional arousal associated with increased sympathetic activity).

If needed as part of the computer's detection of the physiological response, identifying which portions of $IM_E$ correspond to certain parts of the eye (e.g., the sclera or iris) can be done utilizing various image processing techniques known in the art. For example, identifying the iris and pupil size may be done using the techniques described in US patent application 20060147094, or in Hayes, Taylor R., and Alexander A. Petrov. "Mapping and correcting the influence of gaze position on pupil size measurements." Behavior Research Methods 48.2 (2016): 510-527. Additionally, due to the distinct color differences between the skin, the iris, and the sclera, identification of the iris and/or the white sclera can be easily done by image processing methods known in the art.

In one embodiment, the inward-facing camera is a visible-light camera; when the body is attached to the eyeglasses, the visible-light camera is located below eye-level of a user who wears the eyeglasses, and at least 2 cm from the vertical symmetry axis that divides the user's face. The visible-light camera takes images ($IM_{ROI}$) of a region on the upper lip, lips, and/or a cheek. Optionally, $IM_{ROI}$ are transmitted by the wireless communication module and are received by a computer that uses them to detect a physiological response. In one example, the physiological response is an emotional response, which is detected based on extracting facial expressions from $IM_{ROI}$. In another example, the physiological response is an emotional response, which is detected based on FSCC recognizable in $IM_{ROI}$. In still another example, the physiological response, which is detected based FSCC recognizable in $IM_{ROI}$, is heart rate and/or breathing rate.

The body may include an outward-facing camera that may be utilized to provide measurements that may be used to account for various environmental interferences that can decrease detections of the physiological response of a user who wears the eyeglasses. Optionally, the outward-facing camera is a head-mounted camera. Optionally, the outward-facing camera is fixed to the body.

In one embodiment, the inward-facing camera is a thermal camera, and when the body is attached to the eyeglasses, the thermal camera is located less than 10 cm from the face of the user who wears the eyeglasses, and takes thermal measurements of a region of interest ($TH_{ROI}$) on the face of the user. In this embodiment, an outward-facing head-mounted thermal camera takes thermal measurements of the environment ($TH_{ENV}$). The wireless communication module transmits $TH_{ROI}$ and $TH_{ENV}$ to a computer that detects a physiological response of the user based on $TH_{ROI}$ and $TH_{ENV}$.

Optionally, the computer utilizes $TH_{ENV}$ to account for thermal interferences from the environment, as discussed elsewhere herein.

In another embodiment, the inward-facing camera is a visible-light camera, and when the body is attached to the eyeglasses, the visible-light camera is located less than 10 cm from the face of the user who wears the eyeglasses and takes images of a region of interest ($IM_{ROI}$) on the face of the user. In this embodiment, an outward-facing head-mounted visible-light camera takes images of the environment ($IM_{ENV}$). The wireless communication module transmits $IM_{ROI}$ and $IM_{ENV}$ to a computer that detects a physiological response of the user based on $IM_{ROI}$ and $IM_{ENV}$. Optionally, the computer detects the physiological response based on FSCC recognizable in $IM_{ROI}$, and utilizes $IM_{ENV}$ to account for variations in ambient light, as discussed elsewhere herein.

Inward-facing cameras attached to the body may be utilized for additional purposes, beyond detection of physiological responses. In one embodiment, the inward-facing camera is a visible-light camera, and the clip-on device includes a second visible-light camera that is also fixed to the body. Optionally, the visible-light camera and/or the second visible-light camera are light field cameras. Optionally, when the body is attached to the eyeglasses, the first and second visible-light cameras are located less than 10 cm from the user's face, and take images of a first region above eye-level and a second region on the upper lip ($IM_{ROI}$ and $IM_{ROI2}$, respectively). Optionally, the wireless communication module transmits $IM_{ROI}$ and $IM_{ROI2}$ to a computer that generates an avatar of the user based on $IM_{ROI}$ and $IM_{ROI2}$. Some of the various approaches that may be utilized to generate the avatar based on $IM_{ROI}$ and $IM_{ROI2}$ are described in co-pending US patent publication 2016/0360970.

Different embodiments of the clip-on device may involve devices of various shapes, sizes, and/or locations of attachment to the eyeglasses. FIG. 14a to FIG. 18 illustrate some examples of clip-on devices. When the body is attached to the eyeglasses, most of the clip-on device may be located in front of the frame of the eyeglasses, as illustrated in FIG. 14b, FIG. 15b, and FIG. 18, or alternatively, most of the clip-on device may be located behind the frame, as illustrated in FIG. 16b and FIG. 17b. Some clip-on devices may include a single unit, such as illustrated in FIG. 15a and FIG. 17a. While other clip-on devices may include multiple units (which each may optionally be considered a separate clip-on device). Examples of multiple units being attached to the frame are illustrated in FIG. 14b, FIG. 16b, and FIG. 18. The following is a more detailed discussion regarding embodiments illustrated in the figures mentioned above.

FIG. 14a, FIG. 14b, and FIG. 14c illustrate two right and left clip-on devices comprising bodies 141 and 142, respectively, which are configured to attached/detached from an eyeglasses frame 140. The body 142 has multiple inward-facing cameras fixed to it, such as camera 143 that points at a region on the lower part of the face (such as the upper lip, mouth, nose, and/or cheek), and camera 144 that points at the forehead. The body 142 may include other electronics 145, such as a processor, a battery, and/or a wireless communication module. The bodies 141 and 142 of the left and right clip-on devices may include additional cameras illustrated in the drawings as black circles.

In one another embodiment, the eyeglasses include left and right lenses, and when the body is attached to the eyeglasses, most of the volume of the clip-on device is located to the left of the left lens or to the right of the right lens. Optionally, the inward-facing camera takes images of at least one of: a region on the nose of a user wearing the eyeglasses, and a region on the mouth of the user. Optionally, a portion of the clip-on device that is located to the left of the left lens or to the right of the right lens does not obstruct the sight of the user when looking forward.

FIG. 15a and FIG. 15b illustrate a clip-on device that includes a body 150, to which two head-mounted cameras are fixed: a head-mounted camera 148 that points at a region on the lower part of the face (such as the nose), and a head-mounted camera 149 that points at the forehead. The other electronics (such as a processor, a battery, and/or a wireless communication module) are located inside the body 150. The clip-on device is attached and detached from the frame of the eyeglasses with the clasp 147.

In one embodiment, when the body is attached to the eyeglasses, most of the volume of the clip-on device is located above the lenses of the eyeglasses, and the inward-facing camera takes images of a region on the forehead of a user who wears the eyeglasses. Optionally, a portion of the clip-on device that is located above the lenses of the eyeglasses does not obstruct the sight of the user when looking forward.

While the clip-on device may often have a design intended to reduce the extent to which it sticks out beyond the frame, in some embodiments, the clip-on device may include various protruding arms. Optionally, these arms may be utilized in order to position one or more cameras in a position suitable for taking images of certain regions of the face. FIG. 18 illustrates right and left clip-on devices that include bodies 153 and 154, respectively, which are configured to attached/detached from an eyeglasses frame. These bodies have protruding arms that hold the head-mounted cameras. Head-mounted camera 155 measures a region on the lower part of the face, head-mounted camera 156 measures regions on the forehead. The left clip-on device also includes other electronics 157 (such as a processor, a battery, and/or a wireless communication module). The clip-on devices illustrated in this figure may include additional cameras illustrated in the drawings as black circles.

In other embodiments, at least a certain portion of the clip-on device is located behind the eyeglasses' frame. Thus, when the clip-on device is attached to the eyeglasses, they may remain aesthetically pleasing, and attaching the clip-on device may cause little or no blocking of the user's vision. FIG. 16b and FIG. 17b illustrate two examples of clip-on devices that are mostly attached behind the frame. The following are some additional examples of embodiments in which a portion of the clip-on device may be located behind the frame.

FIG. 16a and FIG. 16b illustrate two, right and left, clip-on devices with bodies 160 and 161, respectively, configured to be attached behind an eyeglasses frame 165. The body 160 has various components fixed to it which include: an inward-facing head-mounted camera 162 pointed at a region below eye-level (such as the upper lip, mouth, nose, and/or cheek), an inward-facing head-mounted camera 163 pointed at a region above eye-level (such as the forehead), and other electronics 164 (such as a processor, a battery, and/or a wireless communication module). The right and left clip-on devices may include additional cameras illustrated in the drawings as black circles.

FIG. 17a and FIG. 17b illustrate a single-unit clip-on device that includes the body 170, which is configured to be attached behind the eyeglasses frame 176. The body 170 has various cameras fixed to it, such as head-mounted cameras 171 and 172 that are pointed at regions on the lower part of the face (such as the upper lip, mouth, nose, and/or cheek), and head-mounted cameras 173 and 174 that are pointed at the forehead. The spring 175 is configured to apply force that holds the body 170 to the frame 176. Other electronics 177 (such as a processor, a battery, and/or a wireless communication module), may also be fixed to the body 170. The clip-on device may include additional cameras illustrated in the drawings as black circles.

In one embodiment, when the body is attached to the eyeglasses, more than 50% of the out-facing surface of the clip-on device is located behind the eyeglasses frame. Optionally, a portion of the clip-on device that is located behind the eyeglasses frame is occluded from a viewer positioned directly opposite to the eyeglasses, at the same height as the eyeglasses. Thus, a portion of the clip-on device that is behind the frame might not be visible to other people from many angles, which can make the clip-on device less conspicuous and/or more aesthetically pleasing. Optionally, a larger portion of the clip-on device is behind the frame when the body is attached to the eyeglasses, such as more than 75% or 90% of the out-facing surface.

Various physiological responses may be detected based on Facial skin color changes (FSCC) that occur on a user's face. In one embodiment, a system configured to detect a physiological response based on FSCC includes at least an inward-facing head-mounted visible-light camera ($VCAM_{in}$) and a computer. The system may optionally include additional elements such as a frame and additional inward-facing camera(s) and/or outward-facing camera(s).

Figure 24:
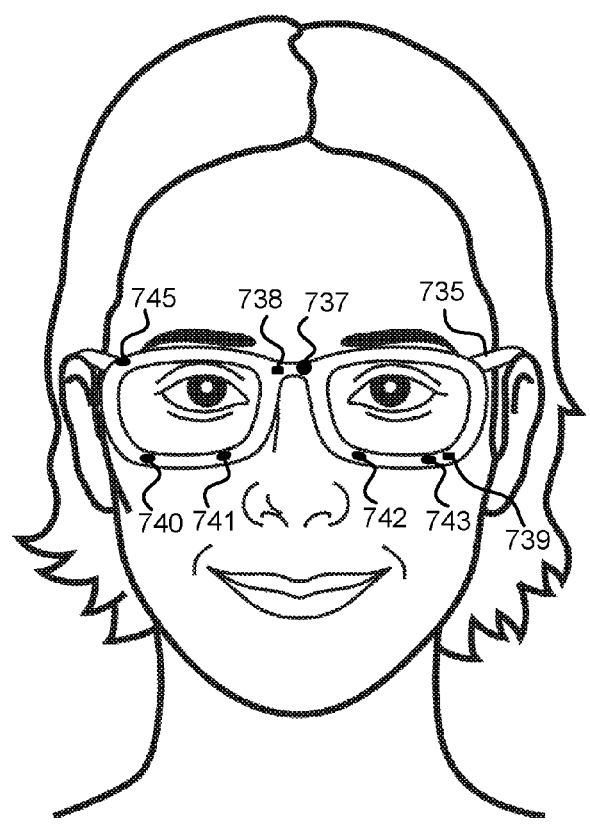
FIG. 24 illustrates an embodiment of the system configured to detect a physiological response based on facial skin color changes (FSCC)

FIG. 24 illustrates one embodiment of the system configured to detect a physiological response based on FSCC. The system includes a frame 735 (e.g., an eyeglasses frame) to which various cameras are physically coupled. These cameras include visible-light cameras 740, 741, 742, and 743, which may each take images of regions on the user's cheeks and/or nose. Each of these cameras may possibly be $VCAM_{in}$, which is discussed in more detail below. Another possibility for $VCAM_{in}$ is camera 745 that takes images of a region on the user's forehead and is coupled to the upper portion of the frame. Visible-light camera 737, which takes images of the environment ($IM_{ENV}$), is an example of $VCAM_{out}$ discussed below, which may optionally be included in some embodiments. Additional cameras that may optionally be included in some embodiments are outward-facing thermal camera 738 (which may be used to take $TH_{ENV}$ mentioned below) and inward-facing thermal camera 739 (which may be used to take $TH_{ROI2}$ mentioned below).

$VCAM_{in}$ is worn on the user's head and takes images of a region of interest ($IM_{ROI}$) on the user's face. Depending on the physiological response being detected, the ROI may cover various regions on the user's face. In one example, the ROI is on a cheek of the user, a region on the user's nose, and/or a region on the user's forehead. Optionally, $VCAM_{in}$ does not occlude the ROI, is located less than 10 cm from the user's face, and weighs below 10 g. The ROI is illuminated by ambient light. Optionally, the system does not occlude the ROI, and the ROI is not illuminated by a head-mounted light source. Alternatively, the ROI may be illuminated by a head-mounted light source that is weaker than the ambient light.

The computer detects the physiological response based on $IM_{ROI}$ by relying on effects of FSCC that are recognizable in $IM_{ROI}$. Herein, sentences of the form "FSCC recognizable in $IM_{ROI}$" refer to effects of FSCC that may be identified and/or utilized by the computer, which are usually not recognized by the naked eye. The FSCC phenomenon may be utilized to detect various types of physiological responses. In one embodiment, the physiological response that is detected may involve an expression of emotional response of the user. For example, the computer may detect whether the user's emotional response is neutral, positive, or negative. In another example, the computer may detect an emotional response that falls into a more specific category such as distress, happiness, anxiousness, sadness, frustration, intrigue, joy, disgust, anger, etc. Optionally, the expression of the emotional response may involve the user making a facial expression and/or a microexpression (whose occurrence may optionally be detected based on $IM_{ROI}$). In another embodiment, detecting the physiological response involves determining one or more physiological signals of the user, such as a heart rate (which may also be referred to as "cardiac pulse"), heart rate variability, and/or a breathing rate.

$IM_{ROI}$ are images generated based on ambient light illumination that is reflected from the user's face. Variations in the reflected ambient light may cause FSCC that are unrelated to the physiological response being detected, and thus possibly lead to errors in the detection of the physiological response. In some embodiments, the system includes an outward-facing head-mounted visible-light camera ($VCAM_{out}$), which is worn on the user's head, and takes images of the environment ($IM_{ENV}$). Optionally, $VCAM_{out}$ is located less than 10 cm from the user's face and weighs below 10 g. Optionally, $VCAM_{out}$ may include optics that provide it with a wide field of view. Optionally, the computer detects the physiological response based on both $IM_{ROI}$ and $IM_{ENV}$. Given that $IM_{ENV}$ is indicative of illumination towards the face and $IM_{ROI}$ is indicative of reflections from the face, utilizing $IM_{ENV}$ in the detection of the physiological response can account, at least in part, for variations in ambient light that, when left unaccounted, may possibly lead to errors in detection of the physiological response.

It is noted that the system may include multiple $VCAM_{in}$ configured to take images of various ROIs on the face, $IM_{ROI}$ may include images taken from the multiple $VCAM_{in}$, and multiple $VCAM_{out}$ located at different locations and/or orientation relative to the face may be used to take images of the environment.

In some embodiments, $VCAM_{in}$ and/or $VCAM_{out}$ are physically coupled to a frame, such as an eyeglasses frame or an augmented realty device frame. Optionally, the angle between the optical axes of $VCAM_{in}$ and $VCAM_{out}$ is known to the computer, and may be utilized in the detection of the physiological response. Optionally, the angle between the optical axes of $VCAM_{in}$ and $VCAM_{out}$ is fixed.

Due to the proximity of $VCAM_{in}$ to the face, in some embodiments, there may be an acute angle between the optical axis of $VCAM_{in}$ and the ROI (e.g., when the ROI includes a region on the forehead). In order to improve the sharpness of $IM_{ROI}$, $VCAM_{in}$ may be configured to operate in a way that takes advantage of the Scheimpflug principle. In one embodiment, $VCAM_{in}$ includes a sensor and a lens; the sensor plane is tilted by a fixed angle greater than 2° relative to the lens plane according to the Scheimpflug principle in order to capture a sharper image when $VCAM_{in}$ is worn by the user (where the lens plane refers to a plane that is perpendicular to the optical axis of the lens, which may include one or more lenses). Optionally, $VCAM_{in}$ does not occlude the ROI. In another embodiment, $VCAM_{in}$ includes a sensor, a lens, and a motor; the motor tilts the lens relative to the sensor according to the Scheimpflug principle. The tilt improves the sharpness of $IM_{ROI}$ when $VCAM_{in}$ is worn by the user.

In addition to capturing images in the visible spectrum, some embodiments may involve capturing light in the near infrared spectrum (NIR). In some embodiments, $VCAM_{in}$ and/or VCAM$_{out}$ may include optics and sensors that capture light rays in at least one of the following NIR spectrum intervals: 700-800 nm, 700-900 nm, 700-1,000 nm. Optionally, the computer may utilize data obtained in a NIR spectrum interval to detect the physiological response (in addition to or instead of data obtained from the visible spectrum). Optionally, the sensors may be CCD sensors designed to be sensitive in the NIR spectrum and/or CMOS sensors designed to be sensitive in the NIR spectrum.

One advantage of having VCAM$_{in}$ coupled to the frame involves the handling of chromatic aberrations. Chromatic aberrations refract different wavelengths of light at different angles, depending on the incident angle. When VCAM$_{in}$ is physically coupled to the frame, the angle between VCAM$_{in}$ and the ROI is known, and thus the computer may be able to select certain subsets of pixels, which are expected to measure light of certain wavelengths from the ROI. In one embodiment, VCAM$_{in}$ includes a lens and a sensor comprising pixels; the lens generates chromatic aberrations that refract red and blue light rays in different angles; the computer selects, based on the angle between the camera and the ROI (when the user wears the frame), a first subset of pixels to measure the blue light rays reflected from the ROI, and a second subset of pixels to measure the red light rays reflected from the ROI. Optionally, the first and second subsets are not the same. Optionally, VCAM$_{in}$ may include a sensor that captures light rays also in a portion of the NIR spectrum, and the computer selects, based on the angle between VCAM$_{in}$ and the ROI, a third subset of pixels to measure the NIR light rays reflected from the ROI. Optionally, the second and third subsets are not the same.

The computer may utilize various approaches in order to detect the physiological response based on IM$_{ROI}$. Some examples of how such a detection may be implemented are provided in the prior art references mentioned above, which rely on FSCC to detect the physiological response. It is to be noted that while the prior art approaches involve analysis of video obtained from cameras that are not head-mounted, are typically more distant from the ROI than VCAM$_{in}$, and are possibly at different orientations relative to the ROI, the computational approaches described in the prior art used to detect physiological responses can be readily adapted by one skilled in the art to handle IM$_{ROI}$. In some cases, embodiments described herein may provide video in which a desired signal is more easily detectable compared to some of the prior art approaches. For example, given the short distance from VCAM$_{in}$ to the ROI, the ROI is expected to cover a larger portion of the images in IM$_{ROI}$ compared to images obtained by video cameras in some of the prior art references. Additionally, due to the proximity of VCAM$_{in}$ to the ROI, additional illumination that is required in some prior art approaches, such as illuminating the skin for a pulse oximeter to obtain a photoplethysmographic (PPG) signal, may not be needed. Furthermore, given VCAM$_{in}$'s fixed location and orientation relative to the ROI (even when the user makes lateral and/or angular movements), many pre-processing steps that need to be implemented by the prior art approaches, such as image registration and/or face tracking, are extremely simplified in embodiments described herein, or may be foregone altogether.

IM$_{ROI}$ may undergo various preprocessing steps prior to being used by the computer to detect the physiological response and/or as part of the process of the detection of the physiological response. Some non-limiting examples of the preprocessing include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081. Additionally or alternatively, some embodiments may involve generating feature values based on a single image or a sequence of images. In some examples, generation of feature values from one or more images may involve utilization of some of the various approaches described in this disclosure for generation of high-level and/or low-level image-based features.

The following is a discussion of some approaches that may be utilized by the computer to detect the physiological response based on IM$_{ROI}$. Additionally, implementation-related details may be found in the provided references and the references cited therein. Optionally, IM$_{ENV}$ may also be utilized by the computer to detect the physiological response (in addition to IM$_{ROI}$), as explained in more detail below.

In some embodiments, the physiological response may be detected using signal processing and/or analytical approaches. Optionally, these approaches may be used for detecting repetitive physiological signals (e.g., a heart rate, heart rate variability, or a breathing rate) in IM$_{ROI}$ taken during a certain period. Optionally, the detected physiological response represents the value of the physiological signal of the user during the certain period.

In one example, U.S. Pat. No. 8,768,438, titled "Determining cardiac arrhythmia from a video of a subject being monitored for cardiac function", describes how a heart rate may be determined based on FSCC, which are represented in a PPG signal obtained from video of the user. In this example, a time series signal is generated from video images of a subject's exposed skin, and a reference signal is used to perform a constrained source separation (which is a variant of ICA) on the time series signals to obtain the PPG signal. Peak-to-peak pulse points are detected in the PPG signal, which may be analyzed to determine parameters such as heart rate, heart rate variability, and/or to obtain peak-to-peak pulse dynamics that can be indicative of conditions such as cardiac arrhythmia.

In another example, U.S. Pat. No. 8,977,347, titled "Video-based estimation of heart rate variability", describes how a times-series signal similar to the one described above may be subjected to a different type of analysis to detect the heart rate variability. In this example, the time series data are de-trended to remove slow non-stationary trends from the signal and filtered (e.g., using bandpass filtering). Following that, low frequency and high frequency components of the integrated power spectrum within the time series signal are extracted using Fast Fourier Transform (FFT). A ratio of the low and high frequency of the integrated power spectrum within these components is computed. And analysis of the dynamics of this ratio over time is used to estimate heart rate variability.

In yet another example, U.S. Pat. No. 9,020,185, titled "Systems and methods for non-contact heart rate sensing", describes how a times-series signals obtained from video of a user can be filtered and processed to separate an underlying pulsing signal by, for example, using an ICA algorithm. The separated pulsing signal from the algorithm can be transformed into frequency spacing data using FFT, in which the heart rate can be extracted or estimated.

In some embodiments, the physiological response may be detected using machine learning-based methods. Optionally, these approaches may be used for detecting expressions of emotions and/or values of physiological signals.

Generally, machine learning-based approaches involve training a model on samples, with each sample including: feature values generated based on IM$_{ROI}$ taken during a certain period, and a label indicative of the physiological response during the certain period. Optionally, the model may be personalized for a user by training the model on samples including: feature values generated based on $IM_{ROI}$ of the user, and corresponding labels indicative of the user's respective physiological responses. Some of the feature values in a sample may be generated based on other sources of data (besides $IM_{ROI}$), such as measurements of the user generated using thermal cameras, movement sensors, and/or other physiological sensors, and/or measurements of the environment. Optionally, $IM_{ROI}$ of the user taken during an earlier period may serve as a baseline to which to compare. Optionally, some of the feature values may include indications of confounding factors, which may affect FSCC, but are unrelated to the physiological response being detected. Some examples of confounding factors include touching the face, thermal radiation directed at the face, and consuming certain substances such as a medication, alcohol, caffeine, or nicotine.

Training the model may involve utilization of various training algorithms known in the art (e.g., algorithms for training neural networks and/or other approaches described herein). After the model is trained, feature values may be generated for $IM_{ROI}$ for which the label (physiological response) is unknown, and the computer can utilize the model to detect the physiological response based on these feature values.

It is to be noted that in some embodiments, the model is trained based on data that includes measurements of the user, in which case it may be considered a personalized model of the user. In other embodiments, the model is trained based on data that includes measurements of one or more other users, in which case it may be considered a general model.

In order to achieve a robust model, which may be useful for detecting the physiological response in various conditions, in some embodiments, the samples used in the training may include samples based on $IM_{ROI}$ taken in different conditions and include samples with various labels (e.g., expressing or not expressing certain emotions, or different values of physiological signals). Optionally, the samples are generated based on $IM_{ROI}$ taken on different days.

The following are four examples of different compositions of samples that may be used when training the model in different embodiments. The "measured user" in the four examples below may be "the user" who is mentioned above (e.g., when the model is a personalized model that was trained on data that includes measurements of the user), or a user from among one or more other users (e.g., when the model is a general model that was trained on data that includes measurements of the other users). In a first example, the system does not occlude the ROI, and the model is trained on samples generated from a first set of $IM_{ROI}$ taken while the measured user was indoors and not in direct sunlight, and is also trained on other samples generated from a second set of $IM_{ROI}$ taken while the measured user was outdoors, in direct sunlight. In a second example, the model is trained on samples generated from a first set of $IM_{ROI}$ taken during daytime, and is also trained on other samples generated from a second set of $IM_{ROI}$ taken during nighttime. In a third example, the model is trained on samples generated from a first set of $IM_{ROI}$ taken while the measured user was exercising and moving, and is also trained on other samples generated from a second set of $IM_{ROI}$ taken while the measured user was sitting and not exercising. And a fourth example, the model is trained on samples generated from a first set of $IM_{ROI}$ taken less than 30 minutes after the measured user had an alcoholic beverage, and is also trained on other samples generated from a second set of $IM_{ROI}$ taken on a day in which the measured user did not have an alcoholic beverage.

Labels for the samples may be obtained from various sources. In one embodiment, the labels may be obtained utilizing one or more sensors that are not $VCAM_{in}$. In one example, a heart rate and/or heart rate variability may be measured using an ECG sensor. In another example, the breathing rate may be determined using a smart shirt with sensors attached to the chest (e.g., a smart shirt by Hexoskin®). In yet another example, a type emotional response of the user may be determined based on analysis of a facial expression made by the user, analysis of the user's voice, analysis of thermal measurements of regions of the face of the user, and/or analysis of one or more of the following sensor-measured physiological signals of the user: a heart rate, heart rate variability, breathing rate, and galvanic skin response.

In another embodiment, a label describing an emotional response of the user may be inferred. In one example, the label may be based on semantic analysis of a communication of the user, which is indicative of the user's emotional state at the time $IM_{ROI}$ were taken. In another example, the label may be generated in a process in which the user is exposed to certain content, and a label is determined based on an expected emotional response corresponding to the certain content (e.g., happiness is an expected response to a nice image while distress is an expected response to a disturbing image).

Due to the nature of the physiological responses being detected and the type of data (video images), a machine learning approach that may be applied in some embodiments is "deep learning". In one embodiment, the model may include parameters describing multiple hidden layers of a neural network. Optionally, the model may include a convolution neural network (CNN). In one example, the CNN may be utilized to identify certain patterns in the video images, such as the patterns of the reflected FSCC due to the physiological response. Optionally, detecting the physiological response may be done based on multiple, possibly successive, images that display a certain pattern of change over time (i.e., across multiple frames), which characterizes the physiological response being detected. Thus, detecting the physiological response may involve retaining state information that is based on previous images. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

Some of the prior art references mentioned herein provide additional detailed examples of machine learning-based approaches that may be utilized to detect the physiological response (especially in the case in which it corresponds to an emotional response). In one example, Ramirez, et al. ("Color analysis of facial skin: Detection of emotional state") describe detection of an emotional state using various machine learning algorithms including decision trees, multinomial logistic regression, and latent-dynamic conditional random fields. In another example, Wang, et al. ("Microexpression recognition using color spaces") describe various feature extraction methods and pixel color value transformations, which are used to generate inputs for a support vector machine (SVM) classifier trained to identify microexpressions.

As mentioned above, in some embodiments, $IM_{ENV}$ may be utilized in the detection of the physiological response to account, at least in part, for illumination interferences that may lead to errors in the detection of the physiological response. There are different ways in which $IM_{ENV}$ may be utilized for this purpose.

In one embodiment, when variations in $IM_{ENV}$ reach a certain threshold (e.g., which may correspond to ambient light variations above a certain extent), the computer may refrain from detecting the physiological response.

In another embodiment, $IM_{ENV}$ may be utilized to normalize $IM_{ROI}$ with respect to the ambient light. For example, the intensity of pixels in $IM_{ROI}$ may be adjusted based on the intensity of pixels in $IM_{ENV}$ when $IM_{ROI}$ were taken. US patent application number 20130215244 describes a method of normalization in which values of pixels from a region that does not contain a signal (e.g., background regions that include a different body part of the user or an object behind the user) are subtracted from regions of the image that contain the signal of the physiological response. While the computational approach described therein may be applied to embodiments in this disclosure, the exact setup described therein may not work well in some cases due to the close proximity of $VCAM_{in}$ to the face and the fact that $VCAM_{in}$ is head-mounted. Thus, it may be advantageous to subtract a signal from the environment ($IM_{ENV}$) that is obtained from $VCAM_{out}$, which may more accurately represent the ambient light illuminating the face.

It is to be noted that training data that includes a ground-truth signal (i.e., values of the true physiological response corresponding to $IM_{ROI}$ and $IM_{ENV}$) may be utilized to optimize the normalization procedure used to correct $IM_{ROI}$ with respect to the ambient light measured in $IM_{ENV}$. For example, such optimization may be used to determine parameter values of a function that performs the subtraction above, which lead to the most accurate detections of the physiological response.

In still another embodiment, $IM_{ENV}$ may be utilized to generate feature values in addition to $IM_{ROI}$. Optionally, at least some of the same types of feature values generated based on $IM_{ROI}$ may also be generated based on $IM_{ENV}$. Optionally, at least some of the feature values generated based on $IM_{ENV}$ may relate to portions of images, such as average intensity of patches of pixels in $IM_{ENV}$.

By utilizing $IM_{ENV}$ as inputs used for the detection of the physiological response, a machine learning-based model may be trained to be robust, and less susceptible, to environmental interferences such as ambient light variations. For example, if the training data used to train the model includes samples in which no physiological response was present (e.g., no measured emotional response or microexpression was made), but some ambient light variations might have introduced some FSCC-related signal, the model will be trained such that feature values based on $IM_{ENV}$ are used to account for such cases. This can enable the computer to negate, at least in part, the effects of such environmental interferences, and possibly make more accurate detections of the physiological response.

In one embodiment, the computer receives an indication indicative of the user consuming a confounding substance that is expected to affect FSCC (e.g., alcohol, drugs, certain medications, and/or cigarettes). The computer detects the physiological response, while the consumed confounding substance affects FSCC, based on: $IM_{ROI}$, the indication, and a model that was trained on: a first set of $IM_{ROI}$ taken while the confounding substance affected FSCC, and a second set of $IM_{ROI}$ taken while the confounding substance did not affect FSCC.

Prior art FSCC systems are sensitive to user movements and do not operate well while the user is running. This is because state-of-the-art FSCC systems use hardware and automatic image trackers that are not accurate enough to crop correctly the ROI from the entire image while running, and the large errors in cropping the ROI are detrimental to the performances of the FSCC algorithms. Contrary to the prior art FSCC systems, the disclosed $VCAM_{in}$ remains pointed at its ROI also when the user's head makes angular and lateral movements, and thus the complicated challenges related to image registration and ROI tracking are much simplified or even eliminated. Therefore, systems based on $VCAM_{in}$ (such as the one illustrated in FIG. 24) may detect the physiological response (based on FSCC) also while the user is running.

$VCAM_{in}$ may be pointed at different regions on the face. In a first embodiment, the ROI is on the forehead, $VCAM_{in}$ is located less than 10 cm from the user's face, and optionally the optical axis of $VCAM_{in}$ is above 20° from the Frankfort horizontal plane. In a second embodiment, the ROI is on the nose, and $VCAM_{in}$ is located less than 10 cm from the user's face. Because $VCAM_{in}$ is located close to the face, it is possible to calculate the FSCC based on a small ROI, which is irrelevant to the non-head-mounted prior arts that are limited by the accuracy of their automatic image tracker. In a third embodiment, $VCAM_{in}$ is pointed at an eye of the user. The computer selects the sclera as the ROI and detects the physiological response based on color changes recognizable in $IM_{ROI}$ of the sclera. In a fourth embodiment, $VCAM_{in}$ is pointed at an eye of the user. The computer selects the iris as the ROI and detects the physiological response based on color changes recognizable in $IM_{ROI}$ of the iris. Optionally, the computer further calculates changes to the pupil diameter based on the $IM_{ROI}$ of the iris, and detects an emotional response of the user based on the changes to the pupil diameter.

In order to improve the detection accuracy, and in some cases in order to better account for interferences, the computer may utilize measurements of one or more head-mounted thermal cameras in the detection of the physiological response. In one embodiment, the system may include an inward-facing head-mounted thermal camera that takes thermal measurements of a second ROI ($TH_{ROI2}$) on the user's face. Optionally, ROI and $ROI_2$ overlap, and the computer utilizes $TH_{ROI2}$ to detect the physiological response. Optionally, on average, detecting the physiological response based on both FSCC recognizable in $IM_{ROI}$ and $TH_{ROI2}$ is more accurate than detecting the physiological response based on the FSCC without $TH_{ROI2}$. Optionally, the computer utilizes $TH_{ROI2}$ to account, at least in part, for temperature changes, which may occur due to physical activity and/or consumption of certain medications that affect the blood flow. Optionally, the computer utilizes $TH_{ROI2}$ by generating feature values based on $TH_{ROI2}$, and utilizing a model that was trained on data comprising $TH_{ROI2}$ in order to detect the physiological response.

In another embodiment, the system may include an outward-facing head-mounted thermal camera that takes thermal measurements of the environment ($TH_{ENV}$). Optionally, the computer may utilize $TH_{ENV}$ to detect the physiological response (e.g., by generating feature values based on $TH_{ENV}$ and utilizing a model trained on data comprising $TH_{ENV}$).

Optionally, on average, detecting the physiological response based on both FSCC recognizable in $IM_{ROI}$ and $TH_{ENV}$ is more accurate than detecting the physiological response based on the FSCC without $TH_{ENV}$. Optionally, the computer utilizes $TH_{ENV}$ to account, at least in part, for thermal interferences from the environment, such as direct sunlight and/or a nearby heater.

In addition to detecting a physiological response, in some embodiments, the computer may utilize $IM_{ROI}$ to generate an avatar of the user (e.g., in order to represent the user in a virtual environment). Optionally, the avatar may express emotional responses of the user, which are detected based on $IM_{ROI}$. Optionally, the computer may modify the avatar of the user to show synthesized facial expressions that are not manifested in the user's actual facial expressions. In one embodiment, the synthesized facial expressions correspond to emotional responses detected based on FSCC that are recognizable in $IM_{ROI}$. In another embodiment, the synthesized facial expressions correspond to emotional responses detected based on thermal measurements taken by CAM. Some of the various approaches that may be utilized to generate the avatar based on $IM_{ROI}$ are described in co-pending US patent publication 2016/0360970.

The following method for detecting a physiological response based on facial skin color changes (FSCC) may be used by systems modeled according to FIG. 24. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking images of a region of interest ($IM_{ROI}$) on a user's face utilizing an inward-facing head-mounted visible-light camera ($VCAM_{in}$). The ROI is illuminated by ambient light.

And in Step 2, detecting the physiological response based on FSCC recognizable in $IM_{ROI}$. Optionally, detecting the physiological response involves generating feature values based on $IM_{ROI}$ and utilizing a model to calculate, based on the feature values, a value indicative of an extent of the physiological response. Optionally, the model was trained based on $IM_{ROI}$ of the user taken during different days.

In one embodiment, the method may optionally include a step of taking images of the environment ($IM_{ENV}$) utilizing an outward-facing head-mounted visible-light camera ($VCAM_{out}$). Optionally, detecting the physiological response is also based on $IM_{ENV}$.

Normally, the lens plane and the sensor plane of a camera are parallel, and the plane of focus (PoF) is parallel to the lens and sensor planes. If a planar object is also parallel to the sensor plane, it can coincide with the PoF, and the entire object can be captured sharply. If the lens plane is tilted (not parallel) relative to the sensor plane, it will be in focus along a line where it intersects the PoF. The Scheimpflug principle is a known geometric rule that describes the orientation of the plane of focus of a camera when the lens plane is tilted relative to the sensor plane.

Figure 20A:
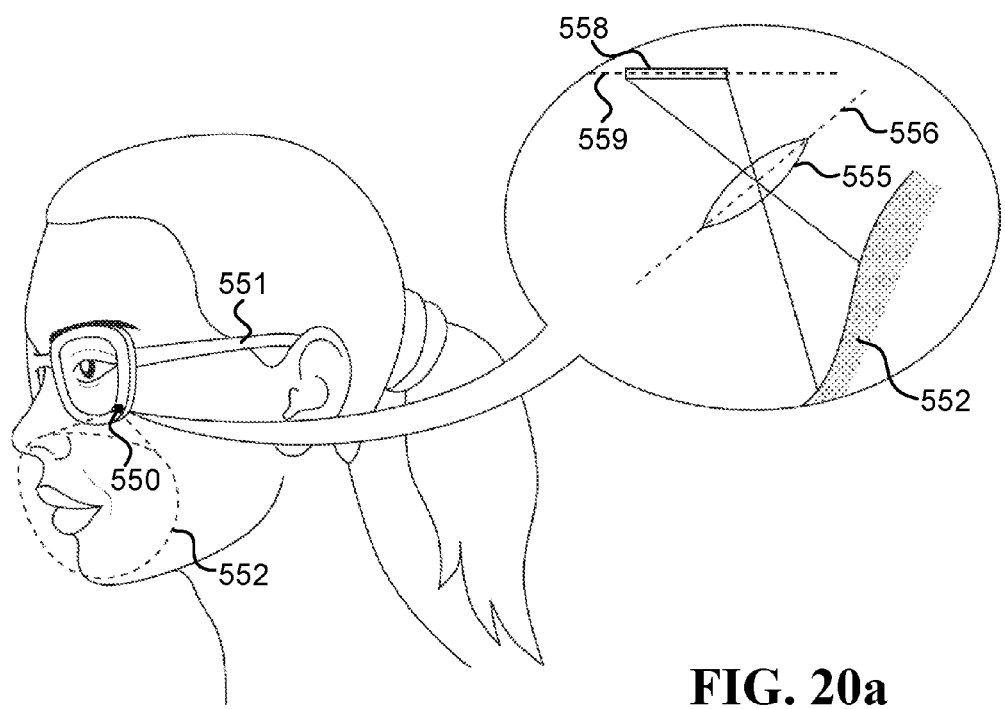
FIG. 20a is a schematic illustration of an inward-facing head-mounted camera embedded in an eyeglasses frame, which utilizes the Scheimpflug principle.

FIG. 20a is a schematic illustration of an inward-facing head-mounted camera 550 embedded in an eyeglasses frame 551, which utilizes the Scheimpflug principle to improve the sharpness of the image taken by the camera 550. The camera 550 includes a sensor 558 and a lens 555. The tilt of the lens 555 relative to sensor 558, which may also be considered as the angle between the lens plane 555 and the sensor plane 559, is determined according to the expected position of the camera 550 relative to the ROI 552 when the user wears the eyeglasses. For a refractive optical lens, the "lens plane" 556 refers to a plane that is perpendicular to the optical axis of the lens 555. Herein, the singular also includes the plural, and the term "lens" refers to one or more lenses. When "lens" refers to multiple lenses (which is usually the case in most modern cameras having a lens module with multiple lenses), then the "lens plane" refers to a plane that is perpendicular to the optical axis of the lens module.

Figure 20B:
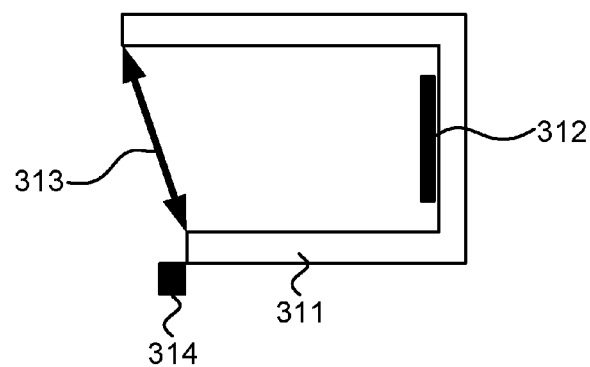
FIG. 20b is a schematic illustration of a camera that is able to change the relative tilt between its lens and sensor planes according to the Scheimpflug principle.

The Scheimpflug principle may be used for both thermal cameras (based on lenses and sensors for wavelengths longer than 2500 nm) and visible-light and/or near-IR cameras (based on lenses and sensors for wavelengths between 400-900 nm). FIG. 20b is a schematic illustration of a camera that is able to change the relative tilt between its lens and sensor planes according to the Scheimpflug principle. Housing 311 mounts a sensor 312 and lens 313. The lens 313 is tilted relative to the sensor 312. The tilt may be fixed according to the expected position of the camera relative to the ROI when the user wears the HMS, or may be adjusted using motor 314. The motor 314 may move the lens 313 and/or the sensor 312.

In one embodiment, an HMS device includes a frame configured to be worn on a user's head, and an inward-facing camera physically coupled to the frame. The inward-facing camera may assume one of two configurations: (i) the inward-facing camera is oriented such that the optical axis of the camera is above the Frankfort horizontal plane and pointed upward to capture an image of a region of interest (ROI) above the user's eyes, or (ii) the inward-facing camera is oriented such that the optical axis is below the Frankfort horizontal plane and pointed downward to capture an image of an ROI below the user's eyes. The inward-facing camera includes a sensor and a lens. The sensor plane is tilted by more than 2° relative to the lens plane according to the Scheimpflug principle in order to capture a sharper image.

In another embodiment, an HMS includes an inward-facing head-mounted camera that captures an image of an ROI on a user's face, when worn on the user's head. The ROI is on the user's forehead, nose, upper lip, cheek, and/or lips. The camera includes a sensor and a lens. And the sensor plane is tilted by more than 2° relative to the lens plane according to the Scheimpflug principle in order to capture a sharper image.

Because the face is not planar and the inward-facing head-mounted camera is located close to the face, an image captured by a camera having a wide field of view (FOV) and a low f-number may not be perfectly sharp, even after applying the Scheimpflug principle. Therefore, in some embodiments, the tilt between the lens plane and the sensor plane is selected such as to adjust the sharpness of the various areas covered in the ROI according to their importance for detecting the user's physiological response (which may be the user's emotional response in some cases). In one embodiment, the ROI covers first and second areas, where the first area includes finer details and/or is more important for detecting the physiological response than the second area. Therefore, the tilt between the lens and sensor planes is adjusted such that the image of the first area is shaper than the image of the second area.

In another embodiment, the ROI covers both a first area on the upper lip and a second area on a cheek, and the tilt is adjusted such that the image of the first area is shaper than the image of the second area, possibly because the upper lip usually provides more information and has more details relative to the cheek.

In still another embodiment, the ROI covers both a first area on the upper lip and a second area on the nose, and the tilt is adjusted such that the image of the first area is shaper than the image of the second area, possibly because the upper lip usually provides more information relative to the nose.

In still another embodiment, the ROI covers a first area on the cheek straight above the upper lip, a second area on the cheek from the edge of the upper lip towards the ear, and a third area on the nose. And the tilt between the lens plane and the sensor plane is adjusted such that the image of the first area is shaper than both the images of the second and third areas.

In still another embodiment, the ROI covers both a first area on the lips and a second area on the chin, and the tilt is adjusted such that the image of the first area is shaper than the image of the second area, possibly because the lips usually provides more information than the chin.

In still another embodiment, the camera is a visible-light camera, and the ROI covers both a first area on the lower forehead (including an eyebrow) and a second area on the upper forehead, and the tilt is adjusted such that the image of the first area is shaper than the image of the second area, possibly because the eyebrow provides more information about the user's emotional response than the upper forehead.

In still another embodiment, the camera is a thermal camera, and the ROI covers an area on the forehead, and the tilt is adjusted such that the image of a portion of the middle and upper part of the forehead (below the hair line) is shaper than the image of a portion of the lower part of the forehead, possibly because the middle and upper parts of the forehead are more indicative of prefrontal cortex activity than the lower part of the forehead, and movements of the eyebrows disturb the thermal measurements of the lower part of the forehead.

In one embodiment, the tilt between the lens plane and sensor plane is fixed. The fixed tilt is selected according to an expected orientation between the camera and the ROI when a user wears the frame. Having a fixed tilt between the lens and sensor planes may eliminate the need for an adjustable electromechanical tilting mechanism. As a result, a fixed tilt may reduce the weight and cost of the camera, while still providing a sharper image than an image that would be obtained from a similar camera in which the lens and sensor planes are parallel. The magnitude of the fixed tilt may be selected according to facial dimensions of an average user expected to wear the system, or according to a model of the specific user expected to wear the system in order to obtain the sharpest image.

In another embodiment, the system includes an adjustable electromechanical tilting mechanism configured to change the tilt between the lens and sensor planes according to the Scheimpflug principle based on the orientation between the camera and the ROI when the frame is worn by the user. The tilt may be achieved using at least one motor, such as a brushless DC motor, a stepper motor (without a feedback sensor), a brushed DC electric motor, a piezoelectric motor, and/or a micro-motion motor.

The adjustable electromechanical tilting mechanism configured to change the tilt between the lens and sensor planes may include one or more of the following mechanisms: (i) a mirror that changes its angle; (ii) a device that changes the angle of the lens relative to the sensor; and/or (iii) a device that changes the angle of the sensor relative to the lens. In one embodiment, the camera, including the adjustable electromechanical tilting mechanism, weighs less than 10 g, and the adjustable electromechanical tilting mechanism is able to change the tilt in a limited range below 30° between the two utmost orientations between the lens and sensor planes. Optionally, the adjustable electromechanical tilting mechanism is able to change the tilt in a limited range below 20° between the two utmost orientations between the lens and sensor planes. In another embodiment, the adjustable electromechanical tilting mechanism is able to change the tilt in a limited range below 10°. In some embodiments, being able to change the tilt in a limited range reduces at least one of the weight, cost, and size of the camera, which is advantageous for a wearable device. In one example, the camera is manufactured with a fixed predetermined tilt between the lens and sensor planes, which is in addition to the tilt provided by the adjustable electromechanical tilting mechanism. The fixed predetermined orientation may be determined according to the expected orientation between the camera and the ROI for an average user, such that the adjustable electromechanical tilting mechanism is used to fine-tune the tilt between the lens and sensor planes for the specific user who wears the frame and has facial dimensions that are different from the average user.

Various types of cameras may be utilized in different embodiments described herein. In one embodiment, the camera is a thermal camera that takes thermal measurements of the ROI with a focal plane array thermal sensor having an angle above 2° between the lens and sensor planes. Optionally, the thermal camera weighs below 10 g, is located less than 10 cm from the user's face, and the tilt of the lens plane relative to the sensor plane is fixed. The fixed tilt is selected according to an expected orientation between the camera and the ROI when the user wears the frame. Optionally, the system includes a computer to detect a physiological response based on the thermal measurements. Optionally, the computer processes time series measurements of each sensing element individually to detect the physiological response.

In another embodiment, the camera is a visible-light camera that takes visible-light images of the ROI, and a computer generates an avatar for the user based on the visible-light images. Some of the various approaches that may be utilized to generate the avatar based on the visible-light images are described in co-pending US patent publication 2016/0360970. Additionally or alternatively, the computer may detect an emotional response of the user based on (i) facial expressions in the visible-light images utilizing image processing, and/or (ii) facial skin color changes (FSCC), which result from concentration changes of hemoglobin and/or oxygenation.

It is to be noted that there are various approaches known in the art for identifying facial expressions from images. While many of these approaches were originally designed for full-face frontal images, those skilled in the art will recognize that algorithms designed for full-face frontal images may be easily adapted to be used with images obtained using the inward-facing head-mounted visible-light cameras disclosed herein. For example, the various machine learning techniques described in prior art references may be applied to feature values extracted from images that include portions of the face from orientations that are not directly in front of the user. Furthermore, due to the closeness of the visible-light cameras to the face, facial features are typically larger in images obtained by the systems described herein. Moreover, challenges such as image registration and face tracking are vastly simplified and possibly non-existent when using inward-facing head-mounted cameras. The reference Zeng, Zhihong, et al. "A survey of affect recognition methods: Audio, visual, and spontaneous expressions."

IEEE transactions on pattern analysis and machine intelligence 31.1 (2009): 39-58, describes some of the algorithmic approaches that may be used for this task. The following references discuss detection of emotional responses based on FSCC: (i) Ramirez, Geovany A., et al. "Color analysis of facial skin: Detection of emotional state" in Proceedings of the IEEE Conference on Computer Vision and Pattern Recognition Workshops, 2014; and (ii) Wang, Su-Jing, et al. "Micro-expression recognition using color spaces", in IEEE Transactions on Image Processing 24.12 (2015): 6034-6047.

In still another embodiment, the camera is a light field camera that implements a predetermined blurring at a certain Scheimpflug angle, and decodes the predetermined blurring as function of the certain Scheimpflug angle. The light field camera may include an autofocusing of the image obtained using the tilting mechanism based on the principle that scene points that are not in focus are blurred while scene points in focus are sharp. The autofocusing may study a small region around a given pixel; the region is expected to get sharper as the Scheimpflug adjustment gets better, and vice versa. Additionally or alternatively, the autofocusing may use the variance of the neighborhood around each pixel as a measure of sharpness, where a proper Scheimpflug adjustment should increase the variance.

Thermal and/or FSCC patterns corresponding to physiological responses may show high variability between different users due to variability of the their brains, blood vessel locations, skin properties, hair, physical conditions, and face shapes and sizes. Thus, patterns and/or various extractable features from one user's thermal and/or FSCC data may not be easily transferable to another user, or even to the same user under different physiological and/or mental conditions. Therefore, some of the embodiments described herein involve training personalized models involving thermal and/or FSCC patterns that are predictive of various user-defined categories of experiencing and/or perceiving certain events. Personalized models can overcome some of the possible disadvantages of using normed physiological statistics, which paves the way for personalized training, detection, and therapies, which are able to account for arbitrary user-defined physiological and/or mental states corresponding to a wide variety of individual needs. Leveraging machine learning algorithms can enable assignment of arbitrary user-defined physiological and/or mental states to recorded thermal and/or FSCC data during day-to-day activities, which are later used as basis for automatic detection and/or therapies for the user, optionally without involving a clinician.

The personalized model does not need to correspond to a standard universally applicable pattern, and thus the user may be free to define his/her arbitrary user-defined physiological and/or mental states. In other words, in addition to (or instead of) detecting a state that corresponds to some arbitrary population average, the personalized model allows a personalized detection of a user-defined state.

One embodiment in which a personalized model is utilized involves a training phase and an operation phase. In the training phase, the system identifies desired and/or undesired physiological and/or mental states of the user using active methods (e.g., the user presses a button) and/or passive methods (e.g., applying semantic analysis to the user's speech and typing). The system may also continue to update the personalized model to accommodate for changes over time, to supports increased efficacy, and to identify new personalized states beyond those represented by population average. Instead of relying on a model trained based on data obtained from a wide population, the personalized model may decouple commonly coupled ROIs and/or putative physiological responses from the applications, allowing the user to train the system to detect arbitrary personalized thermal and/or FSCC patterns that may not suite the wide population. Training the personalized model may be based on known machine learning methods such as neural networks, supervised machine learning, pattern recognition, pattern matching, etc. The system may detect, predict, and train for the arbitrary user-defined physiological and/or mental states, identified by personalized thermal and/or FSCC patterns, not limited to averages obtained from a wide population.

In the operation phase, the system alerts, predicts, and/or treats the user based on the personalized model. The system may alert when the user is in the desired/undesired state, predict when the user is going to be in that state, and treat the user to get into a desired state or avoid an undesired state by providing a feedback. The operation phase may include known biofeedback/neurofeedback interactive sessions tuned to guide the user towards the user-defined personalized physiological and/or mental states. For example, the personalized model may be trained to guide the user towards flow, creativity, curiosity, compassion, and/or happiness states, as defined and experienced by the user, and to alert against anger, aggression, boredom, and/or sadness, also as defined and experienced by the user, without these necessarily being suitable for the wide population.

One embodiment of a method for personalized thermal and/or FSCC detection includes a timestamping step, a machine learning step, a refinement step, an optional detection step, and an optional biofeedback step (where biofeedback refers also to neurofeedback).

In the timestamping step, an HMS records arbitrary user-defined physiological and/or mental states for personal use. The user may provide, via a user interface, timestamped markers on the recorded data used as labels by machine learning approaches for detecting target user-defined physiological and/or mental states (which may be desired or undesired states). When the user engages in a certain task, and as the user enters a target state, the user may (via a user interface) manual provide a timestamp to mark the time of entering into the target state, and/or the computer may set an automated timestamp based on inferring the entering into the target state from the user's performance and/or activities (for example, using predetermined limits of performance that once reached automatically trigger timestamping the recorded data as entering into the target state). Upon leaving the target state, the user may provide a timestamp to mark the leaving of the target state, and/or the computer may set an automated time stamp based on inferring the leaving of the target state from the user's performance and/or activities. Several iterations involving timestamping of entering and leaving the target state may complete the timestamping step.

In the machine learning step, the computer extracts and selects features from the thermal and/or FSCC measurements, labels the extracted and selected features according to the timestamps, and tries one or more machine learning algorithms to train a classifier, while treating the measurements as the training and testing sets. Optionally, for unique personalized states, the machine learning algorithm may be optimized for cross-validation by splitting the training set into a first part used for training and a second part used for testing. In addition, testing sets comprising data of other users may be used to measure the classifier's generality. The following examples illustrate various ways to label the HMS measurements based on the timestamps.

In a first example, the computer may (i) label as "not desired" $TH_{ROI}$ taken before receiving from the user a first timestamp marking the entering into a desired state, (ii) label as "desired" $TH_{ROI}$ taken after receiving the first timestamp and before receiving a second timestamp marking the leaving of the desired state, and (iii) label as "not desired" $TH_{ROI}$ taken after receiving the second timestamp. Optionally, the computer may label as "unknown" $TH_{ROI}$ taken sufficiently before receiving the first timestamp and $TH_{ROI}$ taken sufficiently after receiving the second timestamp.

In a second example, the computer may (i) label as "leading to headache" $TH_{ROI}$ taken during a first window of time before receiving from the user a first timestamp marking occurrence of a headache, (ii) label as "headache" $TH_{ROI}$ taken after receiving the first timestamp and until a second window before receiving from the user a second timestamp marking "no headache", (iii) label as "headache leaving" $TH_{ROI}$ taken during the second window, and (iv) label as "no headache" $TH_{ROI}$ taken after receiving the second timestamp.

In a third example, the computer may (i) label as "leading to asthma attack" $TH_{breath}$ indicative of the user's breathing pattern (such as thermal measurements of a region on the upper lip) taken during a first window before identifying that the user uses a first inhaler, (ii) label as "first inhaler immediate effect" $TH_{breath}$ taken during a second window after using the first inhaler, (iii) label as "first inhaler long effect" $TH_{breath}$ taken during a third window following the second window, and (iv) label as "second inhaler immediate effect" $TH_{breath}$ taken during a fourth window after identifying that the user uses a second inhaler. Optionally, the computer may use the automated labeling for assessing the user's reaction to using the first inhaler vs using the second inhaler.

In a fourth example, the computer may (i) label as "building concentration" $TH_{breath}$ indicative of the user's breathing pattern and $TH_{forehead}$ indicative of a thermal pattern on the user's forehead taken while the user's software agent indicates that the user does not check distracting websites (such as social networks, news and email) but the user's gaze is not essentially continuously focused on the screen, (ii) label as "concentrated" $TH_{breath}$ and $TH_{forehead}$ taken while the software agent indicates that the user's gaze is continuously focused on the screen and until a certain duration before the user lost concentration, and (iii) label as "start losing concentration" $TH_{breath}$ and $TH_{forehead}$ taken during the certain duration.

In a fifth example, the computer may (i) label as "possibly happy" $TH_{ROI}$ and FSCC taken during a first window before a speech analysis module provides a timestamp that the user is happy, (ii) label as "happy" $TH_{ROI}$ and FSCC taken during a second window after receiving the timestamp, and (iii) label as "angry" $TH_{ROI}$ and FSCC taken during a third window after the speech analysis module provides a timestamp that the user is angry.

In the refinement step, the computer starts guessing the physiological and/or mental states, and asks the user to confirm correct, incorrect, or inapplicable status of the guesses. The refinement step increases fidelity the more it is performed.

In the optional detection step, the computer analyzes in real time feature values generated based on the thermal and/or FSCC measurements in order to alert the user about entering and/or leaving a target state. For example, the computer permits administration of pain medication to the user after the classifier determines that the user experiences pain above a threshold previously determined by the user during the timestamping step. This may reduce addiction by reducing unnecessary administrations of higher dose pain medication. Additionally, the user may be trained to control his/her pain perception during the biofeedback step, which may be more effective after a personalized model has been applied.

In the optional biofeedback step, the computer generates a feedback for the user based on the personalized target state. The biofeedback step may use a standard biofeedback protocol, but instead of training the user towards achieving externally derived thermal and/or FSCC target patterns that suit the wide population, the user is trained to achieve personalized thermal and/or FSCC target patterns that most closely resemble the thermal and/or FSCC patterns found to be predictive during the timestamping and refinement steps.

In one embodiment, the user labels during the timestamping step pairs of undesired and desired states (such as pain vs no pain, migraine vs no migraine, angry vs calmed, stressed vs calmed, concentrated vs not concentrated, sad vs happy, self-focused vs compassionate). Then the biofeedback step trains the user to move out of the undesired state by (i) encouraging changes that bring the current measured thermal and/or FSCC pattern closer to the desired personalized thermal and/or FSCC pattern found to be predictive during the timestamping and refinement steps, and (ii) discouraging changes that bring the current measured thermal and/or FSCC pattern closer to the undesired personalized thermal and/or FSCC pattern found to be predictive during the timestamping and refinement steps.

The following is one example of the information flow in an HMS that includes a head-mounted thermal camera and a computer. In the timestamping step, the head-mounted thermal camera takes thermal measurements, and the user (or computer) adds manual (or automated) timestamps for entering and/or leaving a target state. The timestamping step feeds the machine learning step, in which a machine learning-based training algorithm is used to train a personalized model that is evaluated against user measurements in known states. The machine learning step feeds the refinement step with processed data and questions, and in the refinement step the user answers whether the machine learning algorithm has correctly detected the user's state. Both the machine learning step and the refinement step may provide data to the optional detection and biofeedback steps (which may communicate with each other).

Big data analysis may be performed to identify trends and detect new correlations over users and populations, together with other sources of information, such as other wearable devices (e.g., smart watches, smart shirts, EEG headsets, smart earphones), mobile devices (e.g., smartphone, laptop), and other sources of information (e.g., social networks, search engines, bots, software agents, medical records, IoT devices).

Various embodiments described herein involve an HMS that may be connected, using wires and/or wirelessly, with a device carried by the user and/or a non-wearable device. The HMS may include a battery, a computer, sensors, and a transceiver.

Figure 34A:
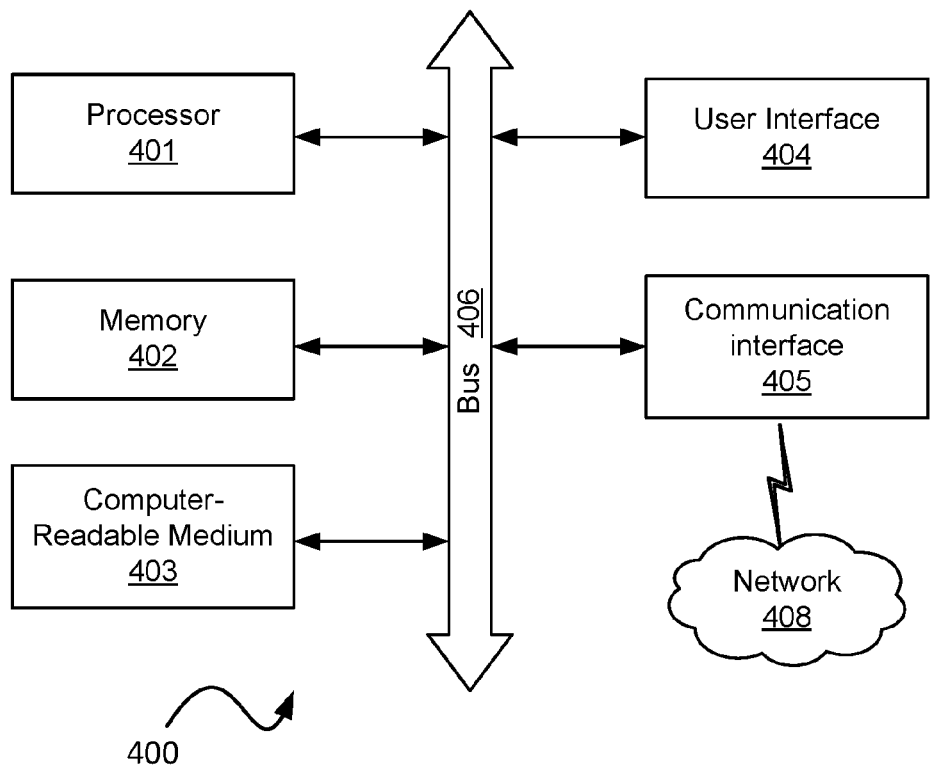
FIG. 34a and FIG. 34b are schematic illustrations of possible embodiments for computers.
Figure 34B:
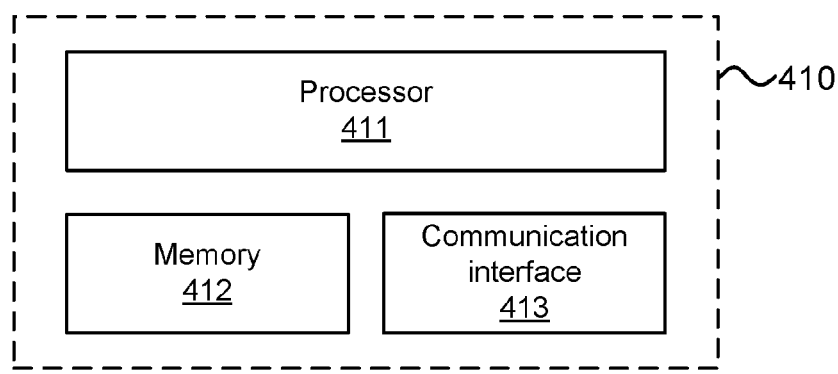

FIG. 34a and FIG. 34b are schematic illustrations of possible embodiments for computers (400, 410) that are able to realize one or more of the embodiments discussed herein that include a "computer". The computer (400, 410) may be implemented in various ways, such as, but not limited to, a server, a client, a personal computer, a network device, a handheld device (e.g., a smartphone), an HMS (such as smart glasses, an augmented reality system, and/or a virtual reality system), a computing device embedded in a wearable device (e.g., a smartwatch or a computer embedded in clothing), a computing device implanted in the human body, and/or any other computer form capable of executing a set of computer instructions. Herein, an augmented reality system refers also to a mixed reality system. Further, references to a computer or processor include any collection of one or more computers and/or processors (which may be at different locations) that individually or jointly execute one or more sets of computer instructions. For example, a first computer may be embedded in the HMS that communicates with a second computer embedded in the user's smartphone that communicates over the Internet with a cloud computer.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Thermal measurements that are forwarded to a processor/computer may include "raw" values that are essentially the same as the values measured by thermal cameras, and/or processed values that are the result of applying some form of preprocessing and/or analysis to the raw values. Examples of methods that may be used to process the raw values include analog signal processing, digital signal processing, and various forms of normalization, noise cancellation, and/or feature extraction.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store and/or Google Play. Optionally, the computer program may be downloaded from a repository, such as an open source and/or community run repository (e.g., GitHub).

At least some of the methods described herein are "computer-implemented methods" that are implemented on a computer, such as the computer (400, 410), by executing instructions on the processor (401, 411). Additionally, at least some of these instructions may be stored on a non-transitory computer-readable medium.

Herein, a direction of the optical axis of a VCAM or a CAM that has focusing optics is determined by the focusing optics, while the direction of the optical axis of a CAM without focusing optics (such as a single pixel thermopile) is determined by the angle of maximum responsivity of its sensor. When optics are utilized to take measurements with a CAM, then the term CAM includes the optics (e.g., one or more lenses). In some embodiments, the optics of a CAM may include one or more lenses made of a material suitable for the required wavelength, such as one or more of the following materials: Calcium Fluoride, Gallium Arsenide, Germanium, Potassium Bromide, Sapphire, Silicon, Sodium Chloride, and Zinc Sulfide. In other embodiments, the CAM optics may include one or more diffractive optical elements, and/or or a combination of one or more diffractive optical elements and one or more refractive optical elements.

When CAM includes an optical limiter/field limiter/FOV limiter (such as a thermopile sensor inside a standard TO-39 package with a window, or a thermopile sensor with a polished metal field limiter), then the term CAM may also refer to the optical limiter. Depending on the context, the term CAM may also refer to a readout circuit adjacent to CAM, and/or to the housing that holds CAM.

Herein, references to thermal measurements in the context of calculating values based on thermal measurements, generating feature values based on thermal measurements, or comparison of thermal measurements, relate to the values of the thermal measurements (which are values of temperature or values of temperature changes). Thus, a sentence in the form of "calculating based on $TH_{ROI}$" may be interpreted as "calculating based on the values of $TH_{ROI}$", and a sentence in the form of "comparing $TH_{ROI1}$ and $TH_{ROI2}$" may be interpreted as "comparing values of $TH_{ROI1}$ and values of $TH_{ROI2}$".

Depending on the embodiment, thermal measurements of an ROI (usually denoted $TH_{ROI}$ or using a similar notation) may have various forms, such as time series, measurements taken according to a varying sampling frequency, and/or measurements taken at irregular intervals. In some embodiments, thermal measurements may include various statistics of the temperature measurements (T) and/or the changes to temperature measurements ($\Delta T$), such as minimum, maximum, and/or average values. Thermal measurements may be raw and/or processed values. When a thermal camera has multiple sensing elements (pixels), the thermal measurements may include values corresponding to each of the pixels, and/or include values representing processing of the values of the pixels. The thermal measurements may be normalized, such as normalized with respect to a baseline (which is based on earlier thermal measurements), time of day, day in the month, type of activity being conducted by the user, and/or various environmental parameters (e.g., the environment's temperature, humidity, radiation level, etc.).

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. For example, sentences in the form of "thermal measurements indicative of a physiological response" mean that the thermal measurements include information from which it is possible to infer the physiological response. Stating that "X indicates Y" or "X indicating Y" may be interpreted as "X being indicative of Y". Additionally, sentences in the form of "provide/receive an indication indicating whether X happened" may refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined as above 51% of the something (including 100% of the something). Both a "portion" of something and a "region" of something refer herein to a value between a fraction of the something and 100% of the something. For example, sentences in the form of a "portion of an area" may cover between 0.1% and 100% of the area. As another example, sentences in the form of a "region on the user's forehead" may cover between the smallest area captured by a single pixel (such as 0.1% or 5% of the forehead) and 100% of the forehead. The word "region" refers to an open-ended claim language, and a camera said to capture a specific region on the face may capture just a small part of the specific region, the entire specific region, and/or a portion of the specific region together with additional region(s).

Sentences in the form of "angle greater than 20°" refer to absolute values (which may be +20° or −20° in this example), unless specifically indicated, such as in a phrase having the form of "the optical axis of CAM is 20° above/below the Frankfort horizontal plane" where it is clearly indicated that the CAM is pointed upwards/downwards. The Frankfort horizontal plane is created by two lines from the superior aspects of the right/left external auditory canal to the most inferior point of the right/left orbital rims.

The terms "comprises," "comprising," "includes," "including," "has," "having", or any other variation thereof, indicate an open-ended claim language that does not exclude additional limitations. The "a" or "an" is employed to describe one or more, and the singular also includes the plural unless it is obvious that it is meant otherwise; for example, sentences in the form of "a CAM configured to take thermal measurements of a region ($TH_{ROI}$)" refers to one or more CAMs that take thermal measurements of one or more regions, including one CAM that takes thermal measurements of multiple regions; as another example, "a computer" refers to one or more computers, such as a combination of a wearable computer that operates together with a cloud computer.

The phrase "based on" is intended to mean "based, at least in part, on". Additionally, stating that a value is calculated "based on X" and following that, in a certain embodiment, that the value is calculated "also based on Y", means that in the certain embodiment, the value is calculated based on X and Y.

The terms "first", "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A system configured to detect a physiological response, comprising:
   an inward-facing head-mounted thermal camera ($CAM_{in}$) configured to take thermal measurements of a region of interest ($TH_{ROI}$) on a user's face; wherein $CAM_{in}$ does not occlude the region of interest (ROI) and is located less than 15 cm from the user's face;
   an outward-facing head-mounted thermal camera ($CAM_{out}$) configured to take thermal measurements of the environment ($TH_{ENV}$), and is located less than 15 cm from the face; and
   a computer configured to detect the physiological response from feature values generated based on $TH_{ROI}$ and $TH_{ENV}$.

2. The system of claim 1, wherein the computer is further configured to generate the feature values based on sets of $TH_{ROI}$ and $TH_{ENV}$, and to utilize a machine learning-based model to detect, based on the feature values, the physiological response; wherein responsive to receiving a first set of measurements in which $TH_{ROI}$ reaches a first threshold while $TH_{ENV}$ does not reach a second threshold, the computer detects the physiological response; and wherein responsive to receiving a second set of measurements in which $TH_{ROI}$ reaches the first threshold while $TH_{ENV}$ reaches the second threshold, the computer does not detect the physiological response.

3. The system of claim 1, wherein the field of view (FOV) of $CAM_{in}$ is larger than the FOV of $CAM_{out}$, and the noise equivalent differential temperature (NEDT) of $CAM_{in}$ is lower than NEDT of $CAM_{out}$.

4. The system of claim 1, wherein, on average, detections of the physiological responses based on $TH_{ROI}$ and $TH_{ENV}$ are more accurate compared to detections of the physiological responses based on $TH_{ROI}$ without $TH_{ENV}$; and wherein $CAM_{in}$ has a field of view (FOV) smaller than 80°, $CAM_{out}$ has a FOV larger than 80°, and $CAM_{in}$ has more sensing elements than $CAM_{out}$.

5. The system of claim 1, wherein the angle between the optical axes of $CAM_{in}$ and $CAM_{out}$ is at least one of the following angles: 45°, 90°, 130°, 170°, and 180°; and wherein $CAM_{in}$ and $CAM_{out}$ are based on sensors of the same type and are located less than 5 cm apart.

6. The system of claim 1, further comprising an eyeglasses frame configured to be worn on the user's head; wherein $CAM_{in}$ and $CAM_{out}$ each weigh below 5 g and are physically coupled to the frame.

7. The system of claim 1, wherein the region of interest includes a region on the forehead of the user and the physiological response comprises at least one of the following: stress, a headache, and a stroke.

8. The system of claim 1, wherein the region of interest includes a region on the nose of the user and the physiological response is an allergic reaction.

9. The system of claim 1, further comprising a second outward-facing head-mounted thermal camera ($CAM_{out2}$) configured to take thermal measurements of the environment ($TH_{ENV2}$); wherein there is an angle of at least 30° between the optical axes of $CAM_{out}$ and $CAM_{out2}$; responsive to receiving a first set of measurements in which $TH_{Rot}$ reach a first threshold while the difference between $TH_{ENV}$ and $TH_{ENV2}$ does not reach a second threshold, the computer detects the physiological response; and responsive to receiving a second set of measurements in which $TH_{ROI}$ reach the first threshold while the difference between $TH_{ENV}$ and $TH_{ENV2}$ reaches the second threshold, the computer does not detect the physiological response.

10. The system of claim 1, further comprising a second outward-facing head-mounted thermal camera ($CAM_{out2}$) configured to take thermal measurements of the environment ($TH_{ENV2}$); wherein there is an angle of at least 30° between the optical axes of $CAM_{out}$ and $CAM_{out2}$; and wherein the computer is configured to detect the physiological response based on a difference between $TH_{ROI}$, $TH_{ENV}$, and $TH_{ENV2}$, while taking into account the angle between the optical axes of $CAM_{out}$ and $CAM_{out2}$ and a graph of responsivity as function of the angle from the optical axes of each of $CAM_{out}$ and $CAM_{out2}$.

11. The system of claim 1, wherein $CAM_{in}$ and $CAM_{out}$ are located to the right of the vertical symmetry axis that divides the user's face, and the ROI is on the right side of the face; and further comprising a second inward-facing head-mounted thermal camera ($CAM_{in2}$) and a second outward-facing head-mounted thermal camera ($CAM_{out2}$) located to the left of the vertical symmetry axis; $CAM_{in2}$ is configured to take thermal measurements of a second ROI ($TH_{ROI2}$) on the left side of the face, and does not occlude $ROI_2$; $CAM_{out2}$ is configured to take thermal measurements of an environment ($TH_{ENV2}$) that is more to the left relative to the environment measured by $CAM_{out}$; wherein the computer is configured to detect the physiological response also based on $TH_{ROI2}$ and $TH_{ENV2}$.

12. The system of claim 1, wherein the optical axes of $CAM_{in}$ and $CAM_{out}$ are above the Frankfort horizontal plane; and further comprising a second inward-facing head-mounted thermal camera ($CAM_{in2}$) and a second outward-facing head-mounted thermal camera ($CAM_{out2}$), located such that their optical axes are below the Frankfort horizontal plane, and configured to take thermal measurements $TH_{ROI2}$ and $TH_{ENV2}$, respectively; wherein the computer is configured to detect the physiological response also based on $TH_{ROI2}$ and $TH_{ENV2}$.

13. The system of claim 1, further comprising a sensor configured to take measurements ($m_{conf}$) that are indicative of at least one of the following: an extent of the user's activity, an orientation of the user's head, and a change in a position of the user's body; wherein the sensor comprises one or more of the following sensors: (i) a movement sensor that is physically coupled to a frame worn on the user's head or to a wearable device worn by the user, (ii) a visible-light camera configured to take images of the user, and (iii) an active 3D tracking device configured to emit electromagnetic waves and generate 3D images based on received reflections of the emitted electromagnetic waves; and wherein the computer is further configured to detect the physiological response also based on $m_{conf}$.

14. The system of claim 13, wherein the computer is further configured to generate feature values based on $TH_{ROI}$, $TH_{ENV}$, and $m_{conf}$ and to utilize a model to detect the physiological response based on the feature values; wherein the model was trained based on: a first set of previous $TH_{ROI}$, $TH_{ENV}$, and $m_{conf}$ taken while the user was walking or running, and a second set of previous $TH_{ROI}$, $TH_{ENV}$, and $m_{conf}$ taken while the user was sitting or standing.

15. The system of claim 13, wherein $m_{conf}$ are indicative of bending the head down above a certain degree from the normal to earth; wherein the computer is further configured to generate feature values based on $TH_{ROI}$, $TH_{ENV}$, and $m_{conf}$, and to utilize a model to detect the physiological response based on the feature values; wherein the model was trained based on: a first set of $TH_{ROI}$, $TH_{ENV}$, and $m_{conf}$ taken while the user was bending the head down above the certain degree, and a second set of previous $TH_{ROI}$, $TH_{ENV}$, and $m_{conf}$ taken while the user was not bending the head down above the certain degree.

16. The system of claim 1, further comprising an anemometer that is physically coupled to a frame worn on the user's head, is located less than 15 cm from the face, and is configured to provide a value indicative of a speed of air directed at the face ($m_{wind}$); wherein the computer is further configured to detect the physiological response also based on $m_{wind}$.

17. The system of claim 16, wherein the computer is further configured to generate feature values based on $TH_{ROI}$, $TH_{ENV}$, and $m_{wind}$, and to utilize a model to detect, based on the feature values, the physiological response; wherein the model was trained based on: a first set of $TH_{ROI}$, $TH_{ENV}$, and $m_{wind}$ taken while being indoors, and a second set of $TH_{ROI}$, $TH_{ENV}$, and $m_{wind}$ taken while being outdoors.

18. The system of claim 1, wherein the computer is configured to detect the physiological response based on a difference between $TH_{ROI}$ and $TH_{ENV}$; whereby detecting the physiological response based on the difference enables the system to operate well in an uncontrolled environment that does not maintain environmental temperature in a range below ±3° C. and does not maintain humidity in a range below ±10%.

19. A method for detecting a physiological response, comprising:
taking thermal measurements of a region of interest ($TH_{ROI}$) on a user's face utilizing an inward-facing head-mounted thermal camera ($CAM_{in}$);
taking thermal measurements of the environment ($TH_{ENV}$) utilizing an outward-facing head-mounted thermal camera ($CAM_{out}$) worn by the user;
generating feature values based on $TH_{ROI}$ and $TH_{ENV}$; and
utilizing a machine learning-based model to detect the physiological response based on the feature values; wherein one or more of the feature values are generated based on $TH_{ENV}$ and are utilized to account for at least some heat transferred from the environment to the region of interest.

20. The method of claim 19, further comprising: taking a first set of $TH_{ROI}$ (first $TH_{ROI}$), wherein the first $TH_{ROI}$ reach a first threshold; taking a first set of $TH_{ENV}$ (first $TH_{ENV}$), wherein the first set of $TH_{ENV}$ do not reach a second threshold; detecting, based on the first set of $TH_{ROI}$ and the first set of $TH_{ENV}$, that the user had the physiological response; taking a second set of $TH_{ROI}$, wherein the second set of $TH_{ROI}$ reach the first threshold; taking a second set of $TH_{ENV}$, wherein the second set of $TH_{ENV}$ reach the second threshold; and detecting, based on the second set of $TH_{ROI}$ and the second set of $TH_{ENV}$, that the user did not have the physiological response.

21. The method of claim 19, further comprising: receiving measurements ($m_{conf}$) that are indicative of at least one of the following: an extent of the user's activity, an orientation of the user's head, and a change in a position of the user's body, and generating one or more feature values used to detect the physiological response based on $m_{conf}$.

* * * * *

UNITED STATES PATENT AND TRADEMARK OFFICE
CERTIFICATE OF CORRECTION

PATENT NO. : 10,151,636 B2
APPLICATION NO. : 15/833079
DATED : December 11, 2018
INVENTOR(S) : Arie Tzvieli, Gil Thieberger and Ari M. Frank It is certified that error appears in the above-identified patent and that said Letters Patent is hereby corrected as shown below:

In the Claims

Claim 1, Column 62, Line 61, delete "from feature values generated".

Claim 2, Column 62, Line 64, delete "the feature" and insert --feature--, therefor.

Signed and Sealed this
Eighth Day of January, 2019

Andrei Iancu
*Director of the United States Patent and Trademark Office*